US008183207B2

(12) United States Patent
Lin et al.

(10) Patent No.: US 8,183,207 B2
(45) Date of Patent: May 22, 2012

(54) TREATMENT OF OSTEOLYTIC DISORDERS AND CANCER USING CSF1R EXTRACELLULAR DOMAIN FUSION MOLECULES

(75) Inventors: Haishan Lin, Moraga, CA (US); Li Long, Lafayette, CA (US)

(73) Assignee: Five Prime Therapeutics, Inc., South San Francisco, CA (US)

( * ) Notice: Subject to any disclaimer, the term of this patent is extended or adjusted under 35 U.S.C. 154(b) by 27 days.

(21) Appl. No.: 12/626,583

(22) Filed: Nov. 25, 2009

(65) Prior Publication Data

US 2010/0136006 A1 Jun. 3, 2010

Related U.S. Application Data

(60) Provisional application No. 61/118,427, filed on Nov. 26, 2008.

(51) Int. Cl.
*A61P 19/08* (2006.01)
*A61K 38/16* (2006.01)
*A61K 38/18* (2006.01)
*C07K 14/53* (2006.01)
*C12N 15/00* (2006.01)

(52) U.S. Cl. ........ 514/16.7; 514/7.6; 514/7.9; 514/21.2; 530/350; 435/69.7; 435/70.1

(58) Field of Classification Search ................. None
See application file for complete search history.

(56) References Cited

U.S. PATENT DOCUMENTS

| | | | |
|---|---|---|---|
| 5,866,114 | A | 2/1999 | Pandit et al. |
| 6,184,354 | B1 | 2/2001 | Koths et al. |
| 7,108,852 | B2 | 9/2006 | Devalaraja et al. |
| 7,247,618 | B2 | 7/2007 | Rajavashisth |
| 7,455,836 | B2 | 11/2008 | Hamilton et al. |
| 2002/0119494 | A1 | 8/2002 | Jung et al. |
| 2006/0286102 | A1 | 12/2006 | Jin et al. |
| 2007/0148172 | A1 | 6/2007 | Lawson et al. |
| 2007/0166788 | A1 | 7/2007 | Jin et al. |
| 2010/0136007 | A1 | 6/2010 | Lin et al. |

FOREIGN PATENT DOCUMENTS

| | | |
|---|---|---|
| CA | 2388298 A1 | 5/2001 |
| EP | 2241333 A1 | 10/2010 |
| WO | WO 89/03687 A1 | 5/1989 |
| WO | WO 99/29345 A1 | 6/1999 |
| WO | WO 01/34177 A2 | 5/2001 |
| WO | WO 2004/045532 A2 | 6/2004 |
| WO | WO 2005/070447 A2 | 8/2005 |
| WO | WO 2006/012451 A2 | 2/2006 |
| WO | WO 2007/075933 A2 | 7/2007 |
| WO | WO 2007/081879 * | 7/2007 |
| WO | WO 2007/081879 A2 | 7/2007 |
| WO | WO 2007/120252 A2 | 10/2007 |
| WO | WO 2008/060610 A2 | 5/2008 |
| WO | WO 2008/124858 A2 | 10/2008 |
| WO | WO 2008/150383 A2 | 12/2008 |
| WO | WO 2009/026303 A1 | 2/2009 |
| WO | WO 2009/112245 A1 | 9/2009 |

OTHER PUBLICATIONS

Wang et al., Mol. Cell. Biol., 1993, vol. 13(9):5348-5359.*
Weihofen et al., J. Biol. Chem., 2000, vol. 275(40):30951-30956.*
Walsh et al., Nat. Biotechnol., 2006, vol. 24(10):1241-1252.*
Aharinejad et al., Colony-stimulating Factor-1 Blockade by Antisense Oligonucleotides and Small Interfering RNAs Suppresses Growth of Human Mammary Tumor Xenografts in Mice, Cancer Research, vol. 64, Aug. 2004, pp. 5378-5384.
Aharinejad et al., Colony-stimulating Factor-1 Antisense Treatment Suppresses Growth of Human Tumor Xenografts in Mice, Cancer Research, vol. 62, Sep. 2002, pp. 5317-5324.
Ando et al., Imatinib Mesylate Inhibits Osteoclastogenesis and Joint Destruction in Rats with Collagen-induced Arthritis, J. Bone Miner. Metab., vol. 24, Jan. 2006, pp. 274-282.
Apollo Cytokine Research, Human hcx$^{TM}$ M-CSF R, Fc Chimera, Product Information Sheet from http://www.biocompare.com/itemdetails.asp?itemid=837066, printed Feb. 4, 2008 (2 pages).
Birchenall-Roberts, Inhibition of Murine Monocyte Proliferation by a Colony-stimulating Factor-1 Antisense Oligodeoxynucleotide, J. Immunol., vol. 145, Nov. 1990, pp. 3290-3296.
Bischof et al., Exacerbation of Acute Inflammatory Arthritis by the Colony-stimulating Factors CSF-1 and Granulocyte Macrophage (GM)-CSF: Evidence of Macrophage Infiltration and Local Proliferation, Clin. Exp. Immunol., vol. 119, 2000, pp. 361-367.
Campbell et al., The Colony-stimulating Factors and Collagen-induced Arthritis: Exacerbation of Disease by M-CSF and G-CSF and Requirement for Endogenous M-CSF, J. Leukoc. Biol., vol. 68, Jul. 2000, pp. 144-150.
Chaika et al., CSF-1 Receptor/Insulin Receptor Chimera Permits CSF-1-dependent Differentiation of 3T3-L1 Preadipocytes, J. Biol. Chem., vol. 272, No. 18, May 1997, pp. 11968-11974.
Chitu et al, Colony-stimulating Factor-1 in Immunity and Inflammation, Curr. Opin. Immunol., vol. 18, No. 1, Feb. 2006, pp. 39-48.
Conway et al., Inhibition of Colony-stimulating-factor-1 Signaling in vivo with the Orally Bioavailable cFMS Kinase Inhibitor GW2580, PNAS, vol. 102, No. 44, Nov. 2005, pp. 16078-16083.
Conway et al., Effects of the cFMS Kinase Inhibitor 5-(3-Methoxy-4-((4-ethoxybenzyl)oxy)benzyl)pyrimidine-2,4-diamine (GW2580) in Normal and Arthritic Rats, J. Pharmacol. Exp. Therapeutics, vol. 326, No. 1, Apr. 2008, pp. 41-50.
Dandekar et al., Comparison of the Signaling Abilities of the Cytoplasmic Domains of the Insulin Receptor and the Insulin Receptor-related Receptor in 3T3-L1 Adipocytes, Endocrinology, vol. 139, No. 8, 1998, pp. 3578-3584.
Dewar et al., Imatinib as a Potential Antiresorptive Therapy for Bone Disease, Blood, vol. 107, No. 11, Jun. 2006, pp. 4334-4337.

(Continued)

*Primary Examiner* — Xiaozhen Xie
(74) *Attorney, Agent, or Firm* — Finnegan, Henderson, Farabow, Garrett & Dunner, L.L.P.

(57) ABSTRACT

Methods of using colony stimulating factor receptor (CSF1R) extracellular domain (ECD) fusion molecules for treating osteolytic bone loss, cancer metastasis, cancer metastasis-induced osteolytic bone loss, and tumor growth are provided. CSF1R ECD fusion molecules, polynucleotides encoding CSF1R ECD fusion molecules, and methods of making CSF1R ECD fusion molecules are also provided.

12 Claims, 11 Drawing Sheets

OTHER PUBLICATIONS

Goswami et al., Macrophages Promote the Invasion of Breast Carcinoma Cells via a Colony-stimulating Factor-1/Epidermal Growth Factor Paracrine Loop, Cancer Res., vol. 65, No. 12, Jun. 2005, pp. 5278-5283.

Hamilton, CSF-1 Signal Transduction, J. Leukoc. Biol., vol. 62, Aug. 1997, pp. 145-155.

Hamilton, Colony-stimulating Factors in Inflammation and Autoimmunity, Nature Reviews, vol. 8, Jul. 2008, pp. 533-544.

Hegen et al., Utility of Animal Models for Identification of Potential Therapeutics for Rheumatoid Arthritis, Ann. Rheum. Dis., vol. 67, published online Nov. 2007, pp. 1505-1515.

Ide et al., Expression of Colony-stimulating Factor 1 Receptor During Prostate Development and Prostate Cancer Progression, PNAS, vol. 99, No. 22, Oct. 2002, pp. 14404-14409.

Ide et al., Serum Level of Macrophage Colony-stimulating Factor is Increased in Prostate Cancer Patients with Bone Metastasis, Human Cell, vol. 21, No. 1, Feb. 2008, pp. 1-6.

Irvine et al., A CSF-1 Receptor Kinase Inhibitor Targets Effector Functions and Inhibits Pro-inflammatory Cytokine Production from Murine Macrophage Populations, FASEB, vol. 20, Sep. 2006, pp. E1315-E1326.

Kingsley et al., Molecular Biology of Bone Metastasis, Mol. Cancer Ther., vol. 6, No. 10, Oct. 2007, pp. 2609-2617.

Kitaura et al., M-CSF Mediates TNF-induced Inflammatory Osteolysis, J. Clin. Invest., vol. 115, No. 12, Dec. 2005, pp. 3418-3427.

Kluger et al., Macrophage Colony-stimulating Factor-1 Receptor Expression is Associated with Poor Outcome in Breast Cancer by Large Cohort Tissue Microarray Analysis, Clinical Cancer Res, vol. 10, Jan. 2004, pp. 173-177.

Kubota et al., M-CSF Inhibition Selectively Targets Pathological Angiogenesis and Lymphangiogenesis, J. Exp. Med., vol. 206, No. 5, Apr. 2009, pp. 1089-1102.

Kutza et al., Macrophage Colony-stimulating Factor Antagonists Inhibit Replication of HIV-1 in Human Macrophages, J. Immunol., 2000, vol. 164, pp. 4955-4960.

Lee et al., Functional Dissection of Structural Domains in the Receptor for Colony-stimulating Factor-1, J. Biol. Chem., vol. 267, No. 23, Aug. 1992, pp. 16472-16483.

Li et al., Conditional Deletion of the Colony Stimulating Factor-1 Receptor (*c-fms* Proto-Oncogene) in Mice, Genesis, vol. 44, May 2006, pp. 328-335.

Li et al., Role of Dimerization and Modification of the CSF-1 Receptor in its Activation and Internalization During the CSF-1 Response, The EMBO Journal, vol. 10, No. 2, 1991, pp. 277-288.

Lin et al., Colony-stimulating Factor 1 Promotes Progression of Mammary Tumors to Malignancy, J. Exp. Med., vol. 193, No. 6, Mar. 2001, pp. 727-739.

Lin et al., The Macrophage Growth Factor CSF-1 in Mammary Gland Development and Tumor Progression, J. Mammary Gland Biology Neoplasia, vol. 7, Apr. 2002, pp. 147-162.

Lin et al., Discovery of a Cytokine and Its Receptor by Functional Screening of the Extracellular Proteome, Science, vol. 320, May 2008, pp. 807-811.

Lin et al., Regulation of Myeloid Growth and Differentiation by a Novel Cytokine, Interleukin-34 (IL-34), via the CSF-1 Receptor, poster presented at Cytokines in Health & Disease, Fifteenth Annual Conference of the International Cytokine Society (San Francisco, Ca, Oct. 26-30, 2007, 1 page.

Lipton, Future Treatment of Bone Metastases, Clin Cancer Res, vol. 12, 20 Suppl., Oct. 2006, pp. 6305s-6308s.

Lopez-Diego et al., Novel Therapeutic Strategies for Multiple Sclerosis—A Multifaceted Adversary, Nature Reviews Drug Discovery, vol. 7, Nov. 2008, pp. 909-925.

MacDonald et al., An Antibody Against the Colony-stimulating Factor 1 Receptor Depletes the Resident Subset of Monocytes and Tissue- and Tumor-associated Macrophages But Does Not Inhibit Inflammation, Blood, vol. 116, Aug. 2010, pp. 3955-3963.

Mancino et al., Breast Cancer Increases Osteoclastogenesis by Secreting M-CSF and Upregulating RANKL in Stromal Cells, J. Surgical Research, vol. 100, Jul. 2001, pp. 18-24.

Montell, Metastasis Movies, Macrophages, Molecules and More, EMBO Reports, vol. 4, No. 5, Apr. 2003, pp. 458-462.

Mroczko et al., Serum Macrophage-colony Stimulating Factor Levels in Colorectal Cancer Patients Correlate with Lymph Node Metastasis and Poor Prognosis, Clinica Chimica Acta., vol. 380, Feb. 2007, pp. 208-212.

Murray et al., SU11248 Inhibits Tumor Growth and CSF-1R-dependent Osteolysis in an Experimental Breast Cancer Bone Metastasis Model, Clinical & Experimental Metastasis, vol. 20, Aug. 2003, pp. 757-766.

Ohno et al., A c-Fms Tyrosine Kinase Inhibitor, Ki20227, Suppresses Osteoclast Differentiation and Osteolytic Bone Destruction in a Bone Metastasis, Mol. Cancer Ther., vol. 5, Nov. 2006, pp. 2634-2643.

Ohno et al., The Orally-active and Selective c-FMS tyrosine Kinase Inhibitor Ki20227 Inhibits Disease Progression in a Collagen-induced Arthritis Mouse Model, Eur. J. Immunol., vol. 38, 2008, pp. 283-291.

Paniagua et al., c-Fms—mediated Differentiation and Priming of Monocyte Lineage Cells Plays a Central Role in Autoimmune Arthritis, Arthritis Research & Therapy, vol. 12, No. R32, Feb. 2010, pp. 1-45.

Paulus et al., Colony-stimulating Factor-1 Antibody Reverses Chemoresistance in Human MCF-7 Breast Cancer Xenografts, Cancer Res., vol. 66, No. 8, Apr. 2006, pp. 4349-4356.

Pederson et al., Identification of Breast Cancer Cell Line-derived Paracrine Factors that Stimulate Osteoclast Activity, Cancer Research, vol. 59, Nov. 1999, pp. 5849-5855.

Pixley et al., CSF-1 Regulation of the Wandering Macrophage: Complexity in Action, Trends in Cell Biology, vol. 14, No. 11, Nov. 2004, pp. 628-638.

Prince et al., 8: Disorders of bone and mineral other than osteoporosis, MJA, vol. 180, Apr. 2004, pp. 354-359.

Qiu et al., Primary Structure of c-*kit*: Relationship with the CSF-1/PDGF Receptor Kinase Family—Oncogenic Activation of v-*kit* Involves Deletion of Extracellular Domain and C Terminus, The EMBO Journal, vol. 7, No. 4, Jan. 1988, pp. 1003-1011.

R&D Systems, Inc., Recombinant Human M-CSF R/Fc Chimera, Specifications and Use, Catalog No. 329-MR, Nov. 2007, 2 pages.

Rahimi et al., Receptor Chimeras Indicate that the Vascular Endothelial Growth Factor Receptor-1 (VEGFR-1) Modulates Mitogenic Activity of VEGFR-2 in Endothelial Cells, J. Biol. Chem., vol. 275, No. 22, Jun. 2000, pp. 16986-16992.

Ross, M-CSF, c-Fms, and Signaling in Osteoclasts and Their Precursors, Ann. NY Acad. Sci., vol. 1068, 2006, pp. 110-116.

Roussel et al., Colony-stimulating Factor 1-mediated Regulation of a Chimeric c-*fms* / v-*fms* Receptor Containing the v-*fms*-encoded Tyrosine Kinase Domain, PNAS USA, vol. 85, Aug. 1988, pp. 5903-5907.

Sapi, The Role of CSF-1 in Normal Physiology of Mammary Gland and Breast Cancer: An Update, Exp. Biol. Med., vol. 229, 2004, pp. 1-11.

Sarma et al., Macrophage Colony-stimulating Factor Induces Substantial Osteoclast Generation and Bone Resorption in Human Bone Marrow Cultures, Blood, vol. 88, No. 7, Oct. 1996, pp. 2531-2540.

Shaposhnik et al., Arterial Colony Stimulating Factor-1 Influences Atherosclerotic Lesions by Regulating Monocyte Migration and Apoptosis, J. Lipid Research, vol. 51, 2010, pp. 1962-1970.

Sherr et al., Inhibition of Colony-Stimulating Factor-1 Activity by Monoclonal Antibodies to the Human CSF-1 Receptor, Blood, vol. 73, No. 7, May 1989, pp. 1786-1793.

Sherr, Colony-Stimulating Factor-1 Receptor, Blood, vol. 75, No. 1, Jan. 1990, pp. 1-12.

Sigma, Product Information for Macrophage Colony Stimulating Factor Receptor/Fc Chimera (M-CSF R, CD115) Human, Recombinant, Expressed in mouse NSO cells, Product No. M 7559, 2 pages.

Steinman et al., Virtues and Pitfalls of EAE for the Development of Therapies for Multiple Sclerosis, Trends in Immunology, vol. 26, No. 11, Nov. 2005, pp. 565-571.

Suzuki et al., Differences in Bone Responses to Recombinant Human Granulocyte Colony-stimulating Factor Between Mice and Rats, J. Toxicol. Sci., vol. 33, No. 2, 2008, 245-249.

Sweet et al., CSF-1 as a Regulator of Macrophage Activation and Immune Responses, Archivum Immunologiar et Therapiae Experimentalis, vol. 51, 2003, pp. 169-177.

Tamura et al., Tyrosine Kinases as Targets for Anti-inflammatory Therapy, Anti-Inflammatory & Anti-Allergy Agents in Medicinal Chemistry, vol. 6, No. 1, 2007, pp. 47-60.

Tanaka et al., Macrophage Colony-stimulating Factor is Indispensable for Both Proliferation and Differentiation of Osteoclast Progenitors, J. Clin. Invest., vol. 91, Jan. 1993, pp. 257-263.

Teitelbaum, Osteoclasts: What Do They Do and How Do They Do It?, Am. J. Pathol., vol. 170, No. 2, Feb. 2007, pp. 427-435.

Uemura et al., The Selective M-CSF Receptor Tyrosine Kinase Inhibitor Ki20227 Suppresses Experimental Autoimmune Encephalomyelitis, J. Neuroimmunology, vol. 195, Jan. 2008, pp. 73-80.

Usbiological, CD115, Recombinant, Human, Fc Chimera (BSA Free) (c-fms, Fms, CSF-1R, M-CSFR), from Google's cache of http://usbio.net/Product.spx?ProdSku+C2447-52E1, as retrieved on Jan. 16, 2008 (1 page).

Van Daalen Wetters et al., Random Mutagenesis of CSF-1 Receptor (FMS) Reveals Multiple Sites for Activating Mutations within the Extracellular Domain, The EMBO Journal, vol. 11, No. 2, 1992, pp. 551-557.

Virk et al., Tumor metastasis to bone, Arthritis Research & Therapy, vol. 9, Suppl. 1, 2007, S5, pp. 1-10.

Wang et al., Identification of the Ligand-binding Regions in the Macrophage Colony-stimulating Factor Receptor Extracellular Domain, Mol. Cell Biol., Sep. 1993, pp. 5348-5359.

Wu et al., Enhancement of J6-1 Human Leukemic Cell Proliferation by Membrane-bound M-CSF Through a Cell-Cell Contact Mechanism II. Role of an M-CSF Receptor-like Membrane Protein, Leukemia Research, vol. 22, No. 1, 1998, pp. 55-60.

Wyckoff et al., A Paracrine Loop Between Tumor Cells and Macrophages is Required for Tumor Cell Migration in Mammary Tumors, Cancer Research, vol. 64, Oct. 2004, pp. 7022-7029.

Yano et al., Macrophage Colony-stimulating Factor Gene Transduction into Human Lung Cancer Cells Differentially Regulates Metastasis Formulations in Various Organ Microevents of Natural Killer cell-deplete SCID Mice, Cancer Research, vol. 57, Feb. 1997, pp. 784-790.

Yao et al., Tumor Necrosis Factor-$\alpha$ Increases Circulating Osteoclast Precursor Numbers by Promoting Their Proliferation and Differentiation in the Bone Marrow Through Up-regulation of c-Fms Expression, J. Biol. Chem., vol. 281, No. 17, Apr. 2006, pp. 11846-11855.

Zheng et al., Expression of Bioactive Human M-CSF Soluble Receptor in Transgenic Tobacco Plants, Protein Expression and Purification, vol. 46, 2006, pp. 367-373.

Office Action mailed Nov. 16, 2010, for U.S. Appl. No. 12/626,598, 7 pages.

Amendment and Response to Restriction Requirement, filed Feb. 16, 2011, for U.S. Appl. No. 12/626,598, 7 pages.

Office Action mailed Mar. 16, 2011, for U.S. Appl. No. 12/626,598, 13 pages.

International Search Report and Written Opinion mailed May 24, 2010, for Application No. PCT/US 09/06301, filed Nov. 25, 2009.

International Search Report and Written Opinion mailed Jun. 9, 2010, for Application No. PCT/US 09/06299, filed Nov. 25, 2009.

* cited by examiner

SEQUENCE LISTING

<160> NUMBER OF SEQ ID NOS: 38

<210> SEQ ID NO 1
<211> LENGTH: 493
<212> TYPE: PRT
<213> ORGANISM: Artificial Sequence
<220> FEATURE:
<223> OTHER INFORMATION: hCSF1R-ECD.512

<400> SEQUENCE: 1

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
        35                  40                  45

Ile Leu Ser Thr Asn Asn Ala Thr Phe Gln Asn Thr Gly Thr Tyr Arg
    50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
    130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys

```
              210                 215                 220
Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
        275                 280                 285

Asn Leu Ile Gln Glu Val Thr Val Gly Glu Gly Leu Asn Leu Lys Val
    290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335

Thr Lys Asp Thr Tyr Arg His Thr Phe Thr Leu Ser Leu Pro Arg Leu
            340                 345                 350

Lys Pro Ser Glu Ala Gly Arg Tyr Ser Phe Leu Ala Arg Asn Pro Gly
        355                 360                 365

Gly Trp Arg Ala Leu Thr Phe Glu Leu Thr Leu Arg Tyr Pro Pro Glu
    370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415

Gly His Thr Asp Arg Cys Asp Glu Ala Gln Val Leu Gln Val Trp Asp
            420                 425                 430

Asp Pro Tyr Pro Glu Val Leu Ser Gln Glu Pro Phe His Lys Val Thr
        435                 440                 445

Val Gln Ser Leu Leu Thr Val Glu Thr Leu Glu His Asn Gln Thr Tyr
    450                 455                 460

Glu Cys Arg Ala His Asn Ser Val Gly Ser Gly Ser Trp Ala Phe Ile
465                 470                 475                 480

Pro Ile Ser Ala Gly Ala His Thr His Pro Pro Asp Glu
                485                 490

<210> SEQ ID NO 2
<211> LENGTH: 487
<212> TYPE: PRT
<213> ORGANISM: Artificial Sequence
<220> FEATURE:
<223> OTHER INFORMATION: hCSF1R-ECD.506

<400> SEQUENCE: 2

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
                20                  25                  30

Gly Pro Pro Ser Pro His Trp Thr Leu Tyr Ser Asp Gly Ser Ser Ser
            35                  40                  45

Ile Leu Ser Thr Asn Asn Ala Thr Phe Gln Asn Thr Gly Thr Tyr Arg
        50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95
```

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
    130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
            165                 170                 175

Gln Lys Val Ile Pro Gly Pro Ala Leu Thr Leu Val Pro Ala Glu
        180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
    210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
            245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
        275                 280                 285

Asn Leu Ile Gln Glu Val Thr Val Gly Glu Gly Leu Asn Leu Lys Val
    290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
            325                 330                 335

Thr Lys Asp Thr Tyr Arg His Thr Phe Thr Leu Ser Leu Pro Arg Leu
            340                 345                 350

Lys Pro Ser Glu Ala Gly Arg Tyr Ser Phe Leu Ala Arg Asn Pro Gly
        355                 360                 365

Gly Trp Arg Ala Leu Thr Phe Glu Leu Thr Leu Arg Tyr Pro Pro Glu
    370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
            405                 410                 415

Gly His Thr Asp Arg Cys Asp Glu Ala Gln Val Leu Gln Val Trp Asp
            420                 425                 430

Asp Pro Tyr Pro Glu Val Leu Ser Gln Glu Pro Phe His Lys Val Thr
        435                 440                 445

Val Gln Ser Leu Leu Thr Val Glu Thr Leu Glu His Asn Gln Thr Tyr
    450                 455                 460

Glu Cys Arg Ala His Asn Ser Val Gly Ser Gly Ser Trp Ala Phe Ile
465                 470                 475                 480

Pro Ile Ser Ala Gly Ala His
            485

<210> SEQ ID NO 3
<211> LENGTH: 492
<212> TYPE: PRT

-continued

<213> ORGANISM: Artificial Sequence
<220> FEATURE:
<223> OTHER INFORMATION: mCSF1R-ECD.511

<400> SEQUENCE: 3

```
Ala Pro Val Ile Glu Pro Ser Gly Pro Glu Leu Val Val Glu Pro Gly
1               5                   10                  15

Glu Thr Val Thr Leu Arg Cys Val Ser Asn Gly Ser Val Glu Trp Asp
            20                  25                  30

Gly Pro Ile Ser Pro Tyr Trp Thr Leu Asp Pro Glu Ser Pro Gly Ser
        35                  40                  45

Thr Leu Thr Thr Arg Asn Ala Thr Phe Lys Asn Thr Gly Thr Tyr Arg
    50                  55                  60

Cys Thr Glu Leu Glu Asp Pro Met Ala Gly Ser Thr Thr Ile His Leu
65                  70                  75                  80

Tyr Val Lys Asp Pro Ala His Ser Trp Asn Leu Leu Ala Gln Glu Val
                85                  90                  95

Thr Val Val Glu Gly Gln Glu Ala Val Leu Pro Cys Leu Ile Thr Asp
            100                 105                 110

Pro Ala Leu Lys Asp Ser Val Ser Leu Met Arg Glu Gly Gly Arg Gln
        115                 120                 125

Val Leu Arg Lys Thr Val Tyr Phe Phe Ser Pro Trp Arg Gly Phe Ile
    130                 135                 140

Ile Arg Lys Ala Lys Val Leu Asp Ser Asn Thr Tyr Val Cys Lys Thr
145                 150                 155                 160

Met Val Asn Gly Arg Glu Ser Thr Ser Thr Gly Ile Trp Leu Lys Val
                165                 170                 175

Asn Arg Val His Pro Glu Pro Pro Gln Ile Lys Leu Glu Pro Ser Lys
            180                 185                 190

Leu Val Arg Ile Arg Gly Glu Ala Ala Gln Ile Val Cys Ser Ala Thr
        195                 200                 205

Asn Ala Glu Val Gly Phe Asn Val Ile Leu Lys Arg Gly Asp Thr Lys
    210                 215                 220

Leu Glu Ile Pro Leu Asn Ser Asp Phe Gln Asp Asn Tyr Tyr Lys Lys
225                 230                 235                 240

Val Arg Ala Leu Ser Leu Asn Ala Val Asp Phe Gln Asp Ala Gly Ile
                245                 250                 255

Tyr Ser Cys Val Ala Ser Asn Asp Val Gly Thr Arg Thr Ala Thr Met
            260                 265                 270

Asn Phe Gln Val Val Glu Ser Ala Tyr Leu Asn Leu Thr Ser Glu Gln
        275                 280                 285

Ser Leu Leu Gln Glu Val Ser Val Gly Asp Ser Leu Ile Leu Thr Val
    290                 295                 300

His Ala Asp Ala Tyr Pro Ser Ile Gln His Tyr Asn Trp Thr Tyr Leu
305                 310                 315                 320

Gly Pro Phe Phe Glu Asp Gln Arg Lys Leu Glu Phe Ile Thr Gln Arg
                325                 330                 335

Ala Ile Tyr Arg Tyr Thr Phe Lys Leu Phe Leu Asn Arg Val Lys Ala
            340                 345                 350

Ser Glu Ala Gly Gln Tyr Phe Leu Met Ala Gln Asn Lys Ala Gly Trp
        355                 360                 365

Asn Asn Leu Thr Phe Glu Leu Thr Leu Arg Tyr Pro Pro Glu Val Ser
    370                 375                 380

Val Thr Trp Met Pro Val Asn Gly Ser Asp Val Leu Phe Cys Asp Val
385                 390                 395                 400
```

```
Ser Gly Tyr Pro Gln Pro Ser Val Thr Trp Met Glu Cys Arg Gly His
                405                 410                 415

Thr Asp Arg Cys Asp Glu Ala Gln Ala Leu Gln Val Trp Asn Asp Thr
            420                 425                 430

His Pro Glu Val Leu Ser Gln Lys Pro Phe Asp Lys Val Ile Ile Gln
        435                 440                 445

Ser Gln Leu Pro Ile Gly Thr Leu Lys His Asn Met Thr Tyr Phe Cys
    450                 455                 460

Lys Thr His Asn Ser Val Gly Asn Ser Ser Gln Tyr Phe Arg Ala Val
465                 470                 475                 480

Ser Leu Gly Gln Ser Lys Gln Leu Pro Asp Glu Ser
                485                 490

<210> SEQ ID NO 4
<211> LENGTH: 487
<212> TYPE: PRT
<213> ORGANISM: Artificial Sequence
<220> FEATURE:
<223> OTHER INFORMATION: mCSF1R-ECD.506

<400> SEQUENCE: 4

Ala Pro Val Ile Glu Pro Ser Gly Pro Glu Leu Val Val Glu Pro Gly
1               5                   10                  15

Glu Thr Val Thr Leu Arg Cys Val Ser Asn Gly Ser Val Glu Trp Asp
            20                  25                  30

Gly Pro Ile Ser Pro Tyr Trp Thr Leu Asp Pro Glu Ser Pro Gly Ser
        35                  40                  45

Thr Leu Thr Thr Arg Asn Ala Thr Phe Lys Asn Thr Gly Thr Tyr Arg
    50                  55                  60

Cys Thr Glu Leu Glu Asp Pro Met Ala Gly Ser Thr Thr Ile His Leu
65                  70                  75                  80

Tyr Val Lys Asp Pro Ala His Ser Trp Asn Leu Leu Ala Gln Glu Val
                85                  90                  95

Thr Val Val Glu Gly Gln Glu Ala Val Leu Pro Cys Leu Ile Thr Asp
            100                 105                 110

Pro Ala Leu Lys Asp Ser Val Ser Leu Met Arg Glu Gly Gly Arg Gln
        115                 120                 125

Val Leu Arg Lys Thr Val Tyr Phe Phe Ser Pro Trp Arg Gly Phe Ile
    130                 135                 140

Ile Arg Lys Ala Lys Val Leu Asp Ser Asn Thr Tyr Val Cys Lys Thr
145                 150                 155                 160

Met Val Asn Gly Arg Glu Ser Thr Ser Thr Gly Ile Trp Leu Lys Val
                165                 170                 175

Asn Arg Val His Pro Glu Pro Pro Gln Ile Lys Leu Glu Pro Ser Lys
            180                 185                 190

Leu Val Arg Ile Arg Gly Glu Ala Ala Gln Ile Val Cys Ser Ala Thr
        195                 200                 205

Asn Ala Glu Val Gly Phe Asn Val Ile Leu Lys Arg Gly Asp Thr Lys
    210                 215                 220

Leu Glu Ile Pro Leu Asn Ser Asp Phe Gln Asp Asn Tyr Tyr Lys Lys
225                 230                 235                 240

Val Arg Ala Leu Ser Leu Asn Ala Val Asp Phe Gln Asp Ala Gly Ile
                245                 250                 255

Tyr Ser Cys Val Ala Ser Asn Asp Val Gly Thr Arg Thr Ala Thr Met
            260                 265                 270
```

-continued

```
Asn Phe Gln Val Val Glu Ser Ala Tyr Leu Asn Leu Thr Ser Glu Gln
    275                 280                 285

Ser Leu Leu Gln Glu Val Ser Val Gly Asp Ser Leu Ile Leu Thr Val
290                 295                 300

His Ala Asp Ala Tyr Pro Ser Ile Gln His Tyr Asn Trp Thr Tyr Leu
305                 310                 315                 320

Gly Pro Phe Phe Glu Asp Gln Arg Lys Leu Glu Phe Ile Thr Gln Arg
                325                 330                 335

Ala Ile Tyr Arg Tyr Thr Phe Lys Leu Phe Leu Asn Arg Val Lys Ala
            340                 345                 350

Ser Glu Ala Gly Gln Tyr Phe Leu Met Ala Gln Asn Lys Ala Gly Trp
        355                 360                 365

Asn Asn Leu Thr Phe Glu Leu Thr Leu Arg Tyr Pro Pro Glu Val Ser
370                 375                 380

Val Thr Trp Met Pro Val Asn Gly Ser Asp Val Leu Phe Cys Asp Val
385                 390                 395                 400

Ser Gly Tyr Pro Gln Pro Ser Val Thr Trp Met Glu Cys Arg Gly His
                405                 410                 415

Thr Asp Arg Cys Asp Glu Ala Gln Ala Leu Gln Val Trp Asn Asp Thr
            420                 425                 430

His Pro Glu Val Leu Ser Gln Lys Pro Phe Asp Lys Val Ile Ile Gln
        435                 440                 445

Ser Gln Leu Pro Ile Gly Thr Leu Lys His Asn Met Thr Tyr Phe Cys
    450                 455                 460

Lys Thr His Asn Ser Val Gly Asn Ser Ser Gln Tyr Phe Arg Ala Val
465                 470                 475                 480

Ser Leu Gly Gln Ser Lys Gln
                485

<210> SEQ ID NO 5
<211> LENGTH: 725
<212> TYPE: PRT
<213> ORGANISM: Artificial Sequence
<220> FEATURE:
<223> OTHER INFORMATION: hCSF1R-ECD.512-Fc

<400> SEQUENCE: 5

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
        35                  40                  45

Ile Leu Ser Thr Asn Asn Ala Thr Phe Gln Asn Thr Gly Thr Tyr Arg
    50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
    130                 135                 140

Ile His Arg Ala Lys Phe Ile Gln Ser Gln Asp Tyr Gln Cys Ser Ala
```

```
            145                 150                 155                 160
Leu Met Gly Gly Arg Lys Val Met Ser Ile Ser Ile Arg Leu Lys Val
                165                 170                 175
Gln Lys Val Ile Pro Gly Pro Ala Leu Thr Leu Val Pro Ala Glu
            180                 185                 190
Leu Val Arg Ile Arg Gly Glu Ala Ala Gln Ile Val Cys Ser Ala Ser
            195                 200                 205
Ser Val Asp Val Asn Phe Asp Val Phe Leu Gln His Asn Asn Thr Lys
        210                 215                 220
Leu Ala Ile Pro Gln Gln Ser Asp Phe His Asn Asn Arg Tyr Gln Lys
225                 230                 235                 240
Val Leu Thr Leu Asn Leu Asp Gln Val Asp Phe Gln His Ala Gly Asn
                245                 250                 255
Tyr Ser Cys Val Ala Ser Asn Val Gln Gly Lys His Ser Thr Ser Met
                260                 265                 270
Phe Phe Arg Val Val Glu Ser Ala Tyr Leu Asn Leu Ser Ser Glu Gln
            275                 280                 285
Asn Leu Ile Gln Glu Val Thr Val Gly Glu Gly Leu Asn Leu Lys Val
        290                 295                 300
Met Val Glu Ala Tyr Pro Gly Leu Gln Gly Phe Asn Trp Thr Tyr Leu
305                 310                 315                 320
Gly Pro Phe Ser Asp His Gln Pro Glu Pro Lys Leu Ala Asn Ala Thr
                325                 330                 335
Thr Lys Asp Thr Tyr Arg His Thr Phe Thr Leu Ser Leu Pro Arg Leu
                340                 345                 350
Lys Pro Ser Glu Ala Gly Arg Tyr Ser Phe Leu Ala Arg Asn Pro Gly
            355                 360                 365
Gly Trp Arg Ala Leu Thr Phe Glu Leu Thr Leu Arg Tyr Pro Pro Glu
        370                 375                 380
Val Ser Val Ile Trp Thr Phe Ile Asn Gly Ser Gly Thr Leu Leu Cys
385                 390                 395                 400
Ala Ala Ser Gly Tyr Pro Gln Pro Asn Val Thr Trp Leu Gln Cys Ser
                405                 410                 415
Gly His Thr Asp Arg Cys Asp Glu Ala Gln Val Leu Gln Val Trp Asp
            420                 425                 430
Asp Pro Tyr Pro Glu Val Leu Ser Gln Glu Pro Phe His Lys Val Thr
        435                 440                 445
Val Gln Ser Leu Leu Thr Val Glu Thr Leu Glu His Asn Gln Thr Tyr
    450                 455                 460
Glu Cys Arg Ala His Asn Ser Val Gly Ser Gly Ser Trp Ala Phe Ile
465                 470                 475                 480
Pro Ile Ser Ala Gly Ala His Thr His Pro Pro Asp Glu Pro Lys
                485                 490                 495
Ser Ser Asp Lys Thr His Thr Cys Pro Pro Cys Pro Ala Pro Glu Leu
                500                 505                 510
Leu Gly Gly Pro Ser Val Phe Leu Phe Pro Pro Lys Pro Lys Asp Thr
            515                 520                 525
Leu Met Ile Ser Arg Thr Pro Glu Val Thr Cys Val Val Val Asp Val
        530                 535                 540
Ser His Glu Asp Pro Glu Val Lys Phe Asn Trp Tyr Val Asp Gly Val
545                 550                 555                 560
Glu Val His Asn Ala Lys Thr Lys Pro Arg Glu Glu Gln Tyr Asn Ser
                565                 570                 575
```

```
Thr Tyr Arg Val Val Ser Val Leu Thr Val Leu His Gln Asp Trp Leu
            580                 585                 590

Asn Gly Lys Glu Tyr Lys Cys Lys Val Ser Asn Lys Ala Leu Pro Ala
        595                 600                 605

Pro Ile Glu Lys Thr Ile Ser Lys Ala Lys Gly Gln Pro Arg Glu Pro
    610                 615                 620

Gln Val Tyr Thr Leu Pro Pro Ser Arg Asp Glu Leu Thr Lys Asn Gln
625                 630                 635                 640

Val Ser Leu Thr Cys Leu Val Lys Gly Phe Tyr Pro Ser Asp Ile Ala
                645                 650                 655

Val Glu Trp Glu Ser Asn Gly Gln Pro Glu Asn Asn Tyr Lys Thr Thr
            660                 665                 670

Pro Pro Val Leu Asp Ser Asp Gly Ser Phe Phe Leu Tyr Ser Lys Leu
        675                 680                 685

Thr Val Asp Lys Ser Arg Trp Gln Gln Gly Asn Val Phe Ser Cys Ser
    690                 695                 700

Val Met His Glu Ala Leu His Asn His Tyr Thr Gln Lys Ser Leu Ser
705                 710                 715                 720

Leu Ser Pro Gly Lys
            725

<210> SEQ ID NO 6
<211> LENGTH: 719
<212> TYPE: PRT
<213> ORGANISM: Artificial Sequence
<220> FEATURE:
<223> OTHER INFORMATION: hCSF1R-ECD.506-Fc

<400> SEQUENCE: 6

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
        35                  40                  45

Ile Leu Ser Thr Asn Asn Ala Thr Phe Gln Asn Thr Gly Thr Tyr Arg
    50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
    130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
```

```
                 210                 215                 220
Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
                260                 265                 270

Phe Phe Arg Val Val Glu Ser Ala Tyr Leu Asn Leu Ser Ser Glu Gln
                275                 280                 285

Asn Leu Ile Gln Glu Val Thr Val Gly Glu Gly Leu Asn Leu Lys Val
290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335

Thr Lys Asp Thr Tyr Arg His Thr Phe Thr Leu Ser Leu Pro Arg Leu
                340                 345                 350

Lys Pro Ser Glu Ala Gly Arg Tyr Ser Phe Leu Ala Arg Asn Pro Gly
                355                 360                 365

Gly Trp Arg Ala Leu Thr Phe Glu Leu Thr Leu Arg Tyr Pro Pro Glu
370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415

Gly His Thr Asp Arg Cys Asp Glu Ala Gln Val Leu Gln Val Trp Asp
                420                 425                 430

Asp Pro Tyr Pro Glu Val Leu Ser Gln Glu Pro Phe His Lys Val Thr
                435                 440                 445

Val Gln Ser Leu Leu Thr Val Glu Thr Leu Glu His Asn Gln Thr Tyr
                450                 455                 460

Glu Cys Arg Ala His Asn Ser Val Gly Ser Gly Ser Trp Ala Phe Ile
465                 470                 475                 480

Pro Ile Ser Ala Gly Ala His Glu Pro Lys Ser Ser Asp Lys Thr His
                485                 490                 495

Thr Cys Pro Pro Cys Pro Ala Pro Glu Leu Leu Gly Gly Pro Ser Val
                500                 505                 510

Phe Leu Phe Pro Pro Lys Pro Lys Asp Thr Leu Met Ile Ser Arg Thr
                515                 520                 525

Pro Glu Val Thr Cys Val Val Val Asp Val Ser His Glu Asp Pro Glu
530                 535                 540

Val Lys Phe Asn Trp Tyr Val Asp Gly Val Glu Val His Asn Ala Lys
545                 550                 555                 560

Thr Lys Pro Arg Glu Glu Gln Tyr Asn Ser Thr Tyr Arg Val Val Ser
                565                 570                 575

Val Leu Thr Val Leu His Gln Asp Trp Leu Asn Gly Lys Glu Tyr Lys
                580                 585                 590

Cys Lys Val Ser Asn Lys Ala Leu Pro Ala Pro Ile Glu Lys Thr Ile
                595                 600                 605

Ser Lys Ala Lys Gly Gln Pro Arg Glu Pro Gln Val Tyr Thr Leu Pro
                610                 615                 620

Pro Ser Arg Asp Glu Leu Thr Lys Asn Gln Val Ser Leu Thr Cys Leu
625                 630                 635                 640
```

-continued

```
Val Lys Gly Phe Tyr Pro Ser Asp Ile Ala Val Trp Glu Ser Asn
            645                 650                 655

Gly Gln Pro Glu Asn Asn Tyr Lys Thr Thr Pro Pro Val Leu Asp Ser
            660                 665                 670

Asp Gly Ser Phe Phe Leu Tyr Ser Lys Leu Thr Val Asp Lys Ser Arg
            675                 680                 685

Trp Gln Gln Gly Asn Val Phe Ser Cys Ser Val Met His Glu Ala Leu
            690                 695                 700

His Asn His Tyr Thr Gln Lys Ser Leu Ser Leu Ser Pro Gly Lys
705                 710                 715

<210> SEQ ID NO 7
<211> LENGTH: 724
<212> TYPE: PRT
<213> ORGANISM: Artificial Sequence
<220> FEATURE:
<223> OTHER INFORMATION: mCSF1R-ECD.511-Fc

<400> SEQUENCE: 7

Ala Pro Val Ile Glu Pro Ser Gly Pro Glu Leu Val Val Glu Pro Gly
1               5                   10                  15

Glu Thr Val Thr Leu Arg Cys Val Ser Asn Gly Ser Val Glu Trp Asp
            20                  25                  30

Gly Pro Ile Ser Pro Tyr Trp Thr Leu Asp Pro Glu Ser Pro Gly Ser
        35                  40                  45

Thr Leu Thr Thr Arg Asn Ala Thr Phe Lys Asn Thr Gly Thr Tyr Arg
    50                  55                  60

Cys Thr Glu Leu Glu Asp Pro Met Ala Gly Ser Thr Thr Ile His Leu
65                  70                  75                  80

Tyr Val Lys Asp Pro Ala His Ser Trp Asn Leu Leu Ala Gln Glu Val
                85                  90                  95

Thr Val Val Glu Gly Gln Glu Ala Val Leu Pro Cys Leu Ile Thr Asp
            100                 105                 110

Pro Ala Leu Lys Asp Ser Val Ser Leu Met Arg Glu Gly Gly Arg Gln
        115                 120                 125

Val Leu Arg Lys Thr Val Tyr Phe Phe Ser Pro Trp Arg Gly Phe Ile
    130                 135                 140

Ile Arg Lys Ala Lys Val Leu Asp Ser Asn Thr Tyr Val Cys Lys Thr
145                 150                 155                 160

Met Val Asn Gly Arg Glu Ser Thr Ser Thr Gly Ile Trp Leu Lys Val
                165                 170                 175

Asn Arg Val His Pro Glu Pro Pro Gln Ile Lys Leu Glu Pro Ser Lys
            180                 185                 190

Leu Val Arg Ile Arg Gly Glu Ala Ala Gln Ile Val Cys Ser Ala Thr
        195                 200                 205

Asn Ala Glu Val Gly Phe Asn Val Ile Leu Lys Arg Gly Asp Thr Lys
    210                 215                 220

Leu Glu Ile Pro Leu Asn Ser Asp Phe Gln Asp Asn Tyr Tyr Lys Lys
225                 230                 235                 240

Val Arg Ala Leu Ser Leu Asn Ala Val Asp Phe Gln Asp Ala Gly Ile
                245                 250                 255

Tyr Ser Cys Val Ala Ser Asn Asp Val Gly Thr Arg Thr Ala Thr Met
            260                 265                 270

Asn Phe Gln Val Val Glu Ser Ala Tyr Leu Asn Leu Thr Ser Glu Gln
        275                 280                 285

Ser Leu Leu Gln Glu Val Ser Val Gly Asp Ser Leu Ile Leu Thr Val
```

```
            290                 295                 300
His Ala Asp Ala Tyr Pro Ser Ile Gln His Tyr Asn Trp Thr Tyr Leu
305                 310                 315                 320

Gly Pro Phe Phe Glu Asp Gln Arg Lys Leu Glu Phe Ile Thr Gln Arg
                325                 330                 335

Ala Ile Tyr Arg Tyr Thr Phe Lys Leu Phe Leu Asn Arg Val Lys Ala
            340                 345                 350

Ser Glu Ala Gly Gln Tyr Phe Leu Met Ala Gln Asn Lys Ala Gly Trp
        355                 360                 365

Asn Asn Leu Thr Phe Glu Leu Thr Leu Arg Tyr Pro Pro Glu Val Ser
370                 375                 380

Val Thr Trp Met Pro Val Asn Gly Ser Asp Val Leu Phe Cys Asp Val
385                 390                 395                 400

Ser Gly Tyr Pro Gln Pro Ser Val Thr Trp Met Glu Cys Arg Gly His
                405                 410                 415

Thr Asp Arg Cys Asp Glu Ala Gln Ala Leu Gln Val Trp Asn Asp Thr
            420                 425                 430

His Pro Glu Val Leu Ser Gln Lys Pro Phe Asp Lys Val Ile Ile Gln
        435                 440                 445

Ser Gln Leu Pro Ile Gly Thr Leu Lys His Asn Met Thr Tyr Phe Cys
450                 455                 460

Lys Thr His Asn Ser Val Gly Asn Ser Ser Gln Tyr Phe Arg Ala Val
465                 470                 475                 480

Ser Leu Gly Gln Ser Lys Gln Leu Pro Asp Glu Ser Glu Pro Lys Ser
                485                 490                 495

Ser Asp Lys Thr His Thr Cys Pro Pro Cys Pro Ala Pro Glu Leu Leu
            500                 505                 510

Gly Gly Pro Ser Val Phe Leu Phe Pro Pro Lys Pro Lys Asp Thr Leu
        515                 520                 525

Met Ile Ser Arg Thr Pro Glu Val Thr Cys Val Val Val Asp Val Ser
530                 535                 540

His Glu Asp Pro Glu Val Lys Phe Asn Trp Tyr Val Asp Gly Val Glu
545                 550                 555                 560

Val His Asn Ala Lys Thr Lys Pro Arg Glu Glu Gln Tyr Asn Ser Thr
                565                 570                 575

Tyr Arg Val Val Ser Val Leu Thr Val Leu His Gln Asp Trp Leu Asn
            580                 585                 590

Gly Lys Glu Tyr Lys Cys Lys Val Ser Asn Lys Ala Leu Pro Ala Pro
        595                 600                 605

Ile Glu Lys Thr Ile Ser Lys Ala Lys Gly Gln Pro Arg Glu Pro Gln
610                 615                 620

Val Tyr Thr Leu Pro Pro Ser Arg Asp Glu Leu Thr Lys Asn Gln Val
625                 630                 635                 640

Ser Leu Thr Cys Leu Val Lys Gly Phe Tyr Pro Ser Asp Ile Ala Val
                645                 650                 655

Glu Trp Glu Ser Asn Gly Gln Pro Glu Asn Asn Tyr Lys Thr Thr Pro
            660                 665                 670

Pro Val Leu Asp Ser Asp Gly Ser Phe Phe Leu Tyr Ser Lys Leu Thr
        675                 680                 685

Val Asp Lys Ser Arg Trp Gln Gln Gly Asn Val Phe Ser Cys Ser Val
690                 695                 700

Met His Glu Ala Leu His Asn His Tyr Thr Gln Lys Ser Leu Ser Leu
705                 710                 715                 720
```

Ser Pro Gly Lys

<210> SEQ ID NO 8
<211> LENGTH: 719
<212> TYPE: PRT
<213> ORGANISM: Artificial Sequence
<220> FEATURE:
<223> OTHER INFORMATION: mCSF1R-ECD.506-Fc

<400> SEQUENCE: 8

```
Ala Pro Val Ile Glu Pro Ser Gly Pro Glu Leu Val Val Glu Pro Gly
1               5                   10                  15

Glu Thr Val Thr Leu Arg Cys Val Ser Asn Gly Ser Val Glu Trp Asp
            20                  25                  30

Gly Pro Ile Ser Pro Tyr Trp Thr Leu Asp Pro Glu Ser Pro Gly Ser
        35                  40                  45

Thr Leu Thr Thr Arg Asn Ala Thr Phe Lys Asn Thr Gly Thr Tyr Arg
    50                  55                  60

Cys Thr Glu Leu Glu Asp Pro Met Ala Gly Ser Thr Thr Ile His Leu
65                  70                  75                  80

Tyr Val Lys Asp Pro Ala His Ser Trp Asn Leu Leu Ala Gln Glu Val
                85                  90                  95

Thr Val Glu Gly Gln Glu Ala Val Leu Pro Cys Leu Ile Thr Asp
            100                 105                 110

Pro Ala Leu Lys Asp Ser Val Ser Leu Met Arg Glu Gly Gly Arg Gln
        115                 120                 125

Val Leu Arg Lys Thr Val Tyr Phe Phe Ser Pro Trp Arg Gly Phe Ile
    130                 135                 140

Ile Arg Lys Ala Lys Val Leu Asp Ser Asn Thr Tyr Val Cys Lys Thr
145                 150                 155                 160

Met Val Asn Gly Arg Glu Ser Thr Ser Thr Gly Ile Trp Leu Lys Val
                165                 170                 175

Asn Arg Val His Pro Glu Pro Pro Gln Ile Lys Leu Glu Pro Ser Lys
            180                 185                 190

Leu Val Arg Ile Arg Gly Glu Ala Ala Gln Ile Val Cys Ser Ala Thr
        195                 200                 205

Asn Ala Glu Val Gly Phe Asn Val Ile Leu Lys Arg Gly Asp Thr Lys
    210                 215                 220

Leu Glu Ile Pro Leu Asn Ser Asp Phe Gln Asp Asn Tyr Tyr Lys Lys
225                 230                 235                 240

Val Arg Ala Leu Ser Leu Asn Ala Val Asp Phe Gln Asp Ala Gly Ile
                245                 250                 255

Tyr Ser Cys Val Ala Ser Asn Asp Val Gly Thr Arg Thr Ala Thr Met
            260                 265                 270

Asn Phe Gln Val Val Glu Ser Ala Tyr Leu Asn Leu Thr Ser Glu Gln
        275                 280                 285

Ser Leu Leu Gln Glu Val Ser Val Gly Asp Ser Leu Ile Leu Thr Val
    290                 295                 300

His Ala Asp Ala Tyr Pro Ser Ile Gln His Tyr Asn Trp Thr Tyr Leu
305                 310                 315                 320

Gly Pro Phe Phe Glu Asp Gln Arg Lys Leu Glu Phe Ile Thr Gln Arg
                325                 330                 335

Ala Ile Tyr Arg Tyr Thr Phe Lys Leu Phe Leu Asn Arg Val Lys Ala
            340                 345                 350

Ser Glu Ala Gly Gln Tyr Phe Leu Met Ala Gln Asn Lys Ala Gly Trp
        355                 360                 365
```

```
Asn Asn Leu Thr Phe Glu Leu Thr Leu Arg Tyr Pro Pro Glu Val Ser
            370                 375                 380

Val Thr Trp Met Pro Val Asn Gly Ser Asp Val Leu Phe Cys Asp Val
385                 390                 395                 400

Ser Gly Tyr Pro Gln Pro Ser Val Thr Trp Met Glu Cys Arg Gly His
                405                 410                 415

Thr Asp Arg Cys Asp Glu Ala Gln Ala Leu Gln Val Trp Asn Asp Thr
            420                 425                 430

His Pro Glu Val Leu Ser Gln Lys Pro Phe Asp Lys Val Ile Ile Gln
        435                 440                 445

Ser Gln Leu Pro Ile Gly Thr Leu Lys His Asn Met Thr Tyr Phe Cys
    450                 455                 460

Lys Thr His Asn Ser Val Gly Asn Ser Ser Gln Tyr Phe Arg Ala Val
465                 470                 475                 480

Ser Leu Gly Gln Ser Lys Gln Glu Pro Lys Ser Ser Asp Lys Thr His
                485                 490                 495

Thr Cys Pro Pro Cys Pro Ala Pro Glu Leu Leu Gly Gly Pro Ser Val
            500                 505                 510

Phe Leu Phe Pro Pro Lys Pro Lys Asp Thr Leu Met Ile Ser Arg Thr
        515                 520                 525

Pro Glu Val Thr Cys Val Val Val Asp Val Ser His Glu Asp Pro Glu
    530                 535                 540

Val Lys Phe Asn Trp Tyr Val Asp Gly Val Glu Val His Asn Ala Lys
545                 550                 555                 560

Thr Lys Pro Arg Glu Glu Gln Tyr Asn Ser Thr Tyr Arg Val Val Ser
                565                 570                 575

Val Leu Thr Val Leu His Gln Asp Trp Leu Asn Gly Lys Glu Tyr Lys
            580                 585                 590

Cys Lys Val Ser Asn Lys Ala Leu Pro Ala Pro Ile Glu Lys Thr Ile
        595                 600                 605

Ser Lys Ala Lys Gly Gln Pro Arg Glu Pro Gln Val Tyr Thr Leu Pro
    610                 615                 620

Pro Ser Arg Asp Glu Leu Thr Lys Asn Gln Val Ser Leu Thr Cys Leu
625                 630                 635                 640

Val Lys Gly Phe Tyr Pro Ser Asp Ile Ala Val Glu Trp Glu Ser Asn
                645                 650                 655

Gly Gln Pro Glu Asn Asn Tyr Lys Thr Thr Pro Pro Val Leu Asp Ser
            660                 665                 670

Asp Gly Ser Phe Phe Leu Tyr Ser Lys Leu Thr Val Asp Lys Ser Arg
        675                 680                 685

Trp Gln Gln Gly Asn Val Phe Ser Cys Ser Val Met His Glu Ala Leu
    690                 695                 700

His Asn His Tyr Thr Gln Lys Ser Leu Ser Leu Ser Pro Gly Lys
705                 710                 715

<210> SEQ ID NO 9
<211> LENGTH: 19
<212> TYPE: PRT
<213> ORGANISM: Artificial Sequence
<220> FEATURE:
<223> OTHER INFORMATION: hCSF1R signal peptide

<400> SEQUENCE: 9

Met Gly Pro Gly Val Leu Leu Leu Leu Leu Val Ala Thr Ala Trp His
1               5                   10                  15
```

-continued

Gly Gln Gly

<210> SEQ ID NO 10
<211> LENGTH: 19
<212> TYPE: PRT
<213> ORGANISM: Artificial Sequence
<220> FEATURE:
<223> OTHER INFORMATION: mCSF1R signal peptide

<400> SEQUENCE: 10

Met Glu Leu Gly Pro Pro Leu Val Leu Leu Leu Ala Thr Val Trp His
1               5                   10                  15

Gly Gln Gly

<210> SEQ ID NO 11
<211> LENGTH: 512
<212> TYPE: PRT
<213> ORGANISM: Artificial Sequence
<220> FEATURE:
<223> OTHER INFORMATION: hCSF1R-ECD.512 with signal peptide

<400> SEQUENCE: 11

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
        50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
        115                 120                 125

Leu Thr Asp Pro Val Leu Glu Ala Gly Val Ser Leu Val Arg Val Arg
130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
        195                 200                 205

Pro Ala Glu Leu Val Arg Ile Arg Gly Glu Ala Ala Gln Ile Val Cys
210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
        275                 280                 285

Thr Ser Met Phe Phe Arg Val Glu Ser Ala Tyr Leu Asn Leu Ser
    290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
            325                 330                 335

Thr Tyr Leu Gly Pro Phe Ser Asp His Gln Pro Glu Pro Lys Leu Ala
        340                 345                 350

Asn Ala Thr Thr Lys Asp Thr Tyr Arg His Thr Phe Thr Leu Ser Leu
    355                 360                 365

Pro Arg Leu Lys Pro Ser Glu Ala Gly Arg Tyr Ser Phe Leu Ala Arg
370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
            405                 410                 415

Leu Leu Cys Ala Ala Ser Gly Tyr Pro Gln Pro Asn Val Thr Trp Leu
        420                 425                 430

Gln Cys Ser Gly His Thr Asp Arg Cys Asp Glu Ala Gln Val Leu Gln
    435                 440                 445

Val Trp Asp Asp Pro Tyr Pro Glu Val Leu Ser Gln Glu Pro Phe His
450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
            485                 490                 495

Ala Phe Ile Pro Ile Ser Ala Gly Ala His Thr His Pro Pro Asp Glu
        500                 505                 510

<210> SEQ ID NO 12
<211> LENGTH: 506
<212> TYPE: PRT
<213> ORGANISM: Artificial Sequence
<220> FEATURE:
<223> OTHER INFORMATION: hCSF1R-ECD.506 with signal peptide

<400> SEQUENCE: 12

Met Gly Pro Gly Val Leu Leu Leu Leu Leu Val Ala Thr Ala Trp His
1               5                   10                  15

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
        35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
            85                  90                  95

Ile His Leu Tyr Val Lys Asp Pro Ala Arg Pro Trp Asn Val Leu Ala
        100                 105                 110

Gln Glu Val Val Val Phe Glu Asp Gln Asp Ala Leu Leu Pro Cys Leu
    115                 120                 125

Leu Thr Asp Pro Val Leu Glu Ala Gly Val Ser Leu Val Arg Val Arg
130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
            165                 170                 175

Cys Ser Ala Leu Met Gly Gly Arg Lys Val Met Ser Ile Ser Ile Arg
        180                 185                 190

Leu Lys Val Gln Lys Val Ile Pro Gly Pro Pro Ala Leu Thr Leu Val
    195                 200                 205

Pro Ala Glu Leu Val Arg Ile Arg Gly Glu Ala Ala Gln Ile Val Cys
210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
            245                 250                 255

Tyr Gln Lys Val Leu Thr Leu Asn Leu Asp Gln Val Asp Phe Gln His
        260                 265                 270

Ala Gly Asn Tyr Ser Cys Val Ala Ser Asn Val Gln Gly Lys His Ser
    275                 280                 285

Thr Ser Met Phe Phe Arg Val Val Glu Ser Ala Tyr Leu Asn Leu Ser
290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
            325                 330                 335

Thr Tyr Leu Gly Pro Phe Ser Asp His Gln Pro Glu Pro Lys Leu Ala
        340                 345                 350

Asn Ala Thr Thr Lys Asp Thr Tyr Arg His Thr Phe Thr Leu Ser Leu
    355                 360                 365

Pro Arg Leu Lys Pro Ser Glu Ala Gly Arg Tyr Ser Phe Leu Ala Arg
370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
            405                 410                 415

Leu Leu Cys Ala Ala Ser Gly Tyr Pro Gln Pro Asn Val Thr Trp Leu
        420                 425                 430

Gln Cys Ser Gly His Thr Asp Arg Cys Asp Glu Ala Gln Val Leu Gln
    435                 440                 445

Val Trp Asp Asp Pro Tyr Pro Glu Val Leu Ser Gln Glu Pro Phe His
450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
            485                 490                 495

Ala Phe Ile Pro Ile Ser Ala Gly Ala His
        500                 505

<210> SEQ ID NO 13
<211> LENGTH: 511
<212> TYPE: PRT
<213> ORGANISM: Artificial Sequence
<220> FEATURE:
<223> OTHER INFORMATION: mCSF1R-ECD.511 with signal peptide

<400> SEQUENCE: 13

Met Glu Leu Gly Pro Pro Leu Val Leu Leu Leu Ala Thr Val Trp His

-continued

```
  1               5              10              15
Gly Gln Gly Ala Pro Val Ile Glu Pro Ser Gly Pro Glu Leu Val Val
             20                  25                  30

Glu Pro Gly Glu Thr Val Thr Leu Arg Cys Val Ser Asn Gly Ser Val
             35                  40                  45

Glu Trp Asp Gly Pro Ile Ser Pro Tyr Trp Thr Leu Asp Pro Glu Ser
 50                  55                  60

Pro Gly Ser Thr Leu Thr Arg Asn Ala Thr Phe Lys Asn Thr Gly
 65                  70                  75                  80

Thr Tyr Arg Cys Thr Glu Leu Glu Asp Pro Met Ala Gly Ser Thr Thr
                 85                  90                  95

Ile His Leu Tyr Val Lys Asp Pro Ala His Ser Trp Asn Leu Leu Ala
                100                 105                 110

Gln Glu Val Thr Val Val Glu Gly Gln Glu Ala Val Leu Pro Cys Leu
                115                 120                 125

Ile Thr Asp Pro Ala Leu Lys Asp Ser Val Ser Leu Met Arg Glu Gly
                130                 135                 140

Gly Arg Gln Val Leu Arg Lys Thr Val Tyr Phe Phe Ser Pro Trp Arg
145                 150                 155                 160

Gly Phe Ile Ile Arg Lys Ala Lys Val Leu Asp Ser Asn Thr Tyr Val
                165                 170                 175

Cys Lys Thr Met Val Asn Gly Arg Glu Ser Thr Ser Thr Gly Ile Trp
                180                 185                 190

Leu Lys Val Asn Arg Val His Pro Glu Pro Pro Gln Ile Lys Leu Glu
                195                 200                 205

Pro Ser Lys Leu Val Arg Ile Arg Gly Glu Ala Ala Gln Ile Val Cys
210                 215                 220

Ser Ala Thr Asn Ala Glu Val Gly Phe Asn Val Ile Leu Lys Arg Gly
225                 230                 235                 240

Asp Thr Lys Leu Glu Ile Pro Leu Asn Ser Asp Phe Gln Asp Asn Tyr
                245                 250                 255

Tyr Lys Lys Val Arg Ala Leu Ser Leu Asn Ala Val Asp Phe Gln Asp
                260                 265                 270

Ala Gly Ile Tyr Ser Cys Val Ala Ser Asn Asp Val Gly Thr Arg Thr
                275                 280                 285

Ala Thr Met Asn Phe Gln Val Val Glu Ser Ala Tyr Leu Asn Leu Thr
                290                 295                 300

Ser Glu Gln Ser Leu Leu Gln Glu Val Ser Val Gly Asp Ser Leu Ile
305                 310                 315                 320

Leu Thr Val His Ala Asp Ala Tyr Pro Ser Ile Gln His Tyr Asn Trp
                325                 330                 335

Thr Tyr Leu Gly Pro Phe Phe Glu Asp Gln Arg Lys Leu Glu Phe Ile
                340                 345                 350

Thr Gln Arg Ala Ile Tyr Arg Tyr Thr Phe Lys Leu Phe Leu Asn Arg
                355                 360                 365

Val Lys Ala Ser Glu Ala Gly Gln Tyr Phe Leu Met Ala Gln Asn Lys
                370                 375                 380

Ala Gly Trp Asn Asn Leu Thr Phe Glu Leu Thr Leu Arg Tyr Pro Pro
385                 390                 395                 400

Glu Val Ser Val Thr Trp Met Pro Val Asn Gly Ser Asp Val Leu Phe
                405                 410                 415

Cys Asp Val Ser Gly Tyr Pro Gln Pro Ser Val Thr Trp Met Glu Cys
                420                 425                 430
```

-continued

```
Arg Gly His Thr Asp Arg Cys Asp Glu Ala Gln Ala Leu Gln Val Trp
            435                 440                 445

Asn Asp Thr His Pro Glu Val Leu Ser Gln Lys Pro Phe Asp Lys Val
450                 455                 460

Ile Ile Gln Ser Gln Leu Pro Ile Gly Thr Leu Lys His Asn Met Thr
465                 470                 475                 480

Tyr Phe Cys Lys Thr His Asn Ser Val Gly Asn Ser Ser Gln Tyr Phe
                485                 490                 495

Arg Ala Val Ser Leu Gly Gln Ser Lys Gln Leu Pro Asp Glu Ser
            500                 505                 510

<210> SEQ ID NO 14
<211> LENGTH: 506
<212> TYPE: PRT
<213> ORGANISM: Artificial Sequence
<220> FEATURE:
<223> OTHER INFORMATION: mCSF1R-ECD.506 with signal peptide

<400> SEQUENCE: 14

Met Glu Leu Gly Pro Pro Leu Val Leu Leu Leu Ala Thr Val Trp His
1               5                   10                  15

Gly Gln Gly Ala Pro Val Ile Glu Pro Ser Gly Pro Glu Leu Val Val
            20                  25                  30

Glu Pro Gly Glu Thr Val Thr Leu Arg Cys Val Ser Asn Gly Ser Val
        35                  40                  45

Glu Trp Asp Gly Pro Ile Ser Pro Tyr Trp Thr Leu Asp Pro Glu Ser
    50                  55                  60

Pro Gly Ser Thr Leu Thr Thr Arg Asn Ala Thr Phe Lys Asn Thr Gly
65                  70                  75                  80

Thr Tyr Arg Cys Thr Glu Leu Glu Asp Pro Met Ala Gly Ser Thr Thr
                85                  90                  95

Ile His Leu Tyr Val Lys Asp Pro Ala His Ser Trp Asn Leu Leu Ala
            100                 105                 110

Gln Glu Val Thr Val Val Glu Gly Gln Glu Ala Val Leu Pro Cys Leu
        115                 120                 125

Ile Thr Asp Pro Ala Leu Lys Asp Ser Val Ser Leu Met Arg Glu Gly
    130                 135                 140

Gly Arg Gln Val Leu Arg Lys Thr Val Tyr Phe Phe Ser Pro Trp Arg
145                 150                 155                 160

Gly Phe Ile Ile Arg Lys Ala Lys Val Leu Asp Ser Asn Thr Tyr Val
                165                 170                 175

Cys Lys Thr Met Val Asn Gly Arg Glu Ser Thr Ser Thr Gly Ile Trp
            180                 185                 190

Leu Lys Val Asn Arg Val His Pro Glu Pro Pro Gln Ile Lys Leu Glu
        195                 200                 205

Pro Ser Lys Leu Val Arg Ile Arg Gly Glu Ala Ala Gln Ile Val Cys
    210                 215                 220

Ser Ala Thr Asn Ala Glu Val Gly Phe Asn Val Ile Leu Lys Arg Gly
225                 230                 235                 240

Asp Thr Lys Leu Glu Ile Pro Leu Asn Ser Asp Phe Gln Asp Asn Tyr
                245                 250                 255

Tyr Lys Lys Val Arg Ala Leu Ser Leu Asn Ala Val Asp Phe Gln Asp
            260                 265                 270

Ala Gly Ile Tyr Ser Cys Val Ala Ser Asn Asp Val Gly Thr Arg Thr
        275                 280                 285

Ala Thr Met Asn Phe Gln Val Val Glu Ser Ala Tyr Leu Asn Leu Thr
```

```
                   290                 295                 300
Ser Glu Gln Ser Leu Leu Gln Glu Val Ser Val Gly Asp Ser Leu Ile
305                 310                 315                 320

Leu Thr Val His Ala Asp Ala Tyr Pro Ser Ile Gln His Tyr Asn Trp
                325                 330                 335

Thr Tyr Leu Gly Pro Phe Phe Glu Asp Gln Arg Lys Leu Glu Phe Ile
                340                 345                 350

Thr Gln Arg Ala Ile Tyr Arg Tyr Thr Phe Lys Leu Phe Leu Asn Arg
                355                 360                 365

Val Lys Ala Ser Glu Ala Gly Gln Tyr Phe Leu Met Ala Gln Asn Lys
370                 375                 380

Ala Gly Trp Asn Asn Leu Thr Phe Glu Leu Thr Leu Arg Tyr Pro Pro
385                 390                 395                 400

Glu Val Ser Val Thr Trp Met Pro Val Asn Gly Ser Asp Val Leu Phe
                405                 410                 415

Cys Asp Val Ser Gly Tyr Pro Gln Pro Ser Val Thr Trp Met Glu Cys
                420                 425                 430

Arg Gly His Thr Asp Arg Cys Asp Glu Ala Gln Ala Leu Gln Val Trp
                435                 440                 445

Asn Asp Thr His Pro Glu Val Leu Ser Gln Lys Pro Phe Asp Lys Val
450                 455                 460

Ile Ile Gln Ser Gln Leu Pro Ile Gly Thr Leu Lys His Asn Met Thr
465                 470                 475                 480

Tyr Phe Cys Lys Thr His Asn Ser Val Gly Asn Ser Ser Gln Tyr Phe
                485                 490                 495

Arg Ala Val Ser Leu Gly Gln Ser Lys Gln
                500                 505

<210> SEQ ID NO 15
<211> LENGTH: 744
<212> TYPE: PRT
<213> ORGANISM: Artificial Sequence
<220> FEATURE:
<223> OTHER INFORMATION: hCSF1R-ECD.512-Fc with signal peptide

<400> SEQUENCE: 15

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
                35                  40                  45

Glu Trp Asp Gly Pro Pro Ser Pro His Trp Thr Leu Tyr Ser Asp Gly
50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
                100                 105                 110

Gln Glu Val Val Val Phe Glu Asp Gln Asp Ala Leu Leu Pro Cys Leu
                115                 120                 125

Leu Thr Asp Pro Val Leu Glu Ala Gly Val Ser Leu Val Arg Val Arg
                130                 135                 140

Gly Arg Pro Leu Met Arg His Thr Asn Tyr Ser Phe Ser Pro Trp His
145                 150                 155                 160
```

```
Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Ala Leu Thr Leu Val
        195                 200                 205

Pro Ala Glu Leu Val Arg Ile Arg Gly Glu Ala Ala Gln Ile Val Cys
210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
        275                 280                 285

Thr Ser Met Phe Phe Arg Val Val Glu Ser Ala Tyr Leu Asn Leu Ser
290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
        355                 360                 365

Pro Arg Leu Lys Pro Ser Glu Ala Gly Arg Tyr Ser Phe Leu Ala Arg
370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
            500                 505                 510

Glu Pro Lys Ser Ser Asp Lys Thr His Thr Cys Pro Pro Cys Pro Ala
        515                 520                 525

Pro Glu Leu Leu Gly Gly Pro Ser Val Phe Leu Phe Pro Pro Lys Pro
530                 535                 540

Lys Asp Thr Leu Met Ile Ser Arg Thr Pro Glu Val Thr Cys Val Val
545                 550                 555                 560

Val Asp Val Ser His Glu Asp Pro Glu Val Lys Phe Asn Trp Tyr Val
                565                 570                 575

Asp Gly Val Glu Val His Asn Ala Lys Thr Lys Pro Arg Glu Glu Gln
```

```
                    580                 585                 590
Tyr Asn Ser Thr Tyr Arg Val Val Ser Val Leu Thr Val Leu His Gln
                595                 600                 605

Asp Trp Leu Asn Gly Lys Glu Tyr Lys Cys Lys Val Ser Asn Lys Ala
            610                 615                 620

Leu Pro Ala Pro Ile Glu Lys Thr Ile Ser Lys Ala Lys Gly Gln Pro
625                 630                 635                 640

Arg Glu Pro Gln Val Tyr Thr Leu Pro Pro Ser Arg Asp Glu Leu Thr
                645                 650                 655

Lys Asn Gln Val Ser Leu Thr Cys Leu Val Lys Gly Phe Tyr Pro Ser
            660                 665                 670

Asp Ile Ala Val Glu Trp Glu Ser Asn Gly Gln Pro Glu Asn Asn Tyr
675                 680                 685

Lys Thr Thr Pro Pro Val Leu Asp Ser Asp Gly Ser Phe Phe Leu Tyr
                690                 695                 700

Ser Lys Leu Thr Val Asp Lys Ser Arg Trp Gln Gln Gly Asn Val Phe
705                 710                 715                 720

Ser Cys Ser Val Met His Glu Ala Leu His Asn His Tyr Thr Gln Lys
                725                 730                 735

Ser Leu Ser Leu Ser Pro Gly Lys
            740

<210> SEQ ID NO 16
<211> LENGTH: 738
<212> TYPE: PRT
<213> ORGANISM: Artificial Sequence
<220> FEATURE:
<223> OTHER INFORMATION: hCSF1R-ECD.506-Fc with signal peptide

<400> SEQUENCE: 16

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
        115                 120                 125

Leu Thr Asp Pro Val Leu Glu Ala Gly Val Ser Leu Val Arg Val Arg
130                 135                 140

Gly Arg Pro Leu Met Arg His Thr Asn Tyr Ser Phe Ser Pro Trp His
                145                 150                 155             160

Gly Phe Thr Ile His Arg Ala Lys Phe Ile Gln Ser Gln Asp Tyr Gln
            165                 170                 175

Cys Ser Ala Leu Met Gly Gly Arg Lys Val Met Ser Ile Ser Ile Arg
        180                 185                 190

Leu Lys Val Gln Lys Val Ile Pro Gly Pro Pro Ala Leu Thr Leu Val
        195                 200                 205
```

```
Pro Ala Glu Leu Val Arg Ile Arg Gly Glu Ala Gln Ile Val Cys
    210                 215                 220
Ser Ala Ser Ser Val Asp Val Asn Phe Asp Val Phe Leu Gln His Asn
225                 230                 235                 240
Asn Thr Lys Leu Ala Ile Pro Gln Gln Ser Asp Phe His Asn Asn Arg
                    245                 250                 255
Tyr Gln Lys Val Leu Thr Leu Asn Leu Asp Gln Val Asp Phe Gln His
                260                 265                 270
Ala Gly Asn Tyr Ser Cys Val Ala Ser Asn Val Gln Gly Lys His Ser
                275                 280                 285
Thr Ser Met Phe Phe Arg Val Val Glu Ser Ala Tyr Leu Asn Leu Ser
    290                 295                 300
Ser Glu Gln Asn Leu Ile Gln Glu Val Thr Val Gly Glu Gly Leu Asn
305                 310                 315                 320
Leu Lys Val Met Val Glu Ala Tyr Pro Gly Leu Gln Gly Phe Asn Trp
                    325                 330                 335
Thr Tyr Leu Gly Pro Phe Ser Asp His Gln Pro Glu Pro Lys Leu Ala
                340                 345                 350
Asn Ala Thr Thr Lys Asp Thr Tyr Arg His Thr Phe Thr Leu Ser Leu
                355                 360                 365
Pro Arg Leu Lys Pro Ser Glu Ala Gly Arg Tyr Ser Phe Leu Ala Arg
    370                 375                 380
Asn Pro Gly Gly Trp Arg Ala Leu Thr Phe Glu Leu Thr Leu Arg Tyr
385                 390                 395                 400
Pro Pro Glu Val Ser Val Ile Trp Thr Phe Ile Asn Gly Ser Gly Thr
                    405                 410                 415
Leu Leu Cys Ala Ala Ser Gly Tyr Pro Gln Pro Asn Val Thr Trp Leu
                420                 425                 430
Gln Cys Ser Gly His Thr Asp Arg Cys Asp Glu Ala Gln Val Leu Gln
                435                 440                 445
Val Trp Asp Asp Pro Tyr Pro Glu Val Leu Ser Gln Glu Pro Phe His
    450                 455                 460
Lys Val Thr Val Gln Ser Leu Leu Thr Val Glu Thr Leu Glu His Asn
465                 470                 475                 480
Gln Thr Tyr Glu Cys Arg Ala His Asn Ser Val Gly Ser Gly Ser Trp
                    485                 490                 495
Ala Phe Ile Pro Ile Ser Ala Gly Ala His Glu Pro Lys Ser Ser Asp
                500                 505                 510
Lys Thr His Thr Cys Pro Pro Cys Pro Ala Pro Glu Leu Leu Gly Gly
                515                 520                 525
Pro Ser Val Phe Leu Phe Pro Pro Lys Pro Lys Asp Thr Leu Met Ile
    530                 535                 540
Ser Arg Thr Pro Glu Val Thr Cys Val Val Val Asp Val Ser His Glu
545                 550                 555                 560
Asp Pro Glu Val Lys Phe Asn Trp Tyr Val Asp Gly Val Glu Val His
                    565                 570                 575
Asn Ala Lys Thr Lys Pro Arg Glu Glu Gln Tyr Asn Ser Thr Tyr Arg
                580                 585                 590
Val Val Ser Val Leu Thr Val Leu His Gln Asp Trp Leu Asn Gly Lys
                595                 600                 605
Glu Tyr Lys Cys Lys Val Ser Asn Lys Ala Leu Pro Ala Pro Ile Glu
    610                 615                 620
Lys Thr Ile Ser Lys Ala Lys Gly Gln Pro Arg Glu Pro Gln Val Tyr
```

```
                    625                 630                 635                 640
Thr Leu Pro Pro Ser Arg Asp Glu Leu Thr Lys Asn Gln Val Ser Leu
                645                 650                 655

Thr Cys Leu Val Lys Gly Phe Tyr Pro Ser Asp Ile Ala Val Glu Trp
                660                 665                 670

Glu Ser Asn Gly Gln Pro Glu Asn Asn Tyr Lys Thr Thr Pro Pro Val
                675                 680                 685

Leu Asp Ser Asp Gly Ser Phe Phe Leu Tyr Ser Lys Leu Thr Val Asp
                690                 695                 700

Lys Ser Arg Trp Gln Gln Gly Asn Val Phe Ser Cys Ser Val Met His
705                 710                 715                 720

Glu Ala Leu His Asn His Tyr Thr Gln Lys Ser Leu Ser Leu Ser Pro
                725                 730                 735

Gly Lys

<210> SEQ ID NO 17
<211> LENGTH: 743
<212> TYPE: PRT
<213> ORGANISM: Artificial Sequence
<220> FEATURE:
<223> OTHER INFORMATION: mCSF1R-ECD.511-Fc with signal peptide

<400> SEQUENCE: 17

Met Glu Leu Gly Pro Pro Leu Val Leu Leu Leu Ala Thr Val Trp His
1               5                   10                  15

Gly Gln Gly Ala Pro Val Ile Glu Pro Ser Gly Pro Glu Leu Val Val
                20                  25                  30

Glu Pro Gly Glu Thr Val Thr Leu Arg Cys Val Ser Asn Gly Ser Val
                35                  40                  45

Glu Trp Asp Gly Pro Ile Ser Pro Tyr Trp Thr Leu Asp Pro Glu Ser
50                  55                  60

Pro Gly Ser Thr Leu Thr Thr Arg Asn Ala Thr Phe Lys Asn Thr Gly
65                  70                  75                  80

Thr Tyr Arg Cys Thr Glu Leu Glu Asp Pro Met Ala Gly Ser Thr Thr
                85                  90                  95

Ile His Leu Tyr Val Lys Asp Pro Ala His Ser Trp Asn Leu Leu Ala
                100                 105                 110

Gln Glu Val Thr Val Val Glu Gly Gln Glu Ala Val Leu Pro Cys Leu
                115                 120                 125

Ile Thr Asp Pro Ala Leu Lys Asp Ser Val Ser Leu Met Arg Glu Gly
                130                 135                 140

Gly Arg Gln Val Leu Arg Lys Thr Val Tyr Phe Phe Ser Pro Trp Arg
145                 150                 155                 160

Gly Phe Ile Ile Arg Lys Ala Lys Val Leu Asp Ser Asn Thr Tyr Val
                165                 170                 175

Cys Lys Thr Met Val Asn Gly Arg Glu Ser Thr Ser Thr Gly Ile Trp
                180                 185                 190

Leu Lys Val Asn Arg Val His Pro Glu Pro Pro Gln Ile Lys Leu Glu
                195                 200                 205

Pro Ser Lys Leu Val Arg Ile Arg Gly Glu Ala Ala Gln Ile Val Cys
                210                 215                 220

Ser Ala Thr Asn Ala Glu Val Gly Phe Asn Val Ile Leu Lys Arg Gly
225                 230                 235                 240

Asp Thr Lys Leu Glu Ile Pro Leu Asn Ser Asp Phe Gln Asp Asn Tyr
                245                 250                 255
```

-continued

```
Tyr Lys Lys Val Arg Ala Leu Ser Leu Asn Ala Val Asp Phe Gln Asp
        260                 265                 270

Ala Gly Ile Tyr Ser Cys Val Ala Ser Asn Asp Val Gly Thr Arg Thr
            275                 280                 285

Ala Thr Met Asn Phe Gln Val Val Glu Ser Ala Tyr Leu Asn Leu Thr
        290                 295                 300

Ser Glu Gln Ser Leu Leu Gln Glu Val Ser Val Gly Asp Ser Leu Ile
305                 310                 315                 320

Leu Thr Val His Ala Asp Ala Tyr Pro Ser Ile Gln His Tyr Asn Trp
                325                 330                 335

Thr Tyr Leu Gly Pro Phe Phe Glu Asp Gln Arg Lys Leu Glu Phe Ile
            340                 345                 350

Thr Gln Arg Ala Ile Tyr Arg Tyr Thr Phe Lys Leu Phe Leu Asn Arg
        355                 360                 365

Val Lys Ala Ser Glu Ala Gly Gln Tyr Phe Leu Met Ala Gln Asn Lys
    370                 375                 380

Ala Gly Trp Asn Asn Leu Thr Phe Glu Leu Thr Leu Arg Tyr Pro Pro
385                 390                 395                 400

Glu Val Ser Val Thr Trp Met Pro Val Asn Gly Ser Asp Val Leu Phe
                405                 410                 415

Cys Asp Val Ser Gly Tyr Pro Gln Pro Ser Val Thr Trp Met Glu Cys
            420                 425                 430

Arg Gly His Thr Asp Arg Cys Asp Glu Ala Gln Ala Leu Gln Val Trp
        435                 440                 445

Asn Asp Thr His Pro Glu Val Leu Ser Gln Lys Pro Phe Asp Lys Val
    450                 455                 460

Ile Ile Gln Ser Gln Leu Pro Ile Gly Thr Leu Lys His Asn Met Thr
465                 470                 475                 480

Tyr Phe Cys Lys Thr His Asn Ser Val Gly Asn Ser Ser Gln Tyr Phe
                485                 490                 495

Arg Ala Val Ser Leu Gly Gln Ser Lys Gln Leu Pro Asp Glu Ser Glu
            500                 505                 510

Pro Lys Ser Ser Asp Lys Thr His Thr Cys Pro Pro Cys Pro Ala Pro
        515                 520                 525

Glu Leu Leu Gly Gly Pro Ser Val Phe Leu Phe Pro Pro Lys Pro Lys
    530                 535                 540

Asp Thr Leu Met Ile Ser Arg Thr Pro Glu Val Thr Cys Val Val Val
545                 550                 555                 560

Asp Val Ser His Glu Asp Pro Glu Val Lys Phe Asn Trp Tyr Val Asp
                565                 570                 575

Gly Val Glu Val His Asn Ala Lys Thr Lys Pro Arg Glu Glu Gln Tyr
            580                 585                 590

Asn Ser Thr Tyr Arg Val Val Ser Val Leu Thr Val Leu His Gln Asp
        595                 600                 605

Trp Leu Asn Gly Lys Glu Tyr Lys Cys Lys Val Ser Asn Lys Ala Leu
    610                 615                 620

Pro Ala Pro Ile Glu Lys Thr Ile Ser Lys Ala Lys Gly Gln Pro Arg
625                 630                 635                 640

Glu Pro Gln Val Tyr Thr Leu Pro Pro Ser Arg Asp Glu Leu Thr Lys
                645                 650                 655

Asn Gln Val Ser Leu Thr Cys Leu Val Lys Gly Phe Tyr Pro Ser Asp
            660                 665                 670

Ile Ala Val Glu Trp Glu Ser Asn Gly Gln Pro Glu Asn Asn Tyr Lys
        675                 680                 685
```

Thr Thr Pro Pro Val Leu Asp Ser Asp Gly Ser Phe Phe Leu Tyr Ser
            690                 695                 700

Lys Leu Thr Val Asp Lys Ser Arg Trp Gln Gln Gly Asn Val Phe Ser
705                 710                 715                 720

Cys Ser Val Met His Glu Ala Leu His Asn His Tyr Thr Gln Lys Ser
                725                 730                 735

Leu Ser Leu Ser Pro Gly Lys
            740

<210> SEQ ID NO 18
<211> LENGTH: 738
<212> TYPE: PRT
<213> ORGANISM: Artificial Sequence
<220> FEATURE:
<223> OTHER INFORMATION: mCSF1R-ECD.506-Fc with signal peptide

<400> SEQUENCE: 18

Met Glu Leu Gly Pro Pro Leu Val Leu Leu Leu Ala Thr Val Trp His
1               5                   10                  15

Gly Gln Gly Ala Pro Val Ile Glu Pro Ser Gly Pro Glu Leu Val Val
            20                  25                  30

Glu Pro Gly Glu Thr Val Thr Leu Arg Cys Val Ser Asn Gly Ser Val
        35                  40                  45

Glu Trp Asp Gly Pro Ile Ser Pro Tyr Trp Thr Leu Asp Pro Glu Ser
    50                  55                  60

Pro Gly Ser Thr Leu Thr Thr Arg Asn Ala Thr Phe Lys Asn Thr Gly
65                  70                  75                  80

Thr Tyr Arg Cys Thr Glu Leu Glu Asp Pro Met Ala Gly Ser Thr Thr
                85                  90                  95

Ile His Leu Tyr Val Lys Asp Pro Ala His Ser Trp Asn Leu Leu Ala
            100                 105                 110

Gln Glu Val Thr Val Val Glu Gly Gln Glu Ala Val Leu Pro Cys Leu
        115                 120                 125

Ile Thr Asp Pro Ala Leu Lys Asp Ser Val Ser Leu Met Arg Glu Gly
    130                 135                 140

Gly Arg Gln Val Leu Arg Lys Thr Val Tyr Phe Phe Ser Pro Trp Arg
145                 150                 155                 160

Gly Phe Ile Ile Arg Lys Ala Lys Val Leu Asp Ser Asn Thr Tyr Val
                165                 170                 175

Cys Lys Thr Met Val Asn Gly Arg Glu Ser Thr Ser Thr Gly Ile Trp
            180                 185                 190

Leu Lys Val Asn Arg Val His Pro Glu Pro Pro Gln Ile Lys Leu Glu
        195                 200                 205

Pro Ser Lys Leu Val Arg Ile Arg Gly Glu Ala Ala Gln Ile Val Cys
    210                 215                 220

Ser Ala Thr Asn Ala Glu Val Gly Phe Asn Val Ile Leu Lys Arg Gly
225                 230                 235                 240

Asp Thr Lys Leu Glu Ile Pro Leu Asn Ser Asp Phe Gln Asp Asn Tyr
                245                 250                 255

Tyr Lys Lys Val Arg Ala Leu Ser Leu Asn Ala Val Asp Phe Gln Asp
            260                 265                 270

Ala Gly Ile Tyr Ser Cys Val Ala Ser Asn Asp Val Gly Thr Arg Thr
        275                 280                 285

Ala Thr Met Asn Phe Gln Val Val Glu Ser Ala Tyr Leu Asn Leu Thr
    290                 295                 300

```
Ser Glu Gln Ser Leu Leu Gln Glu Val Ser Val Gly Asp Ser Leu Ile
305                 310                 315                 320

Leu Thr Val His Ala Asp Ala Tyr Pro Ser Ile Gln His Tyr Asn Trp
                325                 330                 335

Thr Tyr Leu Gly Pro Phe Phe Glu Asp Gln Arg Lys Leu Glu Phe Ile
            340                 345                 350

Thr Gln Arg Ala Ile Tyr Arg Tyr Thr Phe Lys Leu Phe Leu Asn Arg
        355                 360                 365

Val Lys Ala Ser Glu Ala Gly Gln Tyr Phe Leu Met Ala Gln Asn Lys
    370                 375                 380

Ala Gly Trp Asn Leu Thr Phe Glu Leu Thr Leu Arg Tyr Pro Pro
385                 390                 395                 400

Glu Val Ser Val Thr Trp Met Pro Val Asn Gly Ser Asp Val Leu Phe
                405                 410                 415

Cys Asp Val Ser Gly Tyr Pro Gln Pro Ser Val Thr Trp Met Glu Cys
                420                 425                 430

Arg Gly His Thr Asp Arg Cys Asp Glu Ala Gln Ala Leu Gln Val Trp
            435                 440                 445

Asn Asp Thr His Pro Glu Val Leu Ser Gln Lys Pro Phe Asp Lys Val
450                 455                 460

Ile Ile Gln Ser Gln Leu Pro Ile Gly Thr Leu Lys His Asn Met Thr
465                 470                 475                 480

Tyr Phe Cys Lys Thr His Asn Ser Val Gly Asn Ser Ser Gln Tyr Phe
                485                 490                 495

Arg Ala Val Ser Leu Gly Gln Ser Lys Gln Pro Lys Ser Ser Asp
                500                 505                 510

Lys Thr His Thr Cys Pro Pro Cys Pro Ala Pro Glu Leu Leu Gly Gly
            515                 520                 525

Pro Ser Val Phe Leu Phe Pro Pro Lys Pro Lys Asp Thr Leu Met Ile
        530                 535                 540

Ser Arg Thr Pro Glu Val Thr Cys Val Val Val Asp Val Ser His Glu
545                 550                 555                 560

Asp Pro Glu Val Lys Phe Asn Trp Tyr Val Asp Gly Val Glu Val His
                565                 570                 575

Asn Ala Lys Thr Lys Pro Arg Glu Glu Gln Tyr Asn Ser Thr Tyr Arg
            580                 585                 590

Val Val Ser Val Leu Thr Val Leu His Gln Asp Trp Leu Asn Gly Lys
        595                 600                 605

Glu Tyr Lys Cys Lys Val Ser Asn Lys Ala Leu Pro Ala Pro Ile Glu
    610                 615                 620

Lys Thr Ile Ser Lys Ala Lys Gly Gln Pro Arg Glu Pro Gln Val Tyr
625                 630                 635                 640

Thr Leu Pro Pro Ser Arg Asp Glu Leu Thr Lys Asn Gln Val Ser Leu
                645                 650                 655

Thr Cys Leu Val Lys Gly Phe Tyr Pro Ser Asp Ile Ala Val Glu Trp
            660                 665                 670

Glu Ser Asn Gly Gln Pro Glu Asn Asn Tyr Lys Thr Thr Pro Pro Val
        675                 680                 685

Leu Asp Ser Asp Gly Ser Phe Phe Leu Tyr Ser Lys Leu Thr Val Asp
    690                 695                 700

Lys Ser Arg Trp Gln Gln Gly Asn Val Phe Ser Cys Ser Val Met His
705                 710                 715                 720

Glu Ala Leu His Asn His Tyr Thr Gln Lys Ser Leu Ser Leu Ser Pro
                725                 730                 735
```

<210> SEQ ID NO 19
<211> LENGTH: 232
<212> TYPE: PRT
<213> ORGANISM: Artificial Sequence
<220> FEATURE:
<223> OTHER INFORMATION: Fc C237S

<400> SEQUENCE: 19

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 20
<211> LENGTH: 228
<212> TYPE: PRT
<213> ORGANISM: Artificial Sequence
<220> FEATURE:
<223> OTHER INFORMATION: Exemplary Fc #1

<400> SEQUENCE: 20

```
Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Gln Phe Asn Trp Tyr Val Asp Gly Val Glu
    50                  55                  60
```

```
Val His Asn Ala Lys Thr Lys Pro Arg Glu Glu Gln Phe Asn Ser Thr
 65                  70                  75                  80

Phe Arg Val Val Ser Val Leu Thr Val Val His Gln Asp Trp Leu Asn
                 85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 21
<211> LENGTH: 229
<212> TYPE: PRT
<213> ORGANISM: Artificial Sequence
<220> FEATURE:
<223> OTHER INFORMATION: Exemplary Fc #2

<400> SEQUENCE: 21

Glu Ser Lys Tyr Gly Pro Pro Cys Pro Ser Cys Pro Ala Pro Glu Phe
  1               5                  10                  15

Leu Gly Gly Pro Ser Val Phe Leu Phe Pro Pro Lys Pro Lys Asp Thr
                 20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
```

```
        195                 200                 205
Val Met His Glu Ala Leu His Asn His Tyr Thr Gln Lys Ser Leu Ser
210                 215                 220

Leu Ser Leu Gly Lys
225

<210> SEQ ID NO 22
<211> LENGTH: 953
<212> TYPE: PRT
<213> ORGANISM: Artificial Sequence
<220> FEATURE:
<223> OTHER INFORMATION: hCSF1R (full-length, no signal peptide)

<400> SEQUENCE: 22

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
        35                  40                  45

Ile Leu Ser Thr Asn Asn Ala Thr Phe Gln Asn Thr Gly Thr Tyr Arg
    50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
    130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
    210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
        275                 280                 285

Asn Leu Ile Gln Glu Val Thr Val Gly Glu Gly Leu Asn Leu Lys Val
    290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335
```

```
Thr Lys Asp Thr Tyr Arg His Thr Phe Thr Leu Ser Leu Pro Arg Leu
            340                 345                 350

Lys Pro Ser Glu Ala Gly Arg Tyr Ser Phe Leu Ala Arg Asn Pro Gly
            355                 360                 365

Gly Trp Arg Ala Leu Thr Phe Glu Leu Thr Leu Arg Tyr Pro Pro Glu
370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
            405                 410                 415

Gly His Thr Asp Arg Cys Asp Glu Ala Gln Val Leu Gln Val Trp Asp
            420                 425                 430

Asp Pro Tyr Pro Glu Val Leu Ser Gln Glu Pro Phe His Lys Val Thr
            435                 440                 445

Val Gln Ser Leu Leu Thr Val Glu Thr Leu Glu His Asn Gln Thr Tyr
450                 455                 460

Glu Cys Arg Ala His Asn Ser Val Gly Ser Gly Ser Trp Ala Phe Ile
465                 470                 475                 480

Pro Ile Ser Ala Gly Ala His Thr His Pro Pro Asp Glu Phe Leu Phe
            485                 490                 495

Thr Pro Val Val Val Ala Cys Met Ser Ile Met Ala Leu Leu Leu Leu
            500                 505                 510

Leu Leu Leu Leu Leu Leu Tyr Lys Tyr Lys Gln Lys Pro Lys Tyr Gln
            515                 520                 525

Val Arg Trp Lys Ile Ile Glu Ser Tyr Glu Gly Asn Ser Tyr Thr Phe
530                 535                 540

Ile Asp Pro Thr Gln Leu Pro Tyr Asn Glu Lys Trp Glu Phe Pro Arg
545                 550                 555                 560

Asn Asn Leu Gln Phe Gly Lys Thr Leu Gly Ala Gly Ala Phe Gly Lys
            565                 570                 575

Val Val Glu Ala Thr Ala Phe Gly Leu Gly Lys Glu Asp Ala Val Leu
            580                 585                 590

Lys Val Ala Val Lys Met Leu Lys Ser Thr Ala His Ala Asp Glu Lys
            595                 600                 605

Glu Ala Leu Met Ser Glu Leu Lys Ile Met Ser His Leu Gly Gln His
            610                 615                 620

Glu Asn Ile Val Asn Leu Leu Gly Ala Cys Thr His Gly Gly Pro Val
625                 630                 635                 640

Leu Val Ile Thr Glu Tyr Cys Cys Tyr Gly Asp Leu Leu Asn Phe Leu
            645                 650                 655

Arg Arg Lys Ala Glu Ala Met Leu Gly Pro Ser Leu Ser Pro Gly Gln
            660                 665                 670

Asp Pro Glu Gly Gly Val Asp Tyr Lys Asn Ile His Leu Glu Lys Lys
            675                 680                 685

Tyr Val Arg Arg Asp Ser Gly Phe Ser Ser Gln Gly Val Asp Thr Tyr
            690                 695                 700

Val Glu Met Arg Pro Val Ser Thr Ser Ser Asn Asp Ser Phe Ser Glu
705                 710                 715                 720

Gln Asp Leu Asp Lys Glu Asp Gly Arg Pro Leu Glu Leu Arg Asp Leu
            725                 730                 735

Leu His Phe Ser Ser Gln Val Ala Gln Gly Met Ala Phe Leu Ala Ser
            740                 745                 750

Lys Asn Cys Ile His Arg Asp Val Ala Ala Arg Asn Val Leu Leu Thr
```

```
                    755                 760                 765
Asn Gly His Val Ala Lys Ile Gly Asp Phe Gly Leu Ala Arg Asp Ile
770                 775                 780

Met Asn Asp Ser Asn Tyr Ile Val Lys Gly Asn Ala Arg Leu Pro Val
785                 790                 795                 800

Lys Trp Met Ala Pro Glu Ser Ile Phe Asp Cys Val Tyr Thr Val Gln
                805                 810                 815

Ser Asp Val Trp Ser Tyr Gly Ile Leu Leu Trp Glu Ile Phe Ser Leu
                820                 825                 830

Gly Leu Asn Pro Tyr Pro Gly Ile Leu Val Asn Ser Lys Phe Tyr Lys
                835                 840                 845

Leu Val Lys Asp Gly Tyr Gln Met Ala Gln Pro Ala Phe Ala Pro Lys
850                 855                 860

Asn Ile Tyr Ser Ile Met Gln Ala Cys Trp Ala Leu Glu Pro Thr His
865                 870                 875                 880

Arg Pro Thr Phe Gln Gln Ile Cys Ser Phe Leu Gln Glu Gln Ala Gln
                885                 890                 895

Glu Asp Arg Arg Glu Arg Asp Tyr Thr Asn Leu Pro Ser Ser Ser Arg
                900                 905                 910

Ser Gly Gly Ser Gly Ser Ser Ser Glu Leu Glu Glu Glu Ser Ser
                915                 920                 925

Ser Glu His Leu Thr Cys Cys Glu Gln Gly Asp Ile Ala Gln Pro Leu
                930                 935                 940

Leu Gln Pro Asn Asn Tyr Gln Phe Cys
945                 950

<210> SEQ ID NO 23
<211> LENGTH: 972
<212> TYPE: PRT
<213> ORGANISM: Artificial Sequence
<220> FEATURE:
<223> OTHER INFORMATION: hCSF1R (full-length, + signal peptide)

<400> SEQUENCE: 23

Met Gly Pro Gly Val Leu Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
                35                  40                  45

Glu Trp Asp Gly Pro Pro Ser Pro His Trp Thr Leu Tyr Ser Asp Gly
            50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
                100                 105                 110

Gln Glu Val Val Val Phe Glu Asp Gln Asp Ala Leu Leu Pro Cys Leu
                115                 120                 125

Leu Thr Asp Pro Val Leu Glu Ala Gly Val Ser Leu Val Arg Val Arg
130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175
```

```
Cys Ser Ala Leu Met Gly Gly Arg Lys Val Met Ser Ile Ser Ile Arg
            180                 185                 190

Leu Lys Val Gln Lys Val Ile Pro Gly Pro Ala Leu Thr Leu Val
        195                 200                 205

Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
                275                 280                 285

Thr Ser Met Phe Phe Arg Val Val Glu Ser Ala Tyr Leu Asn Leu Ser
        290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
                355                 360                 365

Pro Arg Leu Lys Pro Ser Glu Ala Gly Arg Tyr Ser Phe Leu Ala Arg
    370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
    450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
            500                 505                 510

Phe Leu Phe Thr Pro Val Val Ala Cys Met Ser Ile Met Ala Leu
        515                 520                 525

Leu Leu Leu Leu Leu Leu Leu Leu Tyr Lys Tyr Lys Gln Lys Pro
    530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
            580                 585                 590

Phe Gly Lys Val Val Glu Ala Thr Ala Phe Gly Leu Gly Lys Glu Asp
```

```
                    595                 600                 605
Ala Val Leu Lys Val Ala Val Lys Met Leu Lys Ser Thr Ala His Ala
610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                    645                 650                 655

Gly Pro Val Leu Val Ile Thr Glu Tyr Cys Cys Tyr Gly Asp Leu Leu
                660                 665                 670

Asn Phe Leu Arg Arg Lys Ala Glu Ala Met Leu Gly Pro Ser Leu Ser
            675                 680                 685

Pro Gly Gln Asp Pro Glu Gly Gly Val Asp Tyr Lys Asn Ile His Leu
690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
                740                 745                 750

Arg Asp Leu Leu His Phe Ser Ser Gln Val Ala Gln Gly Met Ala Phe
            755                 760                 765

Leu Ala Ser Lys Asn Cys Ile His Arg Asp Val Ala Ala Arg Asn Val
770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
                820                 825                 830

Thr Val Gln Ser Asp Val Trp Ser Tyr Gly Ile Leu Leu Trp Glu Ile
            835                 840                 845

Phe Ser Leu Gly Leu Asn Pro Tyr Pro Gly Ile Leu Val Asn Ser Lys
850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Phe Leu Gln Glu
                900                 905                 910

Gln Ala Gln Glu Asp Arg Arg Glu Arg Asp Tyr Thr Asn Leu Pro Ser
            915                 920                 925

Ser Ser Arg Ser Gly Gly Ser Gly Ser Ser Ser Glu Leu Glu Glu
930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
                965                 970

<210> SEQ ID NO 24
<211> LENGTH: 958
<212> TYPE: PRT
<213> ORGANISM: Artificial Sequence
<220> FEATURE:
<223> OTHER INFORMATION: mCSF1R (full-length, no signal peptide)

<400> SEQUENCE: 24
```

```
Ala Pro Val Ile Glu Pro Ser Gly Pro Glu Leu Val Val Glu Pro Gly
1               5                   10                  15

Glu Thr Val Thr Leu Arg Cys Val Ser Asn Gly Ser Val Glu Trp Asp
            20                  25                  30

Gly Pro Ile Ser Pro Tyr Trp Thr Leu Asp Pro Glu Pro Gly Ser
            35                  40                  45

Thr Leu Thr Thr Arg Asn Ala Thr Phe Lys Asn Thr Gly Thr Tyr Arg
        50                  55                  60

Cys Thr Glu Leu Glu Asp Pro Met Ala Gly Ser Thr Thr Ile His Leu
65                  70                  75                  80

Tyr Val Lys Asp Pro Ala His Ser Trp Asn Leu Leu Ala Gln Glu Val
                85                  90                  95

Thr Val Val Glu Gly Gln Glu Ala Val Leu Pro Cys Leu Ile Thr Asp
                100                 105                 110

Pro Ala Leu Lys Asp Ser Val Ser Leu Met Arg Glu Gly Gly Arg Gln
            115                 120                 125

Val Leu Arg Lys Thr Val Tyr Phe Phe Ser Pro Trp Arg Gly Phe Ile
    130                 135                 140

Ile Arg Lys Ala Lys Val Leu Asp Ser Asn Thr Tyr Val Cys Lys Thr
145                 150                 155                 160

Met Val Asn Gly Arg Glu Ser Thr Ser Thr Gly Ile Trp Leu Lys Val
                165                 170                 175

Asn Arg Val His Pro Glu Pro Pro Gln Ile Lys Leu Glu Pro Ser Lys
            180                 185                 190

Leu Val Arg Ile Arg Gly Glu Ala Ala Gln Ile Val Cys Ser Ala Thr
        195                 200                 205

Asn Ala Glu Val Gly Phe Asn Val Ile Leu Lys Arg Gly Asp Thr Lys
210                 215                 220

Leu Glu Ile Pro Leu Asn Ser Asp Phe Gln Asp Asn Tyr Tyr Lys Lys
225                 230                 235                 240

Val Arg Ala Leu Ser Leu Asn Ala Val Asp Phe Gln Asp Ala Gly Ile
                245                 250                 255

Tyr Ser Cys Val Ala Ser Asn Asp Val Gly Thr Arg Thr Ala Thr Met
                260                 265                 270

Asn Phe Gln Val Val Glu Ser Ala Tyr Leu Asn Leu Thr Ser Glu Gln
            275                 280                 285

Ser Leu Leu Gln Glu Val Ser Val Gly Asp Ser Leu Ile Leu Thr Val
    290                 295                 300

His Ala Asp Ala Tyr Pro Ser Ile Gln His Tyr Asn Trp Thr Tyr Leu
305                 310                 315                 320

Gly Pro Phe Phe Glu Asp Gln Arg Lys Leu Glu Phe Ile Thr Gln Arg
                325                 330                 335

Ala Ile Tyr Arg Tyr Thr Phe Lys Leu Phe Leu Asn Arg Val Lys Ala
            340                 345                 350

Ser Glu Ala Gly Gln Tyr Phe Leu Met Ala Gln Asn Lys Ala Gly Trp
        355                 360                 365

Asn Asn Leu Thr Phe Glu Leu Thr Leu Arg Tyr Pro Pro Glu Val Ser
    370                 375                 380

Val Thr Trp Met Pro Val Asn Gly Ser Asp Val Leu Phe Cys Asp Val
385                 390                 395                 400

Ser Gly Tyr Pro Gln Pro Ser Val Thr Trp Met Glu Cys Arg Gly His
                405                 410                 415

Thr Asp Arg Cys Asp Glu Ala Gln Ala Leu Gln Val Trp Asn Asp Thr
```

-continued

```
                420             425             430
His Pro Glu Val Leu Ser Gln Lys Pro Phe Asp Lys Val Ile Ile Gln
            435                 440                 445
Ser Gln Leu Pro Ile Gly Thr Leu Lys His Asn Met Thr Tyr Phe Cys
        450                 455                 460
Lys Thr His Asn Ser Val Gly Asn Ser Ser Gln Tyr Phe Arg Ala Val
465                 470                 475                 480
Ser Leu Gly Gln Ser Lys Gln Leu Pro Asp Glu Ser Leu Phe Thr Pro
                485                 490                 495
Val Val Val Ala Cys Met Ser Val Met Ser Leu Leu Val Leu Leu Leu
            500                 505                 510
Leu Leu Leu Leu Tyr Lys Tyr Lys Gln Lys Pro Lys Tyr Gln Val Arg
        515                 520                 525
Trp Lys Ile Ile Glu Arg Tyr Glu Gly Asn Ser Tyr Thr Phe Ile Asp
        530                 535                 540
Pro Thr Gln Leu Pro Tyr Asn Glu Lys Trp Glu Phe Pro Arg Asn Asn
545                 550                 555                 560
Leu Gln Phe Gly Lys Thr Leu Gly Ala Gly Ala Phe Gly Lys Val Val
                565                 570                 575
Glu Ala Thr Ala Phe Gly Leu Gly Lys Glu Asp Ala Val Leu Lys Val
            580                 585                 590
Ala Val Lys Met Leu Lys Ser Thr Ala His Ala Asp Glu Lys Glu Ala
        595                 600                 605
Leu Met Ser Glu Leu Lys Ile Met Ser His Leu Gly Gln His Glu Asn
        610                 615                 620
Ile Val Asn Leu Leu Gly Ala Cys Thr His Gly Gly Pro Val Leu Val
625                 630                 635                 640
Ile Thr Glu Tyr Cys Cys Tyr Gly Asp Leu Leu Asn Phe Leu Arg Arg
                645                 650                 655
Lys Ala Glu Ala Met Leu Gly Pro Ser Leu Ser Pro Gly Gln Asp Ser
            660                 665                 670
Glu Gly Asp Ser Ser Tyr Lys Asn Ile His Leu Glu Lys Lys Tyr Val
        675                 680                 685
Arg Arg Asp Ser Gly Phe Ser Ser Gln Gly Val Asp Thr Tyr Val Glu
        690                 695                 700
Met Arg Pro Val Ser Thr Ser Ser Asp Ser Phe Phe Lys Gln Asp
705                 710                 715                 720
Leu Asp Lys Glu Ala Ser Arg Pro Leu Glu Leu Trp Asp Leu Leu His
                725                 730                 735
Phe Ser Ser Gln Val Ala Gln Gly Met Ala Phe Leu Ala Ser Lys Asn
            740                 745                 750
Cys Ile His Arg Asp Val Ala Ala Arg Asn Val Leu Leu Thr Ser Gly
        755                 760                 765
His Val Ala Lys Ile Gly Asp Phe Gly Leu Ala Arg Asp Ile Met Asn
        770                 775                 780
Asp Ser Asn Tyr Val Val Lys Gly Asn Ala Arg Leu Pro Val Lys Trp
785                 790                 795                 800
Met Ala Pro Glu Ser Ile Phe Asp Cys Val Tyr Thr Val Gln Ser Asp
                805                 810                 815
Val Trp Ser Tyr Gly Ile Leu Leu Trp Glu Ile Phe Ser Leu Gly Leu
            820                 825                 830
Asn Pro Tyr Pro Gly Ile Leu Val Asn Asn Lys Phe Tyr Lys Leu Val
        835                 840                 845
```

```
Lys Asp Gly Tyr Gln Met Ala Gln Pro Val Phe Ala Pro Lys Asn Ile
850                 855                 860

Tyr Ser Ile Met Gln Ser Cys Trp Asp Leu Glu Pro Thr Arg Arg Pro
865                 870                 875                 880

Thr Phe Gln Gln Ile Cys Phe Leu Leu Gln Glu Gln Ala Arg Leu Glu
                885                 890                 895

Arg Arg Asp Gln Asp Tyr Ala Asn Leu Pro Ser Ser Gly Gly Ser Ser
            900                 905                 910

Gly Ser Asp Ser Gly Gly Gly Ser Gly Gly Ser Ser Ser Glu Pro
            915                 920                 925

Glu Glu Glu Ser Ser Ser Glu His Leu Ala Cys Cys Glu Pro Gly Asp
        930                 935                 940

Ile Ala Gln Pro Leu Leu Gln Pro Asn Asn Tyr Gln Phe Cys
945                 950                 955
```

<210> SEQ ID NO 25
<211> LENGTH: 977
<212> TYPE: PRT
<213> ORGANISM: Artificial Sequence
<220> FEATURE:
<223> OTHER INFORMATION: mCSF1R (full-length + signal peptide)

<400> SEQUENCE: 25

```
Met Glu Leu Gly Pro Pro Leu Val Leu Leu Leu Ala Thr Val Trp His
1               5                   10                  15

Gly Gln Gly Ala Pro Val Ile Glu Pro Ser Gly Pro Glu Leu Val Val
            20                  25                  30

Glu Pro Gly Glu Thr Val Thr Leu Arg Cys Val Ser Asn Gly Ser Val
        35                  40                  45

Glu Trp Asp Gly Pro Ile Ser Pro Tyr Trp Thr Leu Asp Pro Glu Ser
    50                  55                  60

Pro Gly Ser Thr Leu Thr Thr Arg Asn Ala Thr Phe Lys Asn Thr Gly
65                  70                  75                  80

Thr Tyr Arg Cys Thr Glu Leu Glu Asp Pro Met Ala Gly Ser Thr Thr
                85                  90                  95

Ile His Leu Tyr Val Lys Asp Pro Ala His Ser Trp Asn Leu Leu Ala
            100                 105                 110

Gln Glu Val Thr Val Val Glu Gly Gln Glu Ala Val Leu Pro Cys Leu
        115                 120                 125

Ile Thr Asp Pro Ala Leu Lys Asp Ser Val Ser Leu Met Arg Glu Gly
    130                 135                 140

Gly Arg Gln Val Leu Arg Lys Thr Val Tyr Phe Phe Ser Pro Trp Arg
145                 150                 155                 160

Gly Phe Ile Ile Arg Lys Ala Lys Val Leu Asp Ser Asn Thr Tyr Val
                165                 170                 175

Cys Lys Thr Met Val Asn Gly Arg Glu Ser Thr Ser Thr Gly Ile Trp
            180                 185                 190

Leu Lys Val Asn Arg Val His Pro Glu Pro Pro Gln Ile Lys Leu Glu
        195                 200                 205

Pro Ser Lys Leu Val Arg Ile Arg Gly Glu Ala Ala Gln Ile Val Cys
    210                 215                 220

Ser Ala Thr Asn Ala Glu Val Gly Phe Asn Val Ile Leu Lys Arg Gly
225                 230                 235                 240

Asp Thr Lys Leu Glu Ile Pro Leu Asn Ser Asp Phe Gln Asp Asn Tyr
                245                 250                 255

Tyr Lys Lys Val Arg Ala Leu Ser Leu Asn Ala Val Asp Phe Gln Asp
```

```
                260                 265                 270
Ala Gly Ile Tyr Ser Cys Val Ala Ser Asn Asp Val Gly Thr Arg Thr
            275                 280                 285
Ala Thr Met Asn Phe Gln Val Val Glu Ser Ala Tyr Leu Asn Leu Thr
        290                 295                 300
Ser Glu Gln Ser Leu Leu Gln Glu Val Ser Val Gly Asp Ser Leu Ile
305                 310                 315                 320
Leu Thr Val His Ala Asp Ala Tyr Pro Ser Ile Gln His Tyr Asn Trp
                325                 330                 335
Thr Tyr Leu Gly Pro Phe Phe Glu Asp Gln Arg Lys Leu Glu Phe Ile
            340                 345                 350
Thr Gln Arg Ala Ile Tyr Arg Tyr Thr Phe Lys Leu Phe Leu Asn Arg
        355                 360                 365
Val Lys Ala Ser Glu Ala Gly Gln Tyr Phe Leu Met Ala Gln Asn Lys
    370                 375                 380
Ala Gly Trp Asn Asn Leu Thr Phe Glu Leu Thr Leu Arg Tyr Pro Pro
385                 390                 395                 400
Glu Val Ser Val Thr Trp Met Pro Val Asn Gly Ser Asp Val Leu Phe
                405                 410                 415
Cys Asp Val Ser Gly Tyr Pro Gln Pro Ser Val Thr Trp Met Glu Cys
            420                 425                 430
Arg Gly His Thr Asp Arg Cys Asp Glu Ala Gln Ala Leu Gln Val Trp
        435                 440                 445
Asn Asp Thr His Pro Glu Val Leu Ser Gln Lys Pro Phe Asp Lys Val
    450                 455                 460
Ile Ile Gln Ser Gln Leu Pro Ile Gly Thr Leu Lys His Asn Met Thr
465                 470                 475                 480
Tyr Phe Cys Lys Thr His Asn Ser Val Gly Asn Ser Ser Gln Tyr Phe
                485                 490                 495
Arg Ala Val Ser Leu Gly Gln Ser Lys Gln Leu Pro Asp Glu Ser Leu
            500                 505                 510
Phe Thr Pro Val Val Val Ala Cys Met Ser Val Met Ser Leu Leu Val
        515                 520                 525
Leu Leu Leu Leu Leu Leu Leu Tyr Lys Tyr Lys Gln Lys Pro Lys Tyr
    530                 535                 540
Gln Val Arg Trp Lys Ile Ile Glu Arg Tyr Glu Gly Asn Ser Tyr Thr
545                 550                 555                 560
Phe Ile Asp Pro Thr Gln Leu Pro Tyr Asn Glu Lys Trp Glu Phe Pro
                565                 570                 575
Arg Asn Asn Leu Gln Phe Gly Lys Thr Leu Gly Ala Gly Ala Phe Gly
            580                 585                 590
Lys Val Val Glu Ala Thr Ala Phe Gly Leu Gly Lys Glu Asp Ala Val
        595                 600                 605
Leu Lys Val Ala Val Lys Met Leu Lys Ser Thr Ala His Ala Asp Glu
    610                 615                 620
Lys Glu Ala Leu Met Ser Glu Leu Lys Ile Met Ser His Leu Gly Gln
625                 630                 635                 640
His Glu Asn Ile Val Asn Leu Leu Gly Ala Cys Thr His Gly Gly Pro
                645                 650                 655
Val Leu Val Ile Thr Glu Tyr Cys Cys Tyr Gly Asp Leu Leu Asn Phe
            660                 665                 670
Leu Arg Arg Lys Ala Glu Ala Met Leu Gly Pro Ser Leu Ser Pro Gly
        675                 680                 685
```

```
Gln Asp Ser Glu Gly Asp Ser Ser Tyr Lys Asn Ile His Leu Glu Lys
        690                 695                 700

Lys Tyr Val Arg Arg Asp Ser Gly Phe Ser Ser Gln Gly Val Asp Thr
705                 710                 715                 720

Tyr Val Glu Met Arg Pro Val Ser Thr Ser Ser Ser Asp Ser Phe Phe
                725                 730                 735

Lys Gln Asp Leu Asp Lys Glu Ala Ser Arg Pro Leu Glu Leu Trp Asp
            740                 745                 750

Leu Leu His Phe Ser Ser Gln Val Ala Gln Gly Met Ala Phe Leu Ala
        755                 760                 765

Ser Lys Asn Cys Ile His Arg Asp Val Ala Ala Arg Asn Val Leu Leu
770                 775                 780

Thr Ser Gly His Val Ala Lys Ile Gly Asp Phe Gly Leu Ala Arg Asp
785                 790                 795                 800

Ile Met Asn Asp Ser Asn Tyr Val Val Lys Gly Asn Ala Arg Leu Pro
                805                 810                 815

Val Lys Trp Met Ala Pro Glu Ser Ile Phe Asp Cys Val Tyr Thr Val
            820                 825                 830

Gln Ser Asp Val Trp Ser Tyr Gly Ile Leu Leu Trp Glu Ile Phe Ser
        835                 840                 845

Leu Gly Leu Asn Pro Tyr Pro Gly Ile Leu Val Asn Asn Lys Phe Tyr
    850                 855                 860

Lys Leu Val Lys Asp Gly Tyr Gln Met Ala Gln Pro Val Phe Ala Pro
865                 870                 875                 880

Lys Asn Ile Tyr Ser Ile Met Gln Ser Cys Trp Asp Leu Glu Pro Thr
                885                 890                 895

Arg Arg Pro Thr Phe Gln Gln Ile Cys Phe Leu Leu Gln Glu Gln Ala
            900                 905                 910

Arg Leu Glu Arg Arg Asp Gln Asp Tyr Ala Asn Leu Pro Ser Ser Gly
        915                 920                 925

Gly Ser Ser Gly Ser Asp Ser Gly Gly Ser Ser Gly Gly Ser Ser
    930                 935                 940

Ser Glu Pro Glu Glu Ser Ser Glu His Leu Ala Cys Cys Glu
945                 950                 955                 960

Pro Gly Asp Ile Ala Gln Pro Leu Leu Gln Pro Asn Asn Tyr Gln Phe
                965                 970                 975

Cys
```

<210> SEQ ID NO 26
<211> LENGTH: 492
<212> TYPE: PRT
<213> ORGANISM: Artificial Sequence
<220> FEATURE:
<223> OTHER INFORMATION: hCSF1R-ECD.511

<400> SEQUENCE: 26

```
Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
                20                  25                  30

Gly Pro Pro Ser Pro His Trp Thr Leu Tyr Ser Asp Gly Ser Ser Ser
            35                  40                  45

Ile Leu Ser Thr Asn Asn Ala Thr Phe Gln Asn Thr Gly Thr Tyr Arg
        50                  55                  60

Cys Thr Glu Pro Gly Asp Pro Leu Gly Gly Ser Ala Ala Ile His Leu
65                  70                  75                  80
```

```
Tyr Val Lys Asp Pro Ala Arg Pro Trp Asn Val Leu Ala Gln Glu Val
                85                  90                  95
Val Val Phe Glu Asp Gln Asp Ala Leu Leu Pro Cys Leu Leu Thr Asp
            100                 105                 110
Pro Val Leu Glu Ala Gly Val Ser Leu Val Arg Val Arg Gly Arg Pro
        115                 120                 125
Leu Met Arg His Thr Asn Tyr Ser Phe Ser Pro Trp His Gly Phe Thr
    130                 135                 140
Ile His Arg Ala Lys Phe Ile Gln Ser Gln Asp Tyr Gln Cys Ser Ala
145                 150                 155                 160
Leu Met Gly Gly Arg Lys Val Met Ser Ile Ser Arg Leu Lys Val
                165                 170                 175
Gln Lys Val Ile Pro Gly Pro Ala Leu Thr Leu Val Pro Ala Glu
            180                 185                 190
Leu Val Arg Ile Arg Gly Glu Ala Ala Gln Ile Val Cys Ser Ala Ser
        195                 200                 205
Ser Val Asp Val Asn Phe Asp Val Phe Leu Gln His Asn Asn Thr Lys
    210                 215                 220
Leu Ala Ile Pro Gln Gln Ser Asp Phe His Asn Asn Arg Tyr Gln Lys
225                 230                 235                 240
Val Leu Thr Leu Asn Leu Asp Gln Val Asp Phe Gln His Ala Gly Asn
                245                 250                 255
Tyr Ser Cys Val Ala Ser Asn Val Gln Gly Lys His Ser Thr Ser Met
            260                 265                 270
Phe Phe Arg Val Val Glu Ser Ala Tyr Leu Asn Leu Ser Ser Glu Gln
        275                 280                 285
Asn Leu Ile Gln Glu Val Thr Val Gly Glu Gly Leu Asn Leu Lys Val
    290                 295                 300
Met Val Glu Ala Tyr Pro Gly Leu Gln Gly Phe Asn Trp Thr Tyr Leu
305                 310                 315                 320
Gly Pro Phe Ser Asp His Gln Pro Glu Pro Lys Leu Ala Asn Ala Thr
                325                 330                 335
Thr Lys Asp Thr Tyr Arg His Thr Phe Thr Leu Ser Leu Pro Arg Leu
            340                 345                 350
Lys Pro Ser Glu Ala Gly Arg Tyr Ser Phe Leu Ala Arg Asn Pro Gly
        355                 360                 365
Gly Trp Arg Ala Leu Thr Phe Glu Leu Thr Leu Arg Tyr Pro Pro Glu
    370                 375                 380
Val Ser Val Ile Trp Thr Phe Ile Asn Gly Ser Gly Thr Leu Leu Cys
385                 390                 395                 400
Ala Ala Ser Gly Tyr Pro Gln Pro Asn Val Thr Trp Leu Gln Cys Ser
                405                 410                 415
Gly His Thr Asp Arg Cys Asp Glu Ala Gln Val Leu Gln Val Trp Asp
            420                 425                 430
Asp Pro Tyr Pro Glu Val Leu Ser Gln Glu Pro Phe His Lys Val Thr
        435                 440                 445
Val Gln Ser Leu Leu Thr Val Glu Thr Leu Glu His Asn Gln Thr Tyr
    450                 455                 460
Glu Cys Arg Ala His Asn Ser Val Gly Ser Gly Ser Trp Ala Phe Ile
465                 470                 475                 480
Pro Ile Ser Ala Gly Ala His Thr His Pro Pro Asp
                485                 490
```

```
<210> SEQ ID NO 27
<211> LENGTH: 511
<212> TYPE: PRT
<213> ORGANISM: Artificial Sequence
<220> FEATURE:
<223> OTHER INFORMATION: hCSF1R-ECD.511 with signal peptide

<400> SEQUENCE: 27
```

| Met | Gly | Pro | Gly | Val | Leu | Leu | Leu | Leu | Val | Ala | Thr | Ala | Trp | His |
|---|---|---|---|---|---|---|---|---|---|---|---|---|---|---|
| 1 | | | | 5 | | | | | 10 | | | | | 15 |

| Gly | Gln | Gly | Ile | Pro | Val | Ile | Glu | Pro | Ser | Val | Pro | Glu | Leu | Val | Val |
|---|---|---|---|---|---|---|---|---|---|---|---|---|---|---|---|
| | | | 20 | | | | | 25 | | | | | 30 | | |

| Lys | Pro | Gly | Ala | Thr | Val | Thr | Leu | Arg | Cys | Val | Gly | Asn | Gly | Ser | Val |
|---|---|---|---|---|---|---|---|---|---|---|---|---|---|---|---|
| | | | 35 | | | | | 40 | | | | | 45 | | |

| Glu | Trp | Asp | Gly | Pro | Pro | Ser | Pro | His | Trp | Thr | Leu | Tyr | Ser | Asp | Gly |
|---|---|---|---|---|---|---|---|---|---|---|---|---|---|---|---|
| | 50 | | | | | 55 | | | | | 60 | | | | |

| Ser | Ser | Ser | Ile | Leu | Ser | Thr | Asn | Asn | Ala | Thr | Phe | Gln | Asn | Thr | Gly |
|---|---|---|---|---|---|---|---|---|---|---|---|---|---|---|---|
| 65 | | | | | 70 | | | | | 75 | | | | | 80 |

| Thr | Tyr | Arg | Cys | Thr | Glu | Pro | Gly | Asp | Pro | Leu | Gly | Gly | Ser | Ala | Ala |
|---|---|---|---|---|---|---|---|---|---|---|---|---|---|---|---|
| | | | | 85 | | | | | 90 | | | | | 95 | |

| Ile | His | Leu | Tyr | Val | Lys | Asp | Pro | Ala | Arg | Pro | Trp | Asn | Val | Leu | Ala |
|---|---|---|---|---|---|---|---|---|---|---|---|---|---|---|---|
| | | | 100 | | | | | 105 | | | | | 110 | | |

| Gln | Glu | Val | Val | Val | Phe | Glu | Asp | Gln | Asp | Ala | Leu | Leu | Pro | Cys | Leu |
|---|---|---|---|---|---|---|---|---|---|---|---|---|---|---|---|
| | | | 115 | | | | | 120 | | | | | 125 | | |

| Leu | Thr | Asp | Pro | Val | Leu | Glu | Ala | Gly | Val | Ser | Leu | Val | Arg | Val | Arg |
|---|---|---|---|---|---|---|---|---|---|---|---|---|---|---|---|
| 130 | | | | | 135 | | | | | 140 | | | | | |

| Gly | Arg | Pro | Leu | Met | Arg | His | Thr | Asn | Tyr | Ser | Phe | Ser | Pro | Trp | His |
|---|---|---|---|---|---|---|---|---|---|---|---|---|---|---|---|
| 145 | | | | | 150 | | | | | 155 | | | | | 160 |

| Gly | Phe | Thr | Ile | His | Arg | Ala | Lys | Phe | Ile | Gln | Ser | Gln | Asp | Tyr | Gln |
|---|---|---|---|---|---|---|---|---|---|---|---|---|---|---|---|
| | | | | 165 | | | | | 170 | | | | | 175 | |

| Cys | Ser | Ala | Leu | Met | Gly | Gly | Arg | Lys | Val | Met | Ser | Ile | Ser | Ile | Arg |
|---|---|---|---|---|---|---|---|---|---|---|---|---|---|---|---|
| | | | | 180 | | | | | 185 | | | | | 190 | |

| Leu | Lys | Val | Gln | Lys | Val | Ile | Pro | Gly | Pro | Pro | Ala | Leu | Thr | Leu | Val |
|---|---|---|---|---|---|---|---|---|---|---|---|---|---|---|---|
| | | 195 | | | | | 200 | | | | | 205 | | | |

| Pro | Ala | Glu | Leu | Val | Arg | Ile | Arg | Gly | Glu | Ala | Ala | Gln | Ile | Val | Cys |
|---|---|---|---|---|---|---|---|---|---|---|---|---|---|---|---|
| | 210 | | | | | 215 | | | | | 220 | | | | |

| Ser | Ala | Ser | Ser | Val | Asp | Val | Asn | Phe | Asp | Val | Phe | Leu | Gln | His | Asn |
|---|---|---|---|---|---|---|---|---|---|---|---|---|---|---|---|
| 225 | | | | | 230 | | | | | 235 | | | | | 240 |

| Asn | Thr | Lys | Leu | Ala | Ile | Pro | Gln | Gln | Ser | Asp | Phe | His | Asn | Asn | Arg |
|---|---|---|---|---|---|---|---|---|---|---|---|---|---|---|---|
| | | | | 245 | | | | | 250 | | | | | 255 | |

| Tyr | Gln | Lys | Val | Leu | Thr | Leu | Asn | Leu | Asp | Gln | Val | Asp | Phe | Gln | His |
|---|---|---|---|---|---|---|---|---|---|---|---|---|---|---|---|
| | | | 260 | | | | | 265 | | | | | 270 | | |

| Ala | Gly | Asn | Tyr | Ser | Cys | Val | Ala | Ser | Asn | Val | Gln | Gly | Lys | His | Ser |
|---|---|---|---|---|---|---|---|---|---|---|---|---|---|---|---|
| | | | 275 | | | | | 280 | | | | | 285 | | |

| Thr | Ser | Met | Phe | Phe | Arg | Val | Val | Glu | Ser | Ala | Tyr | Leu | Asn | Leu | Ser |
|---|---|---|---|---|---|---|---|---|---|---|---|---|---|---|---|
| | 290 | | | | | 295 | | | | | 300 | | | | |

| Ser | Glu | Gln | Asn | Leu | Ile | Gln | Glu | Val | Thr | Val | Gly | Glu | Gly | Leu | Asn |
|---|---|---|---|---|---|---|---|---|---|---|---|---|---|---|---|
| 305 | | | | | 310 | | | | | 315 | | | | | 320 |

| Leu | Lys | Val | Met | Val | Glu | Ala | Tyr | Pro | Gly | Leu | Gln | Gly | Phe | Asn | Trp |
|---|---|---|---|---|---|---|---|---|---|---|---|---|---|---|---|
| | | | | 325 | | | | | 330 | | | | | 335 | |

| Thr | Tyr | Leu | Gly | Pro | Phe | Ser | Asp | His | Gln | Pro | Glu | Pro | Lys | Leu | Ala |
|---|---|---|---|---|---|---|---|---|---|---|---|---|---|---|---|
| | | | 340 | | | | | 345 | | | | | 350 | | |

| Asn | Ala | Thr | Thr | Lys | Asp | Thr | Tyr | Arg | His | Thr | Phe | Thr | Leu | Ser | Leu |
|---|---|---|---|---|---|---|---|---|---|---|---|---|---|---|---|
| | | | 355 | | | | | 360 | | | | | 365 | | |

| Pro | Arg | Leu | Lys | Pro | Ser | Glu | Ala | Gly | Arg | Tyr | Ser | Phe | Leu | Ala | Arg |
|---|---|---|---|---|---|---|---|---|---|---|---|---|---|---|---|
| | 370 | | | | | 375 | | | | | 380 | | | | |

```
Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
    450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp
            500                 505                 510

<210> SEQ ID NO 28
<211> LENGTH: 724
<212> TYPE: PRT
<213> ORGANISM: Artificial Sequence
<220> FEATURE:
<223> OTHER INFORMATION: hCSF1R-ECD.511-Fc

<400> SEQUENCE: 28

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
                20                  25                  30

Gly Pro Pro Ser Pro His Trp Thr Leu Tyr Ser Asp Gly Ser Ser Ser
            35                  40                  45

Ile Leu Ser Thr Asn Asn Ala Thr Phe Gln Asn Thr Gly Thr Tyr Arg
        50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
                100                 105                 110

Pro Val Leu Glu Ala Gly Val Ser Leu Val Arg Val Arg Gly Arg Pro
            115                 120                 125

Leu Met Arg His Thr Asn Tyr Ser Phe Ser Pro Trp His Gly Phe Thr
130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
    210                 215                 220

Leu Ala Ile Pro Gln Gln Ser Asp Phe His Asn Asn Arg Tyr Gln Lys
225                 230                 235                 240
```

```
Val Leu Thr Leu Asn Leu Asp Gln Val Asp Phe Gln His Ala Gly Asn
            245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
            275                 280                 285

Asn Leu Ile Gln Glu Val Thr Val Gly Glu Gly Leu Asn Leu Lys Val
            290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
            325                 330                 335

Thr Lys Asp Thr Tyr Arg His Thr Phe Thr Leu Ser Leu Pro Arg Leu
            340                 345                 350

Lys Pro Ser Glu Ala Gly Arg Tyr Ser Phe Leu Ala Arg Asn Pro Gly
            355                 360                 365

Gly Trp Arg Ala Leu Thr Phe Glu Leu Thr Leu Arg Tyr Pro Pro Glu
            370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
            405                 410                 415

Gly His Thr Asp Arg Cys Asp Glu Ala Gln Val Leu Gln Val Trp Asp
            420                 425                 430

Asp Pro Tyr Pro Glu Val Leu Ser Gln Glu Pro Phe His Lys Val Thr
            435                 440                 445

Val Gln Ser Leu Leu Thr Val Glu Thr Leu Glu His Asn Gln Thr Tyr
            450                 455                 460

Glu Cys Arg Ala His Asn Ser Val Gly Ser Gly Ser Trp Ala Phe Ile
465                 470                 475                 480

Pro Ile Ser Ala Gly Ala His Thr His Pro Pro Asp Glu Pro Lys Ser
            485                 490                 495

Ser Asp Lys Thr His Thr Cys Pro Pro Cys Pro Ala Pro Glu Leu Leu
            500                 505                 510

Gly Gly Pro Ser Val Phe Leu Phe Pro Pro Lys Pro Lys Asp Thr Leu
            515                 520                 525

Met Ile Ser Arg Thr Pro Glu Val Thr Cys Val Val Val Asp Val Ser
530                 535                 540

His Glu Asp Pro Glu Val Lys Phe Asn Trp Tyr Val Asp Gly Val Glu
545                 550                 555                 560

Val His Asn Ala Lys Thr Lys Pro Arg Glu Glu Gln Tyr Asn Ser Thr
            565                 570                 575

Tyr Arg Val Val Ser Val Leu Thr Val Leu His Gln Asp Trp Leu Asn
            580                 585                 590

Gly Lys Glu Tyr Lys Cys Lys Val Ser Asn Lys Ala Leu Pro Ala Pro
            595                 600                 605

Ile Glu Lys Thr Ile Ser Lys Ala Lys Gly Gln Pro Arg Glu Pro Gln
            610                 615                 620

Val Tyr Thr Leu Pro Pro Ser Arg Asp Glu Leu Thr Lys Asn Gln Val
625                 630                 635                 640

Ser Leu Thr Cys Leu Val Lys Gly Phe Tyr Pro Ser Asp Ile Ala Val
            645                 650                 655

Glu Trp Glu Ser Asn Gly Gln Pro Glu Asn Asn Tyr Lys Thr Thr Pro
            660                 665                 670
```

```
Pro Val Leu Asp Ser Asp Gly Ser Phe Phe Leu Tyr Ser Lys Leu Thr
            675                 680                 685

Val Asp Lys Ser Arg Trp Gln Gln Gly Asn Val Phe Ser Cys Ser Val
    690                 695                 700

Met His Glu Ala Leu His Asn His Tyr Thr Gln Lys Ser Leu Ser Leu
705                 710                 715                 720

Ser Pro Gly Lys

<210> SEQ ID NO 29
<211> LENGTH: 743
<212> TYPE: PRT
<213> ORGANISM: Artificial Sequence
<220> FEATURE:
<223> OTHER INFORMATION: hCSF1R-ECD.511-Fc with signal peptide

<400> SEQUENCE: 29

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
        115                 120                 125

Leu Thr Asp Pro Val Leu Glu Ala Gly Val Ser Leu Val Arg Val Arg
130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
        195                 200                 205

Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
        275                 280                 285

Thr Ser Met Phe Phe Arg Val Val Glu Ser Ala Tyr Leu Asn Leu Ser
    290                 295                 300

Ser Glu Gln Asn Leu Ile Gln Glu Val Thr Val Gly Glu Gly Leu Asn
```

```
              305                 310                 315                 320
Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
                340                 345                 350

Asn Ala Thr Thr Lys Asp Thr Tyr Arg His Thr Phe Thr Leu Ser Leu
                355                 360                 365

Pro Arg Leu Lys Pro Ser Glu Ala Gly Arg Tyr Ser Phe Leu Ala Arg
            370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
                420                 425                 430

Gln Cys Ser Gly His Thr Asp Arg Cys Asp Glu Ala Gln Val Leu Gln
                435                 440                 445

Val Trp Asp Asp Pro Tyr Pro Glu Val Leu Ser Gln Glu Pro Phe His
        450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
                500                 505                 510

Pro Lys Ser Ser Asp Lys Thr His Thr Cys Pro Pro Cys Pro Ala Pro
                515                 520                 525

Glu Leu Leu Gly Gly Pro Ser Val Phe Leu Phe Pro Pro Lys Pro Lys
            530                 535                 540

Asp Thr Leu Met Ile Ser Arg Thr Pro Glu Val Thr Cys Val Val Val
545                 550                 555                 560

Asp Val Ser His Glu Asp Pro Glu Val Lys Phe Asn Trp Tyr Val Asp
                565                 570                 575

Gly Val Glu Val His Asn Ala Lys Thr Lys Pro Arg Glu Glu Gln Tyr
                580                 585                 590

Asn Ser Thr Tyr Arg Val Val Ser Val Leu Thr Val Leu His Gln Asp
            595                 600                 605

Trp Leu Asn Gly Lys Glu Tyr Lys Cys Lys Val Ser Asn Lys Ala Leu
        610                 615                 620

Pro Ala Pro Ile Glu Lys Thr Ile Ser Lys Ala Lys Gly Gln Pro Arg
625                 630                 635                 640

Glu Pro Gln Val Tyr Thr Leu Pro Pro Ser Arg Asp Glu Leu Thr Lys
                645                 650                 655

Asn Gln Val Ser Leu Thr Cys Leu Val Lys Gly Phe Tyr Pro Ser Asp
                660                 665                 670

Ile Ala Val Glu Trp Glu Ser Asn Gly Gln Pro Glu Asn Asn Tyr Lys
                675                 680                 685

Thr Thr Pro Pro Val Leu Asp Ser Asp Gly Ser Phe Phe Leu Tyr Ser
            690                 695                 700

Lys Leu Thr Val Asp Lys Ser Arg Trp Gln Gln Gly Asn Val Phe Ser
705                 710                 715                 720

Cys Ser Val Met His Glu Ala Leu His Asn His Tyr Thr Gln Lys Ser
                725                 730                 735
```

Leu Ser Leu Ser Pro Gly Lys
            740

<210> SEQ ID NO 30
<211> LENGTH: 233
<212> TYPE: PRT
<213> ORGANISM: Artificial Sequence
<220> FEATURE:
<223> OTHER INFORMATION: Fc C237S with N-terminal GS linker

<400> SEQUENCE: 30

Gly Ser Glu Pro Lys Ser Ser Asp Lys Thr His Thr Cys Pro Pro Cys
1               5                   10                  15

Pro Ala Pro Glu Leu Leu Gly Gly Pro Ser Val Phe Leu Phe Pro Pro
            20                  25                  30

Lys Pro Lys Asp Thr Leu Met Ile Ser Arg Thr Pro Glu Val Thr Cys
        35                  40                  45

Val Val Val Asp Val Ser His Glu Asp Pro Glu Val Lys Phe Asn Trp
    50                  55                  60

Tyr Val Asp Gly Val Glu Val His Asn Ala Lys Thr Lys Pro Arg Glu
65                  70                  75                  80

Glu Gln Tyr Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Ala Leu Pro Ala Pro Ile Glu Lys Thr Ile Ser Lys Ala Lys Gly
        115                 120                 125

Gln Pro Arg Glu Pro Gln Val Tyr Thr Leu Pro Pro Ser Arg Asp Glu
    130                 135                 140

Leu Thr Lys Asn Gln Val Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230

<210> SEQ ID NO 31
<211> LENGTH: 727
<212> TYPE: PRT
<213> ORGANISM: Artificial Sequence
<220> FEATURE:
<223> OTHER INFORMATION: hCSF1R-ECD.512-Fc with GS linker

<400> SEQUENCE: 31

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
        35                  40                  45

Ile Leu Ser Thr Asn Asn Ala Thr Phe Gln Asn Thr Gly Thr Tyr Arg
    50                  55                  60

```
Cys Thr Glu Pro Gly Asp Pro Leu Gly Gly Ser Ala Ala Ile His Leu
 65                  70                  75                  80

Tyr Val Lys Asp Pro Ala Arg Pro Trp Asn Val Leu Ala Gln Glu Val
                 85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
    130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
    210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
        275                 280                 285

Asn Leu Ile Gln Glu Val Thr Val Gly Glu Gly Leu Asn Leu Lys Val
    290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335

Thr Lys Asp Thr Tyr Arg His Thr Phe Thr Leu Ser Leu Pro Arg Leu
            340                 345                 350

Lys Pro Ser Glu Ala Gly Arg Tyr Ser Phe Leu Ala Arg Asn Pro Gly
        355                 360                 365

Gly Trp Arg Ala Leu Thr Phe Glu Leu Thr Leu Arg Tyr Pro Pro Glu
    370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415

Gly His Thr Asp Arg Cys Asp Glu Ala Gln Val Leu Gln Val Trp Asp
            420                 425                 430

Asp Pro Tyr Pro Glu Val Leu Ser Gln Glu Pro Phe His Lys Val Thr
        435                 440                 445

Val Gln Ser Leu Leu Thr Val Glu Thr Leu Glu His Asn Gln Thr Tyr
    450                 455                 460

Glu Cys Arg Ala His Asn Ser Val Gly Ser Gly Ser Trp Ala Phe Ile
465                 470                 475                 480

Pro Ile Ser Ala Gly Ala His Thr His Pro Pro Asp Glu Gly Phe Glu
                485                 490                 495
```

```
Pro Lys Ser Ser Asp Lys Thr His Thr Cys Pro Pro Cys Pro Ala Pro
            500                 505                 510

Glu Leu Leu Gly Gly Pro Ser Val Phe Leu Phe Pro Pro Lys Pro Lys
            515                 520                 525

Asp Thr Leu Met Ile Ser Arg Thr Pro Glu Val Thr Cys Val Val Val
            530                 535                 540

Asp Val Ser His Glu Asp Pro Glu Val Lys Phe Asn Trp Tyr Val Asp
545                 550                 555                 560

Gly Val Glu Val His Asn Ala Lys Thr Lys Pro Arg Glu Glu Gln Tyr
                565                 570                 575

Asn Ser Thr Tyr Arg Val Val Ser Val Leu Thr Val Leu His Gln Asp
            580                 585                 590

Trp Leu Asn Gly Lys Glu Tyr Lys Cys Lys Val Ser Asn Lys Ala Leu
            595                 600                 605

Pro Ala Pro Ile Glu Lys Thr Ile Ser Lys Ala Lys Gly Gln Pro Arg
            610                 615                 620

Glu Pro Gln Val Tyr Thr Leu Pro Pro Ser Arg Asp Glu Leu Thr Lys
625                 630                 635                 640

Asn Gln Val Ser Leu Thr Cys Leu Val Lys Gly Phe Tyr Pro Ser Asp
                645                 650                 655

Ile Ala Val Glu Trp Glu Ser Asn Gly Gln Pro Glu Asn Asn Tyr Lys
            660                 665                 670

Thr Thr Pro Pro Val Leu Asp Ser Asp Gly Ser Phe Phe Leu Tyr Ser
            675                 680                 685

Lys Leu Thr Val Asp Lys Ser Arg Trp Gln Gln Gly Asn Val Phe Ser
            690                 695                 700

Cys Ser Val Met His Glu Ala Leu His Asn His Tyr Thr Gln Lys Ser
705                 710                 715                 720

Leu Ser Leu Ser Pro Gly Lys
                725

<210> SEQ ID NO 32
<211> LENGTH: 721
<212> TYPE: PRT
<213> ORGANISM: Artificial Sequence
<220> FEATURE:
<223> OTHER INFORMATION: hCSF1R-ECD.506-Fc with GS linker

<400> SEQUENCE: 32

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
            35                  40                  45

Ile Leu Ser Thr Asn Asn Ala Thr Phe Gln Asn Thr Gly Thr Tyr Arg
        50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
            115                 120                 125
```

```
Leu Met Arg His Thr Asn Tyr Ser Phe Ser Pro Trp His Gly Phe Thr
130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
    210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
                260                 265                 270

Phe Phe Arg Val Val Glu Ser Ala Tyr Leu Asn Leu Ser Ser Glu Gln
            275                 280                 285

Asn Leu Ile Gln Glu Val Thr Val Gly Glu Gly Leu Asn Leu Lys Val
        290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335

Thr Lys Asp Thr Tyr Arg His Thr Phe Thr Leu Ser Leu Pro Arg Leu
                340                 345                 350

Lys Pro Ser Glu Ala Gly Arg Tyr Ser Phe Leu Ala Arg Asn Pro Gly
            355                 360                 365

Gly Trp Arg Ala Leu Thr Phe Glu Leu Thr Leu Arg Tyr Pro Pro Glu
        370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415

Gly His Thr Asp Arg Cys Asp Glu Ala Gln Val Leu Gln Val Trp Asp
                420                 425                 430

Asp Pro Tyr Pro Glu Val Leu Ser Gln Glu Pro Phe His Lys Val Thr
            435                 440                 445

Val Gln Ser Leu Leu Thr Val Glu Thr Leu Glu His Asn Gln Thr Tyr
        450                 455                 460

Glu Cys Arg Ala His Asn Ser Val Gly Ser Gly Ser Trp Ala Phe Ile
465                 470                 475                 480

Pro Ile Ser Ala Gly Ala His Gly Phe Glu Pro Lys Ser Ser Asp Lys
                485                 490                 495

Thr His Thr Cys Pro Pro Cys Pro Ala Pro Glu Leu Leu Gly Gly Pro
                500                 505                 510

Ser Val Phe Leu Phe Pro Pro Lys Pro Lys Asp Thr Leu Met Ile Ser
            515                 520                 525

Arg Thr Pro Glu Val Thr Cys Val Val Val Asp Val Ser His Glu Asp
        530                 535                 540

Pro Glu Val Lys Phe Asn Trp Tyr Val Asp Gly Val Glu Val His Asn
545                 550                 555                 560
```

```
Ala Lys Thr Lys Pro Arg Glu Glu Gln Tyr Asn Ser Thr Tyr Arg Val
                565                 570                 575

Val Ser Val Leu Thr Val Leu His Gln Asp Trp Leu Asn Gly Lys Glu
            580                 585                 590

Tyr Lys Cys Lys Val Ser Asn Lys Ala Leu Pro Ala Pro Ile Glu Lys
        595                 600                 605

Thr Ile Ser Lys Ala Lys Gly Gln Pro Arg Glu Pro Gln Val Tyr Thr
    610                 615                 620

Leu Pro Pro Ser Arg Asp Glu Leu Thr Lys Asn Gln Val Ser Leu Thr
625                 630                 635                 640

Cys Leu Val Lys Gly Phe Tyr Pro Ser Asp Ile Ala Val Glu Trp Glu
            645                 650                 655

Ser Asn Gly Gln Pro Glu Asn Asn Tyr Lys Thr Thr Pro Pro Val Leu
        660                 665                 670

Asp Ser Asp Gly Ser Phe Phe Leu Tyr Ser Lys Leu Thr Val Asp Lys
    675                 680                 685

Ser Arg Trp Gln Gln Gly Asn Val Phe Ser Cys Ser Val Met His Glu
690                 695                 700

Ala Leu His Asn His Tyr Thr Gln Lys Ser Leu Ser Leu Ser Pro Gly
705                 710                 715                 720

Lys

<210> SEQ ID NO 33
<211> LENGTH: 726
<212> TYPE: PRT
<213> ORGANISM: Artificial Sequence
<220> FEATURE:
<223> OTHER INFORMATION: mCSF1R-ECD.511-Fc with GS linker

<400> SEQUENCE: 33

Ala Pro Val Ile Glu Pro Ser Gly Pro Glu Leu Val Val Glu Pro Gly
1               5                   10                  15

Glu Thr Val Thr Leu Arg Cys Val Ser Asn Gly Ser Val Glu Trp Asp
            20                  25                  30

Gly Pro Ile Ser Pro Tyr Trp Thr Leu Asp Pro Glu Ser Pro Gly Ser
        35                  40                  45

Thr Leu Thr Thr Arg Asn Ala Thr Phe Lys Asn Thr Gly Thr Tyr Arg
    50                  55                  60

Cys Thr Glu Leu Glu Asp Pro Met Ala Gly Ser Thr Thr Ile His Leu
65                  70                  75                  80

Tyr Val Lys Asp Pro Ala His Ser Trp Asn Leu Leu Ala Gln Glu Val
            85                  90                  95

Thr Val Val Glu Gly Gln Glu Ala Val Leu Pro Cys Leu Ile Thr Asp
        100                 105                 110

Pro Ala Leu Lys Asp Ser Val Ser Leu Met Arg Glu Gly Gly Arg Gln
    115                 120                 125

Val Leu Arg Lys Thr Val Tyr Phe Phe Ser Pro Trp Arg Gly Phe Ile
130                 135                 140

Ile Arg Lys Ala Lys Val Leu Asp Ser Asn Thr Tyr Val Cys Lys Thr
145                 150                 155                 160

Met Val Asn Gly Arg Glu Ser Thr Ser Thr Gly Ile Trp Leu Lys Val
            165                 170                 175

Asn Arg Val His Pro Glu Pro Pro Gln Ile Lys Leu Glu Pro Ser Lys
        180                 185                 190

Leu Val Arg Ile Arg Gly Glu Ala Ala Gln Ile Val Cys Ser Ala Thr
```

-continued

```
            195                 200                 205
Asn Ala Glu Val Gly Phe Asn Val Ile Leu Lys Arg Gly Asp Thr Lys
    210                 215                 220
Leu Glu Ile Pro Leu Asn Ser Asp Phe Gln Asp Asn Tyr Tyr Lys Lys
225                 230                 235                 240
Val Arg Ala Leu Ser Leu Asn Ala Val Asp Phe Gln Asp Ala Gly Ile
                245                 250                 255
Tyr Ser Cys Val Ala Ser Asn Asp Val Gly Thr Arg Thr Ala Thr Met
            260                 265                 270
Asn Phe Gln Val Glu Ser Ala Tyr Leu Asn Leu Thr Ser Glu Gln
        275                 280                 285
Ser Leu Leu Gln Glu Val Ser Val Gly Asp Ser Leu Ile Leu Thr Val
    290                 295                 300
His Ala Asp Ala Tyr Pro Ser Ile Gln His Tyr Asn Trp Thr Tyr Leu
305                 310                 315                 320
Gly Pro Phe Phe Glu Asp Gln Arg Lys Leu Glu Phe Ile Thr Gln Arg
                325                 330                 335
Ala Ile Tyr Arg Tyr Thr Phe Lys Leu Phe Leu Asn Arg Val Lys Ala
            340                 345                 350
Ser Glu Ala Gly Gln Tyr Phe Leu Met Ala Gln Asn Lys Ala Gly Trp
        355                 360                 365
Asn Asn Leu Thr Phe Glu Leu Thr Leu Arg Tyr Pro Pro Glu Val Ser
    370                 375                 380
Val Thr Trp Met Pro Val Asn Gly Ser Asp Val Leu Phe Cys Asp Val
385                 390                 395                 400
Ser Gly Tyr Pro Gln Pro Ser Val Thr Trp Met Glu Cys Arg Gly His
                405                 410                 415
Thr Asp Arg Cys Asp Glu Ala Gln Ala Leu Gln Val Trp Asn Asp Thr
            420                 425                 430
His Pro Glu Val Leu Ser Gln Lys Pro Phe Asp Lys Val Ile Ile Gln
        435                 440                 445
Ser Gln Leu Pro Ile Gly Thr Leu Lys His Asn Met Thr Tyr Phe Cys
    450                 455                 460
Lys Thr His Asn Ser Val Gly Asn Ser Ser Gln Tyr Phe Arg Ala Val
465                 470                 475                 480
Ser Leu Gly Gln Ser Lys Gln Leu Pro Asp Glu Ser Gly Phe Glu Pro
                485                 490                 495
Lys Ser Ser Asp Lys Thr His Thr Cys Pro Pro Cys Pro Ala Pro Glu
            500                 505                 510
Leu Leu Gly Gly Pro Ser Val Phe Leu Phe Pro Pro Lys Pro Lys Asp
        515                 520                 525
Thr Leu Met Ile Ser Arg Thr Pro Glu Val Thr Cys Val Val Val Asp
    530                 535                 540
Val Ser His Glu Asp Pro Glu Val Lys Phe Asn Trp Tyr Val Asp Gly
545                 550                 555                 560
Val Glu Val His Asn Ala Lys Thr Lys Pro Arg Glu Glu Gln Tyr Asn
                565                 570                 575
Ser Thr Tyr Arg Val Val Ser Val Leu Thr Val Leu His Gln Asp Trp
            580                 585                 590
Leu Asn Gly Lys Glu Tyr Lys Cys Lys Val Ser Asn Lys Ala Leu Pro
        595                 600                 605
Ala Pro Ile Glu Lys Thr Ile Ser Lys Ala Lys Gly Gln Pro Arg Glu
    610                 615                 620
```

```
Pro Gln Val Tyr Thr Leu Pro Pro Ser Arg Asp Glu Leu Thr Lys Asn
625                 630                 635                 640

Gln Val Ser Leu Thr Cys Leu Val Lys Gly Phe Tyr Pro Ser Asp Ile
            645                 650                 655

Ala Val Glu Trp Glu Ser Asn Gly Gln Pro Glu Asn Asn Tyr Lys Thr
            660                 665                 670

Thr Pro Pro Val Leu Asp Ser Asp Gly Ser Phe Phe Leu Tyr Ser Lys
            675                 680                 685

Leu Thr Val Asp Lys Ser Arg Trp Gln Gln Gly Asn Val Phe Ser Cys
            690                 695                 700

Ser Val Met His Glu Ala Leu His Asn His Tyr Thr Gln Lys Ser Leu
705                 710                 715                 720

Ser Leu Ser Pro Gly Lys
            725

<210> SEQ ID NO 34
<211> LENGTH: 721
<212> TYPE: PRT
<213> ORGANISM: Artificial Sequence
<220> FEATURE:
<223> OTHER INFORMATION: mCSF1R-ECD.506-Fc with GS linker

<400> SEQUENCE: 34

Ala Pro Val Ile Glu Pro Ser Gly Pro Glu Leu Val Val Glu Pro Gly
1               5                   10                  15

Glu Thr Val Thr Leu Arg Cys Val Ser Asn Gly Ser Val Glu Trp Asp
            20                  25                  30

Gly Pro Ile Ser Pro Tyr Trp Thr Leu Asp Pro Glu Ser Pro Gly Ser
        35                  40                  45

Thr Leu Thr Thr Arg Asn Ala Thr Phe Lys Asn Thr Gly Thr Tyr Arg
    50                  55                  60

Cys Thr Glu Leu Glu Asp Pro Met Ala Gly Ser Thr Thr Ile His Leu
65              70                  75                  80

Tyr Val Lys Asp Pro Ala His Ser Trp Asn Leu Leu Ala Gln Glu Val
            85                  90                  95

Thr Val Val Glu Gly Gln Glu Ala Val Leu Pro Cys Leu Ile Thr Asp
            100                 105                 110

Pro Ala Leu Lys Asp Ser Val Ser Leu Met Arg Glu Gly Gly Arg Gln
        115                 120                 125

Val Leu Arg Lys Thr Val Tyr Phe Phe Ser Pro Trp Arg Gly Phe Ile
    130                 135                 140

Ile Arg Lys Ala Lys Val Leu Asp Ser Asn Thr Tyr Val Cys Lys Thr
145                 150                 155                 160

Met Val Asn Gly Arg Glu Ser Thr Ser Thr Gly Ile Trp Leu Lys Val
            165                 170                 175

Asn Arg Val His Pro Glu Pro Pro Gln Ile Lys Leu Glu Pro Ser Lys
            180                 185                 190

Leu Val Arg Ile Arg Gly Glu Ala Ala Gln Ile Val Cys Ser Ala Thr
        195                 200                 205

Asn Ala Glu Val Gly Phe Asn Val Ile Leu Lys Arg Gly Asp Thr Lys
    210                 215                 220

Leu Glu Ile Pro Leu Asn Ser Asp Phe Gln Asp Asn Tyr Tyr Lys Lys
225                 230                 235                 240

Val Arg Ala Leu Ser Leu Asn Ala Val Asp Phe Gln Asp Ala Gly Ile
            245                 250                 255

Tyr Ser Cys Val Ala Ser Asn Asp Val Gly Thr Arg Thr Ala Thr Met
```

```
                    260                 265                 270
Asn Phe Gln Val Val Glu Ser Ala Tyr Leu Asn Leu Thr Ser Glu Gln
                275                 280                 285

Ser Leu Leu Gln Glu Val Ser Val Gly Asp Ser Leu Ile Leu Thr Val
            290                 295                 300

His Ala Asp Ala Tyr Pro Ser Ile Gln His Tyr Asn Trp Thr Tyr Leu
305                 310                 315                 320

Gly Pro Phe Phe Glu Asp Gln Arg Lys Leu Glu Phe Ile Thr Gln Arg
                325                 330                 335

Ala Ile Tyr Arg Tyr Thr Phe Lys Leu Phe Leu Asn Arg Val Lys Ala
            340                 345                 350

Ser Glu Ala Gly Gln Tyr Phe Leu Met Ala Gln Asn Lys Ala Gly Trp
                355                 360                 365

Asn Asn Leu Thr Phe Glu Leu Thr Leu Arg Tyr Pro Pro Glu Val Ser
370                 375                 380

Val Thr Trp Met Pro Val Asn Gly Ser Asp Val Leu Phe Cys Asp Val
385                 390                 395                 400

Ser Gly Tyr Pro Gln Pro Ser Val Thr Trp Met Glu Cys Arg Gly His
                405                 410                 415

Thr Asp Arg Cys Asp Glu Ala Gln Ala Leu Gln Val Trp Asn Asp Thr
            420                 425                 430

His Pro Glu Val Leu Ser Gln Lys Pro Phe Asp Lys Val Ile Ile Gln
            435                 440                 445

Ser Gln Leu Pro Ile Gly Thr Leu Lys His Asn Met Thr Tyr Phe Cys
            450                 455                 460

Lys Thr His Asn Ser Val Gly Asn Ser Ser Gln Tyr Phe Arg Ala Val
465                 470                 475                 480

Ser Leu Gly Gln Ser Lys Gln Gly Phe Glu Pro Lys Ser Ser Asp Lys
                485                 490                 495

Thr His Thr Cys Pro Pro Cys Pro Ala Pro Glu Leu Leu Gly Gly Pro
            500                 505                 510

Ser Val Phe Leu Phe Pro Pro Lys Pro Lys Asp Thr Leu Met Ile Ser
            515                 520                 525

Arg Thr Pro Glu Val Thr Cys Val Val Val Asp Val Ser His Glu Asp
530                 535                 540

Pro Glu Val Lys Phe Asn Trp Tyr Val Asp Gly Val Glu Val His Asn
545                 550                 555                 560

Ala Lys Thr Lys Pro Arg Glu Glu Gln Tyr Asn Ser Thr Tyr Arg Val
                565                 570                 575

Val Ser Val Leu Thr Val Leu His Gln Asp Trp Leu Asn Gly Lys Glu
            580                 585                 590

Tyr Lys Cys Lys Val Ser Asn Lys Ala Leu Pro Ala Pro Ile Glu Lys
            595                 600                 605

Thr Ile Ser Lys Ala Lys Gly Gln Pro Arg Glu Pro Gln Val Tyr Thr
            610                 615                 620

Leu Pro Pro Ser Arg Asp Glu Leu Thr Lys Asn Gln Val Ser Leu Thr
625                 630                 635                 640

Cys Leu Val Lys Gly Phe Tyr Pro Ser Asp Ile Ala Val Glu Trp Glu
                645                 650                 655

Ser Asn Gly Gln Pro Glu Asn Asn Tyr Lys Thr Thr Pro Pro Val Leu
            660                 665                 670

Asp Ser Asp Gly Ser Phe Phe Leu Tyr Ser Lys Leu Thr Val Asp Lys
            675                 680                 685
```

```
Ser Arg Trp Gln Gln Gly Asn Val Phe Ser Cys Ser Val Met His Glu
    690                 695                 700

Ala Leu His Asn His Tyr Thr Gln Lys Ser Leu Ser Leu Ser Pro Gly
705                 710                 715                 720

Lys

<210> SEQ ID NO 35
<211> LENGTH: 746
<212> TYPE: PRT
<213> ORGANISM: Artificial Sequence
<220> FEATURE:
<223> OTHER INFORMATION: hCSF1R-ECD.512-Fc with signal peptide and GS
      linker

<400> SEQUENCE: 35

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
                100                 105                 110

Gln Glu Val Val Val Phe Glu Asp Gln Asp Ala Leu Leu Pro Cys Leu
            115                 120                 125

Leu Thr Asp Pro Val Leu Glu Ala Gly Val Ser Leu Val Arg Val Arg
130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
            195                 200                 205

Pro Ala Glu Leu Val Arg Ile Arg Gly Glu Ala Ala Gln Ile Val Cys
210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
            275                 280                 285

Thr Ser Met Phe Phe Arg Val Val Glu Ser Ala Tyr Leu Asn Leu Ser
        290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
```

```
                    325                 330                 335
Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
            355                 360                 365

Pro Arg Leu Lys Pro Ser Glu Ala Gly Arg Tyr Ser Phe Leu Ala Arg
        370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
    450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
            500                 505                 510

Gly Phe Glu Pro Lys Ser Ser Asp Lys Thr His Thr Cys Pro Pro Cys
        515                 520                 525

Pro Ala Pro Glu Leu Leu Gly Gly Pro Ser Val Phe Leu Phe Pro Pro
    530                 535                 540

Lys Pro Lys Asp Thr Leu Met Ile Ser Arg Thr Pro Glu Val Thr Cys
545                 550                 555                 560

Val Val Val Asp Val Ser His Glu Asp Pro Glu Val Lys Phe Asn Trp
                565                 570                 575

Tyr Val Asp Gly Val Glu Val His Asn Ala Lys Thr Lys Pro Arg Glu
            580                 585                 590

Glu Gln Tyr Asn Ser Thr Tyr Arg Val Val Ser Val Leu Thr Val Leu
        595                 600                 605

His Gln Asp Trp Leu Asn Gly Lys Glu Tyr Lys Cys Lys Val Ser Asn
    610                 615                 620

Lys Ala Leu Pro Ala Pro Ile Glu Lys Thr Ile Ser Lys Ala Lys Gly
625                 630                 635                 640

Gln Pro Arg Glu Pro Gln Val Tyr Thr Leu Pro Pro Ser Arg Asp Glu
                645                 650                 655

Leu Thr Lys Asn Gln Val Ser Leu Thr Cys Leu Val Lys Gly Phe Tyr
            660                 665                 670

Pro Ser Asp Ile Ala Val Glu Trp Glu Ser Asn Gly Gln Pro Glu Asn
        675                 680                 685

Asn Tyr Lys Thr Thr Pro Pro Val Leu Asp Ser Asp Gly Ser Phe Phe
    690                 695                 700

Leu Tyr Ser Lys Leu Thr Val Asp Lys Ser Arg Trp Gln Gln Gly Asn
705                 710                 715                 720

Val Phe Ser Cys Ser Val Met His Glu Ala Leu His Asn His Tyr Thr
                725                 730                 735

Gln Lys Ser Leu Ser Leu Ser Pro Gly Lys
            740                 745
```

<210> SEQ ID NO 36
<211> LENGTH: 740
<212> TYPE: PRT
<213> ORGANISM: Artificial Sequence
<220> FEATURE:
<223> OTHER INFORMATION: hCSF1R-ECD.506-Fc with signal peptide and GS
      linker

<400> SEQUENCE: 36

```
Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
        50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
            115                 120                 125

Leu Thr Asp Pro Val Leu Glu Ala Gly Val Ser Leu Val Arg Val Arg
        130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
            195                 200                 205

Pro Ala Glu Leu Val Arg Ile Arg Gly Glu Ala Ala Gln Ile Val Cys
        210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
            275                 280                 285

Thr Ser Met Phe Phe Arg Val Val Glu Ser Ala Tyr Leu Asn Leu Ser
        290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
            355                 360                 365
```

```
Pro Arg Leu Lys Pro Ser Glu Ala Gly Arg Tyr Ser Phe Leu Ala Arg
        370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
    450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Gly Phe Glu Pro Lys Ser
            500                 505                 510

Ser Asp Lys Thr His Thr Cys Pro Pro Cys Pro Ala Pro Glu Leu Leu
        515                 520                 525

Gly Gly Pro Ser Val Phe Leu Phe Pro Pro Lys Pro Lys Asp Thr Leu
    530                 535                 540

Met Ile Ser Arg Thr Pro Glu Val Thr Cys Val Val Val Asp Val Ser
545                 550                 555                 560

His Glu Asp Pro Glu Val Lys Phe Asn Trp Tyr Val Asp Gly Val Glu
                565                 570                 575

Val His Asn Ala Lys Thr Lys Pro Arg Glu Glu Gln Tyr Asn Ser Thr
            580                 585                 590

Tyr Arg Val Val Ser Val Leu Thr Val Leu His Gln Asp Trp Leu Asn
        595                 600                 605

Gly Lys Glu Tyr Lys Cys Lys Val Ser Asn Lys Ala Leu Pro Ala Pro
    610                 615                 620

Ile Glu Lys Thr Ile Ser Lys Ala Lys Gly Gln Pro Arg Glu Pro Gln
625                 630                 635                 640

Val Tyr Thr Leu Pro Pro Ser Arg Asp Glu Leu Thr Lys Asn Gln Val
                645                 650                 655

Ser Leu Thr Cys Leu Val Lys Gly Phe Tyr Pro Ser Asp Ile Ala Val
            660                 665                 670

Glu Trp Glu Ser Asn Gly Gln Pro Glu Asn Asn Tyr Lys Thr Thr Pro
        675                 680                 685

Pro Val Leu Asp Ser Asp Gly Ser Phe Phe Leu Tyr Ser Lys Leu Thr
    690                 695                 700

Val Asp Lys Ser Arg Trp Gln Gln Gly Asn Val Phe Ser Cys Ser Val
705                 710                 715                 720

Met His Glu Ala Leu His Asn His Tyr Thr Gln Lys Ser Leu Ser Leu
                725                 730                 735

Ser Pro Gly Lys
            740

<210> SEQ ID NO 37
<211> LENGTH: 745
<212> TYPE: PRT
<213> ORGANISM: Artificial Sequence
<220> FEATURE:
<223> OTHER INFORMATION: mCSF1R-ECD.511-Fc with signal peptide
```

-continued

```
<400> SEQUENCE: 37

Met Glu Leu Gly Pro Leu Val Leu Leu Leu Ala Thr Val Trp His
1               5                   10                  15

Gly Gln Gly Ala Pro Val Ile Glu Pro Ser Gly Pro Glu Leu Val
                20                  25                  30

Glu Pro Gly Glu Thr Val Thr Leu Arg Cys Val Ser Asn Gly Ser Val
                35                  40                  45

Glu Trp Asp Gly Pro Ile Ser Pro Tyr Trp Thr Leu Asp Pro Glu Ser
        50                  55                  60

Pro Gly Ser Thr Leu Thr Thr Arg Asn Ala Thr Phe Lys Asn Thr Gly
65                  70                  75                  80

Thr Tyr Arg Cys Thr Glu Leu Glu Asp Pro Met Ala Gly Ser Thr Thr
                85                  90                  95

Ile His Leu Tyr Val Lys Asp Pro Ala His Ser Trp Asn Leu Leu Ala
                100                 105                 110

Gln Glu Val Thr Val Val Glu Gly Gln Glu Ala Val Leu Pro Cys Leu
                115                 120                 125

Ile Thr Asp Pro Ala Leu Lys Asp Ser Val Ser Leu Met Arg Glu Gly
130                 135                 140

Gly Arg Gln Val Leu Arg Lys Thr Val Tyr Phe Phe Ser Pro Trp Arg
145                 150                 155                 160

Gly Phe Ile Ile Arg Lys Ala Lys Val Leu Asp Ser Asn Thr Tyr Val
                165                 170                 175

Cys Lys Thr Met Val Asn Gly Arg Glu Ser Thr Ser Thr Gly Ile Trp
                180                 185                 190

Leu Lys Val Asn Arg Val His Pro Glu Pro Pro Gln Ile Lys Leu Glu
                195                 200                 205

Pro Ser Lys Leu Val Arg Ile Arg Gly Glu Ala Ala Gln Ile Val Cys
210                 215                 220

Ser Ala Thr Asn Ala Glu Val Gly Phe Asn Val Ile Leu Lys Arg Gly
225                 230                 235                 240

Asp Thr Lys Leu Glu Ile Pro Leu Asn Ser Asp Phe Gln Asp Asn Tyr
                245                 250                 255

Tyr Lys Lys Val Arg Ala Leu Ser Leu Asn Ala Val Asp Phe Gln Asp
                260                 265                 270

Ala Gly Ile Tyr Ser Cys Val Ala Ser Asn Asp Val Gly Thr Arg Thr
                275                 280                 285

Ala Thr Met Asn Phe Gln Val Val Glu Ser Ala Tyr Leu Asn Leu Thr
                290                 295                 300

Ser Glu Gln Ser Leu Leu Gln Glu Val Ser Val Gly Asp Ser Leu Ile
305                 310                 315                 320

Leu Thr Val His Ala Asp Ala Tyr Pro Ser Ile Gln His Tyr Asn Trp
                325                 330                 335

Thr Tyr Leu Gly Pro Phe Phe Glu Asp Gln Arg Lys Leu Glu Phe Ile
                340                 345                 350

Thr Gln Arg Ala Ile Tyr Arg Tyr Thr Phe Lys Leu Phe Leu Asn Arg
                355                 360                 365

Val Lys Ala Ser Glu Ala Gly Gln Tyr Phe Leu Met Ala Gln Asn Lys
                370                 375                 380

Ala Gly Trp Asn Asn Leu Thr Phe Glu Leu Thr Leu Arg Tyr Pro Pro
385                 390                 395                 400

Glu Val Ser Val Thr Trp Met Pro Val Asn Gly Ser Asp Val Leu Phe
                405                 410                 415
```

```
Cys Asp Val Ser Gly Tyr Pro Gln Pro Ser Val Thr Trp Met Glu Cys
            420                 425                 430

Arg Gly His Thr Asp Arg Cys Asp Glu Ala Gln Ala Leu Gln Val Trp
        435                 440                 445

Asn Asp Thr His Pro Glu Val Leu Ser Gln Lys Pro Phe Asp Lys Val
    450                 455                 460

Ile Ile Gln Ser Gln Leu Pro Ile Gly Thr Leu Lys His Asn Met Thr
465                 470                 475                 480

Tyr Phe Cys Lys Thr His Asn Ser Val Gly Asn Ser Ser Gln Tyr Phe
                485                 490                 495

Arg Ala Val Ser Leu Gly Gln Ser Lys Gln Leu Pro Asp Glu Ser Gly
            500                 505                 510

Phe Glu Pro Lys Ser Ser Asp Lys Thr His Thr Cys Pro Pro Cys Pro
        515                 520                 525

Ala Pro Glu Leu Leu Gly Gly Pro Ser Val Phe Leu Phe Pro Pro Lys
    530                 535                 540

Pro Lys Asp Thr Leu Met Ile Ser Arg Thr Pro Glu Val Thr Cys Val
545                 550                 555                 560

Val Val Asp Val Ser His Glu Asp Pro Glu Val Lys Phe Asn Trp Tyr
                565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
        595                 600                 605

Gln Asp Trp Leu Asn Gly Lys Glu Tyr Lys Cys Lys Val Ser Asn Lys
    610                 615                 620

Ala Leu Pro Ala Pro Ile Glu Lys Thr Ile Ser Lys Ala Lys Gly Gln
625                 630                 635                 640

Pro Arg Glu Pro Gln Val Tyr Thr Leu Pro Pro Ser Arg Asp Glu Leu
                645                 650                 655

Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
        675                 680                 685

Tyr Lys Thr Thr Pro Pro Val Leu Asp Ser Asp Gly Ser Phe Phe Leu
    690                 695                 700

Tyr Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly Lys
            740                 745

<210> SEQ ID NO 38
<211> LENGTH: 740
<212> TYPE: PRT
<213> ORGANISM: Artificial Sequence
<220> FEATURE:
<223> OTHER INFORMATION: mCSF1R-ECD.506-Fc with signal peptide and GS
      linker

<400> SEQUENCE: 38

Met Glu Leu Gly Pro Pro Leu Val Leu Leu Leu Ala Thr Val Trp His
1               5                   10                  15

Gly Gln Gly Ala Pro Val Ile Glu Pro Ser Gly Pro Glu Leu Val Val
            20                  25                  30
```

-continued

Glu Pro Gly Glu Thr Val Thr Leu Arg Cys Val Ser Asn Gly Ser Val
    35                  40                  45

Glu Trp Asp Gly Pro Ile Ser Pro Tyr Trp Thr Leu Asp Pro Glu Ser
50                  55                  60

Pro Gly Ser Thr Leu Thr Thr Arg Asn Ala Thr Phe Lys Asn Thr Gly
65                  70                  75                  80

Thr Tyr Arg Cys Thr Glu Leu Glu Asp Pro Met Ala Gly Ser Thr Thr
                85                  90                  95

Ile His Leu Tyr Val Lys Asp Pro Ala His Ser Trp Asn Leu Leu Ala
            100                 105                 110

Gln Glu Val Thr Val Val Glu Gly Gln Glu Ala Val Leu Pro Cys Leu
        115                 120                 125

Ile Thr Asp Pro Ala Leu Lys Asp Ser Val Ser Leu Met Arg Glu Gly
    130                 135                 140

Gly Arg Gln Val Leu Arg Lys Thr Val Tyr Phe Phe Ser Pro Trp Arg
145                 150                 155                 160

Gly Phe Ile Ile Arg Lys Ala Lys Val Leu Asp Ser Asn Thr Tyr Val
                165                 170                 175

Cys Lys Thr Met Val Asn Gly Arg Glu Ser Thr Ser Thr Gly Ile Trp
            180                 185                 190

Leu Lys Val Asn Arg Val His Pro Glu Pro Pro Gln Ile Lys Leu Glu
        195                 200                 205

Pro Ser Lys Leu Val Arg Ile Arg Gly Glu Ala Ala Gln Ile Val Cys
    210                 215                 220

Ser Ala Thr Asn Ala Glu Val Gly Phe Asn Val Ile Leu Lys Arg Gly
225                 230                 235                 240

Asp Thr Lys Leu Glu Ile Pro Leu Asn Ser Asp Phe Gln Asp Asn Tyr
                245                 250                 255

Tyr Lys Lys Val Arg Ala Leu Ser Leu Asn Ala Val Asp Phe Gln Asp
            260                 265                 270

Ala Gly Ile Tyr Ser Cys Val Ala Ser Asn Asp Val Gly Thr Arg Thr
        275                 280                 285

Ala Thr Met Asn Phe Gln Val Val Glu Ser Ala Tyr Leu Asn Leu Thr
    290                 295                 300

Ser Glu Gln Ser Leu Leu Gln Glu Val Ser Val Gly Asp Ser Leu Ile
305                 310                 315                 320

Leu Thr Val His Ala Asp Ala Tyr Pro Ser Ile Gln His Tyr Asn Trp
                325                 330                 335

Thr Tyr Leu Gly Pro Phe Phe Glu Asp Gln Arg Lys Leu Glu Phe Ile
            340                 345                 350

Thr Gln Arg Ala Ile Tyr Arg Tyr Thr Phe Lys Leu Phe Leu Asn Arg
        355                 360                 365

Val Lys Ala Ser Glu Ala Gly Gln Tyr Phe Leu Met Ala Gln Asn Lys
    370                 375                 380

Ala Gly Trp Asn Asn Leu Thr Phe Glu Leu Thr Leu Arg Tyr Pro Pro
385                 390                 395                 400

Glu Val Ser Val Thr Trp Met Pro Val Asn Gly Ser Asp Val Leu Phe
                405                 410                 415

Cys Asp Val Ser Gly Tyr Pro Gln Pro Ser Val Thr Trp Met Glu Cys
            420                 425                 430

Arg Gly His Thr Asp Arg Cys Asp Glu Ala Gln Ala Leu Gln Val Trp
        435                 440                 445

Asn Asp Thr His Pro Glu Val Leu Ser Gln Lys Pro Phe Asp Lys Val
    450                 455                 460

```
Ile Ile Gln Ser Gln Leu Pro Ile Gly Thr Leu Lys His Asn Met Thr
465                 470                 475                 480

Tyr Phe Cys Lys Thr His Asn Ser Val Gly Asn Ser Ser Gln Tyr Phe
            485                 490                 495

Arg Ala Val Ser Leu Gly Gln Ser Lys Gln Gly Phe Glu Pro Lys Ser
            500                 505                 510

Ser Asp Lys Thr His Thr Cys Pro Pro Cys Pro Ala Pro Glu Leu Leu
            515                 520                 525

Gly Gly Pro Ser Val Phe Leu Phe Pro Pro Lys Pro Lys Asp Thr Leu
            530                 535                 540

Met Ile Ser Arg Thr Pro Glu Val Thr Cys Val Val Val Asp Val Ser
545                 550                 555                 560

His Glu Asp Pro Glu Val Lys Phe Asn Trp Tyr Val Asp Gly Val Glu
            565                 570                 575

Val His Asn Ala Lys Thr Lys Pro Arg Glu Glu Gln Tyr Asn Ser Thr
            580                 585                 590

Tyr Arg Val Val Ser Val Leu Thr Val Leu His Gln Asp Trp Leu Asn
            595                 600                 605

Gly Lys Glu Tyr Lys Cys Lys Val Ser Asn Lys Ala Leu Pro Ala Pro
            610                 615                 620

Ile Glu Lys Thr Ile Ser Lys Ala Lys Gly Gln Pro Arg Glu Pro Gln
625                 630                 635                 640

Val Tyr Thr Leu Pro Pro Ser Arg Asp Glu Leu Thr Lys Asn Gln Val
            645                 650                 655

Ser Leu Thr Cys Leu Val Lys Gly Phe Tyr Pro Ser Asp Ile Ala Val
            660                 665                 670

Glu Trp Glu Ser Asn Gly Gln Pro Glu Asn Asn Tyr Lys Thr Thr Pro
            675                 680                 685

Pro Val Leu Asp Ser Asp Gly Ser Phe Phe Leu Tyr Ser Lys Leu Thr
            690                 695                 700

Val Asp Lys Ser Arg Trp Gln Gln Gly Asn Val Phe Ser Cys Ser Val
705                 710                 715                 720

Met His Glu Ala Leu His Asn His Tyr Thr Gln Lys Ser Leu Ser Leu
            725                 730                 735

Ser Pro Gly Lys
            740
```

TREATMENT OF OSTEOLYTIC DISORDERS AND CANCER USING CSF1R EXTRACELLULAR DOMAIN FUSION MOLECULES

This application claims priority to U.S. Provisional Patent Application No. 61/118,427, filed on Nov. 26, 2008, and which is incorporated herein by reference in its entirety.

TECHNICAL FIELD

The present invention relates to methods of treating osteolytic bone loss, cancer metastasis, cancer metastasis-induced osteolytic bone loss, and tumor growth using colony stimulating factor 1 receptor (CSF1R) extracellular domains (ECDs) that have been engineered to contain a fusion partner. The invention further provides specific CSF1R ECD fusion molecules that exhibit improved therapeutic properties. The invention also relates to polypeptide and polynucleotide sequences, vectors, host cells, and compositions comprising or encoding such molecules. The invention also relates to methods of making and using CSF1R ECD fusion molecules.

BACKGROUND AND SUMMARY OF THE INVENTION

Bone remodeling is a continuous process that maintains skeletal integrity through the coordinated activities of two cell populations: osteoclasts, which are responsible for bone resorption (osteolysis), and osteoblasts, which are responsible for bone formation. In order to maintain bone homeostasis, the activity of osteoclasts and osteoblasts must be tightly regulated. Dysregulation of osteoclast activity is associated with several forms of human disease, including osteolytic bone loss due to increased osteoclast activity and osteopetrosis (excessive bone accumulation) due to decreased osteoclast activity. Osteolytic bone loss may also be caused by cancer metastasis to bone. Breast, lung, and prostate cancer are the most common malignancies in adults, and they are also the most common tumor types to metastasize to bone. Kidney, thyroid, and melanoma are other common forms of cancer that metastasize to bone. Tumor cells often secrete osteoclast-activating factors, including the colony stimulating factor 1 ligand (referred to herein as CSF1; also referred to in the art as MCSF and MGC31930) and the receptor activator of NF-kB ligand (RANKL), that stimulate osteoclast activity and induce osteolytic bone loss. As a result, bone metastasis is associated with fractures, pain, spinal cord compression, and hypercalcemia. Therefore, therapeutic agents that treat osteolytic bone loss, inhibit metastasis, and/or prevent metastasis-induced osteoclast activation would be expected to offer significant clinical benefits to patients.

The colony stimulating factor 1 receptor (referred to herein as CSF1R; also referred to in the art as FMS, FIM2, C-FMS, and CD115) is a single-pass transmembrane receptor with an N-terminal extracellular domain (ECD) and a C-terminal intracellular domain with tyrosine kinase activity. Ligand binding of CSF1 or the interleukin 34 ligand (referred to herein as IL34; also referred to in the art as C16orf77 and MGC34647) to CSF1R leads to receptor dimerization, upregulation of CSF1R protein tyrosine kinase activity, phosphorylation of CSF1R tyrosine residues, and downstream signaling events. Both CSF1 and IL34 stimulate monocyte survival, proliferation, and differentiation into macrophages. However, IL34 was discovered recently, and its overall functions have not been fully established.

Dysregulation of CSF1R activity may result in an imbalance in the levels and/or activities of macrophage and osteoclast cell populations, which may lead to disease-associated pathology. Based on their known and suspected contributions to human disease, both CSF1R and CSF1 have been identified as potential therapeutic targets for osteolytic bone loss and cancer. Indeed, CSF1R and CSF1 antagonists such as antibodies directed against CSF1R or CSF1 (see e.g., WO 2007/081879), antisense- and siRNA-mediated silencing of CSF1R or CSF1 expression (see e.g., WO 2007/081879), soluble forms of the CSF1R (see e.g., WO 2007/081879), and small molecule inhibitors of CSF1R tyrosine kinase activity (see e.g., Ohno et al., *Molecular Cancer Therapy* 5(11): 2634-2643 (2006); Murray et al., *Clinical & Experimental Metastasis* 20:757-766 (2003); and Conway et al., *PNAS* 102(44):16078-16083 (2005)), have been proposed for targeting osteolytic bone loss. Despite the proposed utility of such CSF1R and CSF1 antagonists, there remains a need in the art for the identification of additional agents with a demonstrated ability to inhibit disease pathology in vivo, such as osteolytic bone loss, cancer metastasis, cancer metastasis-induced osteolytic bone loss, and tumor growth.

To date, we are not aware of any demonstration of a CSF1R ECD fusion molecule shown to be effective at treating osteolytic bone loss, cancer metastasis, cancer metastasis-induced osteolytic bone loss, or tumor growth in vivo. As described herein, the inventors have found that CSF1R ECD fusion molecules of the invention inhibit osteolytic bone loss in vivo models, including osteolytic bone loss resulting from cancer metastasis to bone (See Examples 8 and 10). Furthermore, the inventors have also shown that CSF1R ECD fusion molecules inhibit cancer metastasis in vivo (See Example 9). In certain cancers, the inventors have found that CSF1R ECD fusion molecules directly inhibit primary tumor growth in vivo (See Example 9).

In addition, the inventors have found that certain of the CSF1R ECD fusion molecules of the invention exhibit improved properties, including improvements to therapeutically relevant properties. For example, the inventors have found that expression of CSF1R ECD fusion molecules in CHO cells results in more highly sialylated CSF1R ECD fusion molecules, which are more stable than such fusion molecules produced in 293-6E cells. Also, the inventors have found that a CSF1R ECD fusion molecule wherein the CSF1R ECD has the amino acid sequence of SEQ ID NO.:2 (amino acids 20-506 of the human CSF1R protein) binds the CSF1R ligands CSF1 and IL34 more tightly and more effectively inhibits monocyte growth in an in vitro assay than a full-length CSF1R ECD fusion molecule wherein the CSF1R ECD has the amino acid sequence of SEQ ID NO.:1 (amino acids 20-512 of the human CSF1R protein). Thus, this CSF1R ECD fusion molecule provides a particularly attractive therapeutic molecule.

Accordingly, the present invention provides methods and compositions for treating osteolytic disorders, including but not limited to, osteolytic bone loss. Osteolytic bone loss may include cancer metastasis-induced osteolytic bone loss. The present invention also provides methods and compositions for inhibiting cancer metastasis and inhibiting CSF1R-dependent tumor growth.

The invention includes a method of treating osteolytic bone loss in a patient comprising administering to the patient a therapeutically effective amount of a CSF1R ECD fusion molecule, wherein the CSF1R ECD fusion molecule comprises a CSF1R ECD and one or more fusion partners. The invention further includes a method of treating osteolytic bone loss in a patient comprising administering to the patient a therapeutically effective amount of a CSF1R ECD fusion molecule, wherein the amino acid sequence of the CSF1R ECD consists of SEQ ID NO.:2, SEQ ID NO.:26, or SEQ ID NO.:1. In certain embodiments, the one or more fusion partners are selected from an Fc, albumin, and polyethylene glycol. In certain other embodiments, the one or more fusion partners of the are selected from an Fc alone, polyethylene glycol alone, and an Fc and polyethylene glycol. The invention further includes the method of treating osteolytic bone loss in a patient comprising administering to the patient a therapeutically effective amount of a CSF1R ECD fusion molecule, wherein the one or more fusion partners is an Fc, and wherein the amino acid sequence of the CSF1R ECD fusion molecule consists of SEQ ID NO.:6 or SEQ ID NO.:5. The invention also includes the method of treating osteolytic bone loss in a patient comprising administering to the patient a therapeutically effective amount of a CSF1R ECD fusion molecule, wherein the one or more fusion partners is an Fc, and wherein the amino acid sequence of the CSF1R ECD fusion molecule consists of SEQ ID NO.:6 or SEQ ID NO.:5, and wherein the CSF1R ECD fusion molecule is glycosylated or sialylated. The invention further includes the method of treating osteolytic bone loss in a patient comprising administering to the patient a therapeutically effective amount of a CSF1R ECD fusion molecule, wherein the CSF1R ECD fusion molecule comprises a CSF1R ECD and one or more fusion partners, and wherein the CSF1R ECD fusion molecule is produced from a CHO cell. The invention further includes the method of treating osteolytic bone loss in a patient comprising administering to the patient a therapeutically effective amount of a CSF1R ECD fusion molecule, wherein the osteolytic bone loss is cancer metastasis-induced.

The invention includes a method of inhibiting cancer metastasis in a patient comprising administering to the patient a therapeutically effective amount of a CSF1R ECD fusion molecule, wherein the CSF1R ECD fusion molecule comprises a CSF1R ECD and one or more fusion partners. The invention further includes a method of inhibiting cancer metastasis in a patient comprising administering to the patient a therapeutically effective amount of a CSF1R ECD fusion molecule, wherein the amino acid sequence of the CSF1R ECD consists of SEQ ID NO.:2, SEQ ID NO.:26, or SEQ ID NO.:1. In certain embodiments, the one or more fusion partners are selected from an Fc, albumin, and polyethylene glycol. In certain other embodiments, the one or more fusion partners of the are selected from an Fc alone, polyethylene glycol alone, and an Fc and polyethylene glycol. The invention further includes the method of inhibiting cancer metastasis in a patient comprising administering to the patient a therapeutically effective amount of a CSF1R ECD fusion molecule, wherein the one or more fusion partners is an Fc, and wherein the amino acid sequence of the CSF1R ECD fusion molecule consists of SEQ ID NO.:6 or SEQ ID NO.:5. The invention also includes the method of inhibiting cancer metastasis in a patient comprising administering to the patient a therapeutically effective amount of a CSF1R ECD fusion molecule, wherein the one or more fusion partners is an Fc, and wherein the amino acid sequence of the CSF1R ECD fusion molecule consists of SEQ ID NO.:6 or SEQ ID NO.:5, and wherein the CSF1R ECD fusion molecule is glycosylated or sialylated. The invention further includes the method of inhibiting cancer metastasis in a patient administering to the patient a therapeutically effective amount of a CSF1R ECD fusion molecule, wherein the CSF1R ECD fusion molecule comprises a CSF1R ECD and one or more fusion partners, and wherein the CSF1R ECD fusion molecule is produced from a CHO cell. The invention further includes the method of inhibiting cancer metastasis in a patient comprising administering to the patient a therapeutically effective amount of a CSF1R ECD fusion molecule, wherein the CSF1R ECD fusion molecule comprises a CSF1R ECD and one or more fusion partners, and wherein the cancer is selected from breast cancer, prostate cancer, lung cancer, kidney cancer, thyroid cancer, melanoma, follicular lymphoma, carcinoma with p53 mutations, colon cancer, cardiac tumor, pancreatic cancer, retinoblastoma, glioblastoma, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, Kaposi's sarcoma, ovarian cancer, leukemia, acute leukemia, chronic leukemia, myelodysplastic syndrome polycythemia vera, multiple myeloma, Waldenström's macroglobulinemia, and heavy chain disease. The invention further includes the method of inhibiting cancer metastasis in a patient comprising administering to the patient a therapeutically effective amount of a CSF1R ECD fusion molecule, wherein the CSF1R ECD fusion molecule comprises a CSF1R ECD and one or more fusion partners, and wherein the cancer is breast cancer.

The invention includes a method of treating CSF1- and/or IL34-dependent tumor growth in a patient comprising administering to the patient a therapeutically effective amount of a CSF1R ECD fusion molecule, wherein the CSF1R ECD fusion molecule comprises a CSF1R ECD and one or more fusion partners. The invention further includes a method of method of treating CSF1- and/or IL34-dependent tumor growth in a patient comprising administering to the patient a therapeutically effective amount of a CSF1R ECD fusion molecule, wherein the amino acid sequence of the CSF1R ECD consists of SEQ ID NO.:2, SEQ ID NO.:26, or SEQ ID NO.:1. In certain embodiments, the one or more fusion partners are selected from an Fc, albumin, and polyethylene glycol. In certain other embodiments, the one or more fusion partners of the are selected from an Fc alone, polyethylene glycol alone, and an Fc and polyethylene glycol. The invention further includes the method of treating CSF1- and/or IL34-dependent tumor growth in a patient comprising administering to the patient a therapeutically effective amount of a CSF1R ECD fusion molecule, wherein the one or more fusion partners is an Fc, and wherein the amino acid sequence of the CSF1R ECD fusion molecule consists of SEQ ID NO.:6 or SEQ ID NO.:5. The invention also includes the method of method of treating CSF1- and/or IL34-dependent tumor growth in a patient comprising administering to the patient a therapeutically effective amount of a CSF1R ECD fusion molecule, wherein the one or more fusion partners is an Fc, and wherein the amino acid sequence of the CSF1R ECD fusion molecule consists of SEQ ID NO.:6 or SEQ ID NO.:5, and wherein the CSF1R ECD fusion molecule is glycosylated or sialylated. The invention further includes the method of method of treating CSF1- and/or IL34-dependent tumor growth in a patient comprising administering to the patient a therapeutically effective amount of a CSF1R ECD fusion molecule, wherein the CSF1R ECD fusion molecule comprises a CSF1R ECD and one or more fusion partners, and wherein the CSF1R ECD fusion molecule is produced from a CHO cell. The invention further includes a method of method of treating CSF1- and/or IL34-dependent tumor growth in a patient comprising administering to the patient a therapeutically effective amount of a CSF1R ECD fusion molecule, wherein the tumor is a solid tumor or a leukemic tumor. The invention further includes a method of method of treating CSF1- and/or IL34-dependent tumor growth in a patient comprising administering to the patient a therapeutically effective amount of a CSF1R ECD fusion molecule, wherein the tumor is a solid tumor or a leukemic tumor, and wherein the solid tumor is selected from sarcoma and carcinoma.

The invention includes a method of treating osteolytic bone loss in a patient who has and/or has been diagnosed with osteolytic bone loss comprising administering to the patient a therapeutically effective amount of a CSF1R ECD fusion molecule, wherein the CSF1R ECD fusion molecule comprises a CSF1R ECD and one or more fusion partners. The invention further includes a method of treating osteolytic bone loss in a patient who has and/or has been diagnosed with osteolytic bone loss comprising administering to the patient a therapeutically effective amount of a CSF1R ECD fusion molecule, wherein the amino acid sequence of the CSF1R ECD consists of SEQ ID NO.:2, SEQ ID NO.:26, or SEQ ID NO.:1. In certain embodiments, the one or more fusion partners are selected from an Fc, albumin, and polyethylene glycol. In certain other embodiments, the one or more fusion partners of the are selected from an Fc alone, polyethylene glycol alone, and an Fc and polyethylene glycol. The invention further includes the method of treating osteolytic bone loss in a patient who has and/or has been diagnosed with osteolytic bone loss comprising administering to the patient a therapeutically effective amount of a CSF1R ECD fusion molecule, wherein the one or more fusion partners is an Fc, and wherein the amino acid sequence of the CSF1R ECD fusion molecule consists of SEQ ID NO.:6 or SEQ ID NO.:5. The invention also includes the method of treating osteolytic bone loss in a patient who has and/or has been diagnosed with osteolytic bone loss comprising administering to the patient a therapeutically effective amount of a CSF1R ECD fusion molecule, wherein the one or more fusion partners is an Fc, and wherein the amino acid sequence of the CSF1R ECD fusion molecule consists of SEQ ID NO.:6 or SEQ ID NO.:5, and wherein the CSF1R ECD fusion molecule is glycosylated or sialylated. The invention further includes the method of treating osteolytic bone loss in a patient who has and/or has been diagnosed with osteolytic bone loss comprising administering to the patient a therapeutically effective amount of a CSF1R ECD fusion molecule, wherein the CSF1R ECD fusion molecule comprises a CSF1R ECD and one or more fusion partners, and wherein the CSF1R ECD fusion molecule is produced from a CHO cell. The invention further includes the method of treating osteolytic bone loss in a patient who has and/or has been diagnosed with osteolytic bone loss comprising administering to the patient a therapeutically effective amount of a CSF1R ECD fusion molecule, wherein the osteolytic bone loss is cancer metastasis-induced.

The invention includes a method of inhibiting cancer metastasis in a patient who has and/or has been diagnosed with cancer metastasis comprising administering to the patient a therapeutically effective amount of a CSF1R ECD fusion molecule, wherein the CSF1R ECD fusion molecule comprises a CSF1R ECD and one or more fusion partners. The invention further includes a method of inhibiting cancer metastasis in a patient who has and/or has been diagnosed with cancer metastasis comprising administering to the patient a therapeutically effective amount of a CSF1R ECD fusion molecule, wherein the amino acid sequence of the CSF1R ECD consists of SEQ ID NO.:2, SEQ ID NO.:26, or SEQ ID NO.:1. In some embodiments, the CSF1R ECD fusion molecule comprises SEQ ID NO.:2 (terminating at residue 506 of the human CSF1R ECD amino acid sequence) and excludes the last six C-terminal amino acid residues of SEQ ID NO:1 (corresponding to residues 507-512 of the human CSF1R ECD sequence). In such fusion molecules, any amino acid residues that follow the C-terminal residue of SEQ ID NO:2 do not begin with the amino acid sequence of residues 507-512 of SEQ ID NO:1 (THPPDE). Such fusion molecules may of course include the amino acid sequence THPPDE anywhere else in the amino acid sequence. In certain embodiments, the one or more fusion partners are selected from an Fc, albumin, and polyethylene glycol. In certain other embodiments, the one or more fusion partners of the are selected from an Fc alone, polyethylene glycol alone, and an Fc and polyethylene glycol. In some embodiments, one or more fusion partners is joined to the CSF1R ECD by a linker. In some such embodiments, the linker is a peptide consisting of the amino acid sequence glycine-serine. In some embodiments, the CSF1R ECD comprises a signal peptide. In some embodiments, the fusion molecule is glycosylated and/or sialylated. In some embodiments, the polypeptide portion of the fusion molecule is expressed in Chinese hamster ovary (CHO) cells. The invention further includes the method of inhibiting cancer metastasis in a patient who has and/or has been diagnosed with cancer metastasis comprising administering to the patient a therapeutically effective amount of a CSF1R ECD fusion molecule, wherein the one or more fusion partners is an Fc, and wherein the amino acid sequence of the CSF1R ECD fusion molecule comprises or consists of SEQ ID NO.:6 or SEQ ID NO.:5. In some embodiments, the CSF1R ECD comprises a signal peptide. In some embodiments, the fusion molecule is glycosylated and/or sialylated. In some embodiments, the polypeptide portion of the fusion molecule is expressed in Chinese hamster ovary (CHO) cells. The invention also includes the method of inhibiting cancer metastasis in a patient who has and/or has been diagnosed with cancer metastasis comprising administering to the patient a therapeutically effective amount of a CSF1R ECD fusion molecule, wherein the one or more fusion partners is an Fc, and wherein the amino acid sequence of the CSF1R ECD fusion molecule comprises or consists of SEQ ID NO.:6 or SEQ ID NO.:5, and wherein the CSF1R ECD fusion molecule is glycosylated or sialylated. In some embodiments, the CSF1R ECD comprises a signal peptide. In some embodiments, the polypeptide portion of the fusion molecule is expressed in Chinese hamster ovary (CHO) cells. The invention further includes the method of inhibiting cancer metastasis in a patient who has and/or has been diagnosed with cancer metastasis comprising administering to the patient a therapeutically effective amount of a CSF1R ECD fusion molecule, wherein the CSF1R ECD fusion molecule comprises a CSF1R ECD and one or more fusion partners, and wherein the CSF1R ECD fusion molecule is produced from a CHO cell. The invention further includes the method of inhibiting cancer metastasis in a patient who has and/or has been diagnosed with cancer metastasis comprising administering to the patient a therapeutically effective amount of a CSF1R ECD fusion molecule as described previously, and wherein the cancer is selected from breast cancer, prostate cancer, lung cancer, kidney cancer, thyroid cancer, melanoma, follicular lymphoma, carcinoma with p53 mutations, colon cancer, cardiac tumor, pancreatic cancer, retinoblastoma, glioblastoma, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, Kaposi's sarcoma, ovarian cancer, leukemia, acute leukemia, chronic leukemia, myelodysplastic syndrome polycythemia vera, multiple myeloma, Waldenström's macroglobulinemia, and heavy chain disease. The invention further includes the method of inhibiting cancer metastasis in a patient who has and/or has been diagnosed with cancer metastasis comprising administering to the patient a therapeutically effective amount of a CSF1R ECD fusion molecule as described previously, wherein the CSF1R ECD fusion molecule comprises a CSF1R ECD and one or more fusion partners, and wherein the cancer is breast cancer.

The invention includes a method of treating CSF1- and/or IL34-dependent tumor growth in a patient who has and/or has been diagnosed with CSF1- and/or IL34-dependent tumor growth comprising administering to the patient a therapeutically effective amount of a CSF1R ECD fusion molecule, wherein the CSF1R ECD fusion molecule comprises a CSF1R ECD and one or more fusion partners. The invention further includes a method of method of treating CSF1- and/or IL34-dependent tumor growth in a patient who has and/or has been diagnosed with CSF1- and/or IL34-dependent tumor growth comprising administering to the patient a therapeutically effective amount of a CSF1R ECD fusion molecule, wherein the amino acid sequence of the CSF1R ECD consists of SEQ ID NO.:2, SEQ ID NO.:26, or SEQ ID NO.:1. In some embodiments, the CSF1R ECD fusion molecule comprises SEQ ID NO.:2 (terminating at residue 506 of the human CSF1R ECD amino acid sequence) and excludes the last six C-terminal amino acid residues of SEQ ID NO:1 (corresponding to residues 507-512 of the sequence). In such fusion molecules, any amino acid residues that follow the C-terminal residue of SEQ ID NO:2 do not begin with the amino acid sequence of residues 507-512 of SEQ ID NO:1 (THPPDE). Such fusion molecules may of course include the amino acid sequence THPPDE anywhere else in the amino acid sequence. In certain embodiments, the one or more fusion partners are selected from an Fc, albumin, and polyethylene glycol. In certain other embodiments, the one or more fusion partners of the are selected from an Fc alone, polyethylene glycol alone, and an Fc and polyethylene glycol. In some embodiments, one or more fusion partners is joined to the CSF1R ECD by a linker. In some such embodiments, the linker is a peptide consisting of the amino acid sequence glycine-serine. In some embodiments, the CSF1R ECD comprises a signal peptide. In some embodiments, the fusion molecule is glycosylated and/or sialylated. In some embodiments, the polypeptide portion of the fusion molecule is expressed in Chinese hamster ovary (CHO) cells. The invention further includes the method of treating CSF1- and/or IL34-dependent tumor growth in a patient who has and/or has been diagnosed with CSF1- and/or IL34-dependent tumor growth comprising administering to the patient a therapeutically effective amount of a CSF1R ECD fusion molecule, wherein the one or more fusion partners is an Fc, and wherein the amino acid sequence of the CSF1R ECD fusion molecule comprises or consists of SEQ ID NO.:6 or SEQ ID NO.:5. In some embodiments, the CSF1R ECD comprises a signal peptide. In some embodiments, the fusion molecule is glycosylated and/or sialylated. In some embodiments, the polypeptide portion of the fusion molecule is expressed in Chinese hamster ovary (CHO) cells. The invention also includes the method of method of treating CSF1- and/or IL34-dependent tumor growth in a patient who has and/or has been diagnosed with CSF1- and/or IL34-dependent tumor growth comprising administering to the patient a therapeutically effective amount of a CSF1R ECD fusion molecule, wherein the one or more fusion partners is an Fc, and wherein the amino acid sequence of the CSF1R ECD fusion molecule comprises or consists of SEQ ID NO.:6 or SEQ ID NO.:5, and wherein the CSF1R ECD fusion molecule is glycosylated or sialylated. In some embodiments, the CSF1R ECD comprises a signal peptide. In some embodiments, the polypeptide portion of the fusion molecule is expressed in Chinese hamster ovary (CHO) cells. The invention further includes the method of method of treating CSF1- and/or IL34-dependent tumor growth in a patient who has and/or has been diagnosed with CSF1- and/or IL34-dependent tumor growth comprising administering to the patient a therapeutically effective amount of a CSF1R ECD fusion molecule, wherein the CSF1R ECD fusion molecule comprises a CSF1R ECD and one or more fusion partners, and wherein the CSF1R ECD fusion molecule is produced from a CHO cell. The invention further includes a method of method of treating CSF1- and/or IL34-dependent tumor growth in a patient who has and/or has been diagnosed with CSF1- and/or IL34-dependent tumor growth comprising administering to the patient a therapeutically effective amount of a CSF1R ECD fusion molecule as described previously, wherein the tumor is a solid tumor or a leukemic tumor. The invention further includes a method of method of treating CSF1- and/or IL34-dependent tumor growth in a patient who has and/or has been diagnosed with CSF1- and/or IL34-dependent tumor growth comprising administering to the patient a therapeutically effective amount of a CSF1R ECD fusion molecule as described previously, wherein the tumor is a solid tumor or a leukemic tumor, and wherein the solid tumor is selected from sarcoma and carcinoma.

The invention includes a CSF1R ECD fusion molecule comprising a CSF1R ECD and one or more fusion partners, wherein the amino acid sequence of the CSF1R ECD comprises SEQ ID NO.:2 and excludes the last six C-terminal amino acid residues of SEQ ID NO.:1. In such fusion molecules, any amino acid residues that follow the C-terminal residue of SEQ ID NO:2 do not begin with the amino acid sequence of residues 507-512 of SEQ ID NO:1 (THPPDE). Such fusion molecules may of course include the amino acid sequence THPPDE anywhere else in the amino acid sequence. In some such embodiments, the CSF1R ECD consists of SEQ ID NO:2.

In certain embodiments, the one or more fusion partners are selected from an Fc, albumin, and polyethylene glycol. In certain other embodiments, the one or more fusion partners of the are selected from an Fc alone, polyethylene glycol alone, and an Fc and polyethylene glycol. In some embodiments, the fusion molecule comprises a linker between the CSF1R ECD and one or more fusion partners. In some such embodiments, the linker is a peptide consisting of the amino acid sequence glycine-serine. In some embodiments, the CSF1R ECD comprises a signal peptide. In some embodiments, the fusion molecule is glycosylated and/or sialylated. In some embodiments, the polypeptide portion of the fusion molecule is expressed in Chinese hamster ovary (CHO) cells.

The invention also includes a CSF1R ECD fusion molecule comprising a CSF1R ECD and an Fc, wherein the amino acid sequence of the CSF1R ECD fusion molecule comprises SEQ ID NO.:6. The invention further includes the CSF1R ECD fusion comprising a CSF1R ECD and an Fc, wherein the amino acid sequence of the CSF1R ECD fusion molecule consists of SEQ ID NO.:6. In some such embodiments, the CSF1R ECD comprises a signal peptide. In some embodiments, the fusion molecule is glycosylated and/or sialylated. In some embodiments, the polypeptide portion of the fusion molecule is expressed in Chinese hamster ovary (CHO) cells.

The invention further includes a CSF1R ECD fusion molecule comprising a CSF1R ECD, an Fc, and polyethylene glycol, wherein the amino acid sequence of the CSF1R ECD fusion molecule comprises SEQ ID NO.:6. The invention further includes a CSF1R ECD fusion molecule comprising a CSF1R ECD, an Fc, and polyethylene glycol, wherein the amino acid sequence of the CSF1R ECD fusion molecule comprises SEQ ID NO.:6, and wherein the fusion molecule is glycosylated or sialylated. In some embodiments, the CSF1R ECD comprises a signal peptide. In some embodiments, the polypeptide portion of the fusion molecule is expressed in Chinese hamster ovary (CHO) cells.

The invention also includes a CSF1R ECD fusion molecule comprising a CSF1R ECD, an Fc, and polyethylene glycol, wherein the amino acid sequence of the CSF1R ECD fusion molecule consists of SEQ ID NO.:6. The invention also includes a CSF1R ECD fusion molecule comprising a CSF1R ECD, an Fc, and polyethylene glycol, wherein the amino acid sequence of the CSF1R ECD fusion molecule consists of SEQ ID NO.:6, and wherein the fusion molecule is glycosylated or sialylated. In some such embodiments, the polypeptide portion of the fusion molecule is expressed in Chinese hamster ovary (CHO) cells.

The invention further includes a pharmaceutical composition comprising any one of the above described CSF1R ECD fusion molecules and a pharmaceutically acceptable carrier.

The invention also includes a polynucleotide comprising a nucleic acid sequence that encodes any one of the above described CSF1R ECD fusion molecules. In some embodiments, the polynucleotide encodes a CSF1R ECD fusion molecule comprising a CSF1R ECD and one or more fusion partners, wherein the amino acid sequence of the CSF1R ECD comprises SEQ ID NO.:2 and excludes the last six C-terminal amino acid residues of SEQ ID NO.:1. The one or more fusion partners may include an Fc or albumin. The invention further includes a polynucleotide comprising a nucleic acid sequence that encodes a CSF1R ECD fusion molecule comprising a CSF1R ECD and one or more fusion partners, wherein the amino acid sequence of the CSF1R ECD fusion molecule comprises SEQ ID NO.:6. In some embodiments, the amino acid sequence encoded by the polynucleotide of the invention comprises a signal peptide amino acid sequence. In some embodiments, the polynucleotide encodes an amino acid sequence comprising SEQ ID NO:6 plus a signal peptide sequence, such as, for example, SEQ ID NO:16.

The invention further includes an expression vector comprising a polynucleotide as described above, encoding any one of the above described CSF1R ECD fusion molecules. The invention also includes a CHO cell comprising the expression vector comprising the polynucleotide encoding any one of the above described CSF1R ECD fusion molecules. For example, in some embodiments, the CHO cell comprises a vector comprising a polynucleotide sequence that encodes the amino acid sequence of SEQ ID NO:6 plus a signal peptide amino acid sequence, such as, for example, SEQ ID NO:16.

The invention also includes a method of producing a CSF1R ECD fusion molecule. For example, in some embodiments, the method comprises: (a) culturing a CHO cell comprising the polynucleotide of any one of the above described CSF1R ECD fusion molecules in conditions such that the CSF1R ECD fusion molecule is expressed; and (b) recovering the CSF1R ECD fusion molecule. The invention further includes this method with the step of fusing polyethylene glycol to the CSF1R ECD fusion molecule.

BRIEF DESCRIPTION OF THE DRAWINGS

FIG. 9a shows lung metastases in mice treated with mCSF1R.511-Fc-encoding or mCSF1R.506-Fc-encoding minicircle DNA, and FIG. 9b shows lung metastases in mice treated with the mCSF1R.506-Fc fusion protein.

FIG. 10 shows the ability of the mCSF1R.506-Fc fusion protein (shown as m506) and the hCSF1R.506-Fc fusion protein (shown as h506) to inhibit cancer metastasis-induced osteolytic bone loss in an in vivo mouse model.

DETAILED DESCRIPTION OF CERTAIN EMBODIMENTS

Figure 1:
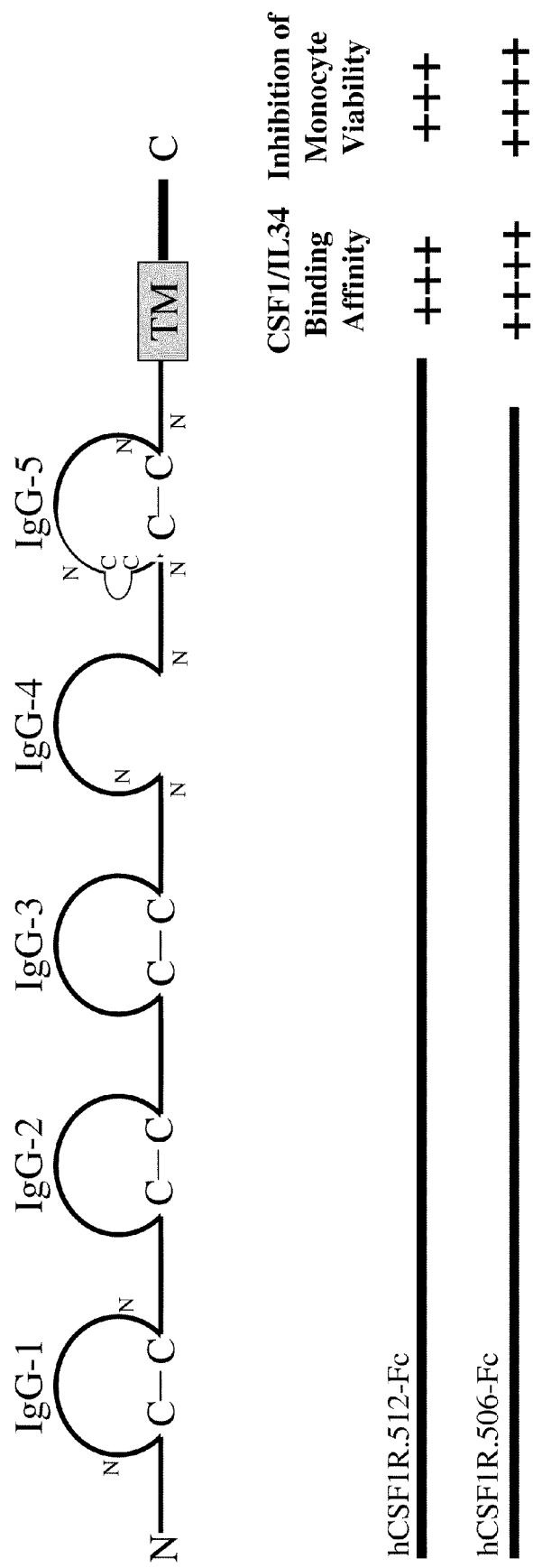
FIG. 1 shows the domain structure of the full-length human CSF1R ECD, which consists of 512 amino acid residues. The five IgG domains are denoted from N terminus to C terminus as IgG-1, IgG-2, IgG-3, IgG-4, and IgG-5. Also shown is the relative ability of the human CSF1R ECD fusion molecules, hCSF1R.512-Fc and hCSF1R.506-Fc, to bind to the CSF1 and IL34 ligands and to inhibit monocyte viability.

The section headings used herein are for organizational purposes only and are not to be construed as limiting the subject matter described.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

Certain techniques used in connection with recombinant DNA, oligonucleotide synthesis, tissue culture and transformation (e.g., electroporation, lipofection), enzymatic reactions, and purification techniques are known in the art. Many such techniques and procedures are described, e.g., in Sambrook et al. *Molecular Cloning: A Laboratory Manual* (2nd ed., Cold Spring Harbor Laboratory Press, Cold Spring Harbor, N.Y. (1989)), among other places. In addition, certain techniques for chemical syntheses, chemical analyses, pharmaceutical preparation, formulation, and delivery, and treatment of patients are also known in the art.

In this application, the use of "or" means "and/or" unless stated otherwise. In the context of a multiple dependent claim, the use of "or" refers back to more than one preceding independent or dependent claim in the alternative only. Also, terms such as "element" or "component" encompass both elements and components comprising one unit and elements and components that comprise more than one subunit unless specifically stated otherwise.

As utilized in accordance with the present disclosure, the following terms, unless otherwise indicated, shall be understood to have the following meanings:

The terms "nucleic acid molecule" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

The term "CSF1R" refers herein to the full-length CSF1R, which includes the N-terminal ECD, the transmembrane domain, and the intracellular tyrosine kinase domain, with or without an N-terminal signal peptide. In one embodiment, the CSF1R is a human CSF1R having an amino acid sequence corresponding to SEQ ID NO.:22 or to SEQ ID NO.:23. In another embodiment, the CSF1R is a mouse CSF1R having an amino acid sequence corresponding to SEQ ID NO.:24 or to SEQ ID NO.:25.

The term "CSF1R extracellular domain" ("CSF1R ECD") includes full-length CSF1R ECDs, CSF1R ECD fragments, and CSF1R ECD variants. As used herein, the term "CSF1R ECD" refers to a CSF1R polypeptide that lacks the intracellular and transmembrane domains. In one embodiment, the CSF1R ECD is a human full-length CSF1R ECD having an amino acid sequence corresponding to SEQ ID NO.:1. The term "full-length CSF1R ECD", as used herein, refers to a CSF1R ECD that extends to the last amino acid of the extracellular domain, and may or may not include an N-terminal signal peptide. For example, the last amino acid of the full-length CSF1R ECD is at position 512 for the human ECD and at position 511 for the mouse ECD. Thus, a human full-length CSF1R ECD may consist of the amino acid sequence corresponding to SEQ ID NO.:1 (mature form) or to SEQ ID NO.:11 (with the signal peptide), and a mouse full-length CSF1R ECD may consist of the amino acid sequence corresponding to SEQ ID NO.:3 (mature form) or to SEQ ID NO.:13 (with the signal peptide). As used herein, the term "CSF1R ECD fragment" refers to a CSF1R ECD having one or more residues deleted from the N or C terminus of the full-length ECD and that retains the ability to bind to the CSF1 or IL34 ligand. The CSF1R ECD fragment may or may not include an N-terminal signal peptide. In one embodiment, the CSF1R ECD fragment is a human CSF1R ECD fragment having an amino acid sequence corresponding to SEQ ID NO.:2 (mature form) or to SEQ ID NO.:12 (with the signal peptide). In another embodiment, the CSF1R ECD fragment is a mouse CSF1R ECD fragment having an amino acid sequence corresponding to SEQ ID NO.:4 (mature form) or to SEQ ID NO.:14 (with the signal peptide). As used herein, the term "CSF1R ECD variants" refers to CSF1R ECDs that contain amino acid additions, deletions, and substitutions and that remain capable of binding to CSF1 or IL34. Such variants may be at least 70%, 80%, 90%, 95%, 97%, 98%, or 99% identical to the parent ECD. The % identity of two polypeptides may be measured by a similarity score determined by comparing the amino acid sequences of the two polypeptides using the Bestfit program with the default settings for determining similarity. Bestfit uses the local homology algorithm of Smith and Waterman, *Advances in Applied Mathematics* 2:482-489 (1981) to find the best segment of similarity between two sequences.

A polypeptide having an amino acid sequence at least, for example, 95% identical to a reference amino acid sequence of a CSF1R ECD is one in which the amino acid sequence of the polypeptide is identical to the reference sequence except that the polypeptide sequence may include up to five amino acid alterations per each 100 amino acids of the reference polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids, up to 5% of the total amino acid residues in the reference sequence, may be inserted into the reference sequence. These alterations of the reference sequence may occur at the N- or C-terminal positions of the reference amino acid sequence or anywhere between those terminal positions, interspersed either individually among residues in the reference sequence, or in one or more contiguous groups within the reference sequence.

As a practical matter, whether any particular polypeptide is at least 70%, 80%, 90%, or 95% identical to, for instance, an amino acid sequence or to a polypeptide sequence encoded by a nucleic acid sequence set forth in the Sequence Listing may be determined conventionally using known computer programs, such the Bestfit program. When using Bestfit or other sequence alignment program to determine whether a particular sequence is, for instance, 95% identical to a reference sequence according to the present invention, the parameters are set, of course, that the percentage of identity is calculated over the full length of the reference amino acid sequence and that gaps in homology of up to 5% of the total number of amino acid residues in the reference sequence are allowed.

As used herein, the terms "hCSF1R-ECD.512" and "hCSF1R.512" may be used interchangeably to refer to the full-length human CSF1R ECD corresponding to SEQ ID NO.:1.

As used herein, the terms "hCSF1R-ECD.506" and "hCSF1R.506" may be used interchangeably to refer to the human CSF1R ECD corresponding to SEQ ID NO.:2.

As used herein, the terms "mCSF1R-ECD.511" and "mCSF1R.511" may be used interchangeably to refer to the full-length mouse CSF1R ECD corresponding to SEQ ID NO.:3.

As used herein, the terms "mCSF1R-ECD.506" and "mCSF1R.506" may be used interchangeably to refer to the mouse CSF1R ECD corresponding to SEQ ID NO.:4.

As used herein, the terms "hCSF1R-ECD.511" and "hCSF1R.511" may be used interchangeably to refer to the human CSF1R ECD corresponding to SEQ ID NO.:26.

As used herein, the term "CSF1R IgG domain" refers to one of five IgG domains that comprise the CSF1R ECD. As used herein, the five IgG domains of the CSF1R ECD include from the N terminus to C terminus, "IgG-1," "IgG-2," "IgG-3," "IgG-4," and "IgG-5."

The term "CSF1R ECD fusion molecule" refers to a molecule comprising a CSF1R ECD, and one or more "fusion partners." In certain embodiments, the CSF1R ECD and the fusion partner are covalently linked ("fused"). If the fusion partner is also a polypeptide ("the fusion partner polypeptide"), the CSF1R ECD and the fusion partner polypeptide may be part of a continuous amino acid sequence, and the fusion partner polypeptide may be linked to either the N terminus or the C terminus of the CSF1R ECD. In such cases, the CSF1R ECD and the fusion partner polypeptide may be translated as a single polypeptide from a coding sequence that encodes both the CSF1R ECD and the fusion partner polypeptide (the "CSF1R ECD fusion protein"). In certain embodiments, the CSF1R ECD and the fusion partner are covalently linked through other means, such as, for example, a chemical linkage other than a peptide bond. Many known methods of covalently linking polypeptides to other molecules (for example, fusion partners) may be used. In other embodiments, the CSF1R ECD and the fusion partner may be fused through a "linker," which is comprised of at least one amino acid or chemical moiety.

In certain embodiments, the CSF1R polypeptide and the fusion partner are noncovalently linked. In certain such embodiments, they may be linked, for example, using binding pairs. Exemplary binding pairs include, but are not limited to, biotin and avidin or streptavidin, an antibody and its antigen, etc.

Certain exemplary fusion partners include, but are not limited to, an immunoglobulin Fc domain, albumin, and polyethylene glycol. The amino acid sequences of certain exemplary Fc domains are shown in SEQ ID NOs.:19 to 21. In certain embodiments, there is a two amino acid residue linker consisting of an N-terminal glycine residue followed by a serine residue (GS) located between the CSF1R ECD and the Fc. The amino acid sequence of a certain exemplary N-terminal GS linker followed by an Fc is shown in SEQ ID NO.:30.

The term "signal peptide" refers to a sequence of amino acid residues located at the N terminus of a polypeptide that facilitates secretion of a polypeptide from a mammalian cell. A signal peptide may be cleaved upon export of the polypeptide from the mammalian cell, forming a mature protein. Signal peptides may be natural or synthetic, and they may be heterologous or homologous to the protein to which they are attached. Certain exemplary signal peptides include, but are not limited to, the signal peptides of CSF1R, such as, for example, the amino acid sequence of SEQ ID NOs.:9 and 10, which correspond to the human and mouse CSF1R signal peptides, respectively. Certain exemplary signal peptides may also include signal peptides from heterologous proteins. A "signal sequence" refers to a polynucleotide sequence that encodes a signal peptide. In certain embodiments, a CSF1R ECD lacks a signal peptide. In certain embodiments, a CSF1R ECD includes at least one signal peptide, which may be selected from a native CSF1R signal peptide or a heterologous signal peptide.

In certain embodiments, the CSF1R ECD amino acid sequence is derived from that of a non-human mammal. In such embodiments, the CSF1R ECD amino acid sequence may be derived from mammals including, but not limited to, rodents, simians, felines, canines, equines, bovines, porcines, ovines, caprines, mammalian laboratory animals, mammalian farm animals, mammalian sport animals, and mammalian pets. CSF1R ECD fusion molecules incorporating a non-human CSF1R ECD are termed "non-human CSF1R ECD fusion molecules." Similar to the human CSF1R ECD fusion molecules, non-human fusion molecules may comprise a fusion partner, optional linker, and a CSF1R ECD. Such non-human fusion molecules may also include a signal peptide. Examples of non-human CSF1R ECDs are SEQ ID NOs:3 and 13, which correspond to the mouse CSF1R ECD.511 sequence with and without a signal peptide, and SEQ ID NOs:4 and 14, which correspond to the mouse CSF1R ECD.506 sequence without and with a signal peptide. Examples of non-human fusion molecules are SEQ ID NOs: 7, 8, 33, and 34. A "non-human CSF1R ECD fragment" refers to a non-human CSF1R ECD having one or more residues deleted from the N or C terminus of the full-length ECD and that retains the ability to bind to the CSF1 or IL34 ligands of the non-human animal from which the sequence was derived. See, e.g., SEQ ID NOs:4 and 14. A "non-human CSF1R ECD variant" refers to CSF1R ECDs that contain amino acid additions, deletions, and substitutions and that remain capable of binding to CSF1 or IL34 from the animal from which the sequence was derived. In some embodiments, the last five or the last six C-terminal amino acid residues of the non-human full length CSF1R ECD are deleted, for example. See, e.g., SEQ ID NOs:4 and 14.

The term "vector" is used to describe a polynucleotide that may be engineered to contain a cloned polynucleotide or polynucleotides that may be propagated in a host cell. A vector may include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that may be used in colorimetric assays, e.g., β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells; plant cells; and insect cells. Certain exemplary mammalian cells include, but are not limited to, 293 and CHO cells, and their derivatives, such as 293-6E and DG44 cells, respectively.

The term "isolated" as used herein refers to a molecule that has been separated from at least some of the components with which it is typically found in nature. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated" so long as that polynucleotide is not found in that vector in nature.

The terms "subject" and "patient" are used interchangeably herein to refer to mammals, including, but not limited to, rodents, simians, humans, felines, canines, equines, bovines, porcines, ovines, caprines, mammalian laboratory animals, mammalian farm animals, mammalian sport animals, and mammalian pets.

The term "cancer" refers to a proliferative disorder associated with uncontrolled cell proliferation, unrestrained cell growth, and decreased cell death/apoptosis. Cancer includes, but is not limited to, breast cancer, prostate cancer, lung cancer, kidney cancer, thyroid cancer, melanoma, follicular lymphomas, carcinomas with p53 mutations, and hormone-dependent tumors, including, but not limited to, colon cancer, cardiac tumors, pancreatic cancer, retinoblastoma, glioblastoma, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, Kaposi's sarcoma, ovarian cancer, leukemia (including acute leukemias (for example, acute lymphocytic leukemia, acute myelocytic leukemia, including myeloblastic, promyelocytic, myelomonocytic, monocytic, and erythroleukemia)) and chronic leukemias (for example, chronic myelocytic (granulocytic) leukemia and chronic lymphocytic leukemia), myelodysplastic syndrome polycythemia vera, lymphomas (for example, Hodgkin's disease and non-Hodgkin's disease), multiple myeloma, Waldenström's macroglobulinemia, heavy chain diseases, and solid tumors including, but not limited to, sarcomas and carcinomas such as fibrosarcoma, myxosarcoma, liposarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, and menangioma. The terms "metastasis" and "cancer metastasis" are used interchangeably herein to refer to the ability of a cancer cell to spread to other tissues. For example, "metastasis to bone" refers to the ability of certain types of cancer including, but not limited to, breast, prostate, lung, kidney, thyroid, and melanoma, to metastasize to bone.

The term "osteolytic disorders" is used herein to refer to any condition that is caused by an increase in the activity of osteoclasts, which are cells responsible for bone resorption. The terms "osteolysis" and "osteolytic bone loss" may be used interchangeably to refer to osteoclast-mediated bone resorption or bone loss associated with an osteolytic disorder. Osteolytic disorders may occur in subjects with a predisposition to develop an osteolytic disorder, or they may occur in subjects with a disease that leads to or contributes to an osteolytic disorder by stimulating osteoclast activity. In exemplary embodiments of the present invention, the osteolytic disorder may include osteolytic bone loss and cancer metastasis-induced osteolytic bone loss. In further exemplary embodiments of the present invention, the osteolytic bone disorder includes metabolic bone disease, including endocrinopathies, such as hypercortisolism, hypogonadism, primary or secondary hyperparathyroidism, and hyperthyroidism; dietary deficiency, including rickets, osteomalacia, scurvy, and malnutrition; osteoporosis; drug use, including glucocorticoids (glucocorticoid-induced osteoperosis), heparin, and alcohol; chronic disease, including malabsorption syndromes; chronic renal failure, including renal osteodystrophy; chronic liver disease, including hepatic osteodystrophy; inherited disease, including osteogenesis imperfecta and homocystinuria; and bone inflammation associated with arthritis, rheumatoid arthritis, psoriatic arthritis, fibrous dysplasia, periodontal disease, and Paget's disease.

The terms "metastasis-induced osteolytic bone loss," and "cancer metastasis-induced osteolytic bone loss," are used interchangeably herein to refer to osteolysis or osteolytic bone loss resulting from cancer cell metastasis to bone. The term "cancer metastasis-induced osteoclast activation" is used herein to refer to the ability of cancer cells that have metastasized to bone to induce the activation of osteoclasts.

The term "hypercalcemia" is used herein to refer to elevated blood calcium levels that may be caused by increased bone resorption associated with increased osteoclast activity. The term "vitamin D3-induced hypercalcemia" is used herein to refer to the ability of vitamin D3 to induce hypercalcemia. The term "hypercalcemia-induced bone loss" is used herein to refer to osteolytic bone loss associated with hypercalcemia or vitamin D3-induced hypercalcemia.

The term "tumor" is used herein to refer to a group of cells that exhibit abnormally high levels of proliferation and growth. A tumor may be benign, pre-malignant, or malignant; malignant tumor cells are cancerous. Tumor cells may be solid tumor cells or leukemic tumor cells. The term "tumor growth" is used herein to refer to proliferation or growth by a cell or cells that comprise a tumor that leads to a corresponding increase in the size of the tumor. The term "CSF1R-dependent tumor growth" is used herein to refer to the requirement of a tumor cell or cells for CSF1R-mediated function(s) in order for the tumor cell or cells to proliferate or grow.

"Treatment," as used herein, covers any administration or application of a therapeutic for disease in a mammal, including a human, and includes inhibiting the disease or progression of the disease, partially inhibiting or slowing the disease or its progression, arresting its development, partially or fully relieving the disease, or curing the disease, for example, by causing regression, or restoring or repairing a lost, missing, or defective function; or stimulating an inefficient process.

The terms "inhibition" or "inhibit" refer to a decrease or cessation of any phenotypic characteristic or to the decrease or cessation in the incidence, degree, or likelihood of that characteristic.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule.

If the therapeutic agent is to be administered subcutaneously, the carrier ideally is not irritable to the skin and does not cause injection site reaction.

Methods of Treating Diseases Using CSF1R ECD Fusion Molecules

The CSF1R ECD fusion molecules of the invention are able to inhibit osteolytic bone loss in vivo. Furthermore, the CSF1R ECD fusion molecules of the invention were also able to inhibit cancer metastasis, cancer metastasis-induced osteolytic bone loss, and tumor growth. The CSF1R ECD fusion molecules of the invention have been found to retain the ability to bind CSF1 and IL34. See, e.g., Example 5, including Tables 2 and 3. Thus, the CSF1R ECD fusion molecules of the invention may be used as ligand traps in vivo to treat diseases associated with one or more ligands of CSF1R, such as CSF1 and/or IL34. The CSF1R ECD fusion molecules of the invention may be used, for example, to treat osteolytic bone loss, cancer metastasis, cancer metastasis-induced osteolytic bone loss, and tumor growth. In certain embodiments, the CSF1R ECD fusion proteins comprise a fusion partner such as an Fc, albumin, and/or polyethylene glycol (discussed above).

In one embodiment, CSF1R ECD fusion molecules may be used to treat osteolytic disorders. In another embodiment, the CSF1R ECD fusion proteins of the invention may be administered, e.g., as described above, to treat patients who have an osteolytic disorder, including, but not limited to, osteolytic bone loss and cancer metastasis-induced osteolytic bone loss; metabolic bone disease, including endocrinopathies, such as hypercortisolism, hypogonadism, primary or secondary hyperparathyroidism, and hyperthyroidism; dietary deficiency, including rickets, osteomalacia, scurvy, and malnutrition; osteoporosis; drug use, including glucocorticoids (glucocorticoid-induced osteoperosis), heparin, and alcohol; chronic disease, including malabsorption syndromes; chronic renal failure, including renal osteodystrophy; chronic liver disease, including hepatic osteodystrophy; inherited disease, including osteogenesis imperfecta and homocystinuria; and bone inflammation associated with arthritis, rheumatoid arthritis, psoriatic arthritis, fibrous dysplasia, periodontal disease, and Paget's disease. In certain embodiments, the CSF1R ECD fusion molecules may be administered along with at least one other therapeutic regimen and/or agent. to patients suffering from an osteolytic disorder.

In certain embodiments, CSF1R ECD fusion molecules may be used to treat cancer, cancer metastasis, or cancer metastasis to bone. In another embodiment, the CSF1R ECD fusion molecule of the invention may be administered, e.g., as described above, to patients to treat CSF1- and/or IL34-dependent cancer. In certain embodiments, the CSF1R ECD fusion molecule may be administered along with at least one other therapeutic regimen and/or agent to patients suffering from cancer.

The invention includes a method of depleting peripheral blood monocytes in a patient comprising administering to the patient a therapeutically effective amount of a CSF1R ECD fusion molecule, wherein the CSF1R ECD fusion molecule comprises a CSF1R ECD and one or more fusion partners. The invention further includes a method of depleting peripheral blood monocytes in a patient comprising administering to the patient a therapeutically effective amount of a CSF1R ECD fusion molecule, wherein the amino acid sequence of the CSF1R ECD consists of SEQ ID NO.:2, SEQ ID NO.:26, or SEQ ID NO.:1. In certain embodiments, the one or more fusion partners are selected from an Fc, albumin, and polyethylene glycol. In certain other embodiments, the one or more fusion partners of the are selected from an Fc alone, polyethylene glycol alone, and an Fc and polyethylene glycol. The invention further includes the method of depleting peripheral blood monocytes in a patient comprising administering to the patient a therapeutically effective amount of a CSF1R ECD fusion molecule, wherein the one or more fusion partners is an Fc, and wherein the amino acid sequence of the CSF1R ECD fusion molecule consists of SEQ ID NO.:6 or SEQ ID NO.:5. The invention also includes the method of depleting peripheral blood monocytes in a patient comprising administering to the patient a therapeutically effective amount of a CSF1R ECD fusion molecule, wherein the one or more fusion partners is an Fc, and wherein the amino acid sequence of the CSF1R ECD fusion molecule consists of SEQ ID NO.:6 or SEQ ID NO.:5, and wherein the CSF1R ECD fusion molecule is glycosylated or sialylated. The invention further includes the method of depleting peripheral blood monocytes in a patient comprising administering to the patient a therapeutically effective amount of a CSF1R ECD fusion molecule, wherein the CSF1R ECD fusion molecule comprises a CSF1R ECD and one or more fusion partners, and wherein the CSF1R ECD fusion molecule is produced from a CHO cell.

CSF1R Extracellular Domains

Certain exemplary CSF1R ECDs include full-length CSF1R ECDs, CSF1R ECD fragments, and CSF1R ECD variants. CSF1R ECDs may include or lack a signal peptide. Exemplary CSF1R ECDs include, but are not limited to, CSF1R ECDs having amino acid sequences selected from SEQ ID NOs.:1, 2, 11, 12, 26 and 27 for human CSF1R, and SEQ ID NOs.:3, 4, 13, and 14 for mouse CSF1R. In certain embodiments, a CSF1R ECD is isolated.

The inventors have discovered that a human CSF1R ECD fusion molecule wherein the CSF1R ECD has the amino acid sequence corresponding to SEQ ID NO.:2 exhibits properties that will be particularly useful with respect to the treatment of disease, including osteolytic bone loss, cancer metastasis, cancer metastasis-induced osteolytic bone loss, and tumor growth. The inventors have found that this fusion molecule binds more tightly to the CSF1R ligands, CSF1 and IL34, compared to the full-length human CSF1R ECD fusion molecule wherein the CSF1R ECD has the amino acid sequence corresponding to SEQ ID NO.:1. Furthermore, the CSF1R ECD fusion molecule wherein the CSF1R ECD has the amino acid sequence corresponding to SEQ ID NO.:2 more effectively inhibits monocyte growth compared to the full-length human CSF1R ECD fusion molecule wherein the CSF1R ECD has the amino acid sequence corresponding to SEQ ID NO.:1.

CSF1R ECD Fragments

Non-limiting exemplary CSF1R ECD fragments include the human CSF1R ECD in which the last six C-terminal amino acid residues of the full-length CSF1R ECD are removed, but in which all five IgG domains are maintained (hCSF1R.506), the human CSF1R ECD in which the last C-terminal amino acid residue of the full-length CSF1R ECD is removed, but in which all five IgG domains are maintained (hCSF1R.511), and the mouse CSF1R ECD in which the last five C-terminal amino acid residues of the full-length CSF1R ECD are removed, but in which all five IgG domains are maintained (mCSF1R.506).

CSF1R ECD fragments may include or lack a signal peptide. Exemplary CSF1R ECD fragments include, but are not limited to, CSF1R ECD fragments having amino acid sequences selected from SEQ ID NOs.:2, 12, 26, and 27 for human CSF1R, and SEQ ID NOs.:4 and 14 for mouse CSF1R.

Fusion Partners and Conjugates

As discussed, the CSF1R ECD of the present invention may be combined with a fusion partner polypeptide, resulting in a CSF1R ECD fusion protein. These fusion partner polypeptides may facilitate purification, and the CSF1R ECD fusion proteins may show an increased half-life in vivo. Fusion partner polypeptides that have a disulfide-linked dimeric structure due to the IgG portion may also be more efficient in binding and neutralizing other molecules than the monomeric CSF1R ECD fusion protein or the CSF1R ECD alone. Suitable fusion partners of a CSF1R ECD include, for example, polymers, such as water soluble polymers, the constant domain of immunoglobulins; all or part of human serum albumin (HSA); fetuin A; fetuin B; a leucine zipper domain; a tetranectin trimerization domain; mannose binding protein (also known as mannose binding lectin), for example, mannose binding protein 1; and an Fc region, as described herein and further described in U.S. Pat. No. 6,686,179.

A CSF1R ECD fusion molecule of the invention may be prepared by attaching polyaminoacids or branch point amino acids to the CSF1R ECD. For example, the polyaminoacid may be a carrier protein that serves to increase the circulation half life of the CSF1R ECD (in addition to the advantages achieved via a fusion molecule). For the therapeutic purpose of the present invention, such polyaminoacids should ideally be those that have or do not create neutralizing antigenic response, or other adverse responses. Such polyaminoacids may be chosen from serum album (such as HSA), an additional antibody or portion thereof, for example the Fc region, fetuin A, fetuin B, leucine zipper nuclear factor erythroid derivative-2 (NFE2), neuroretinal leucine zipper, tetranectin, or other polyaminoacids, for example, lysines. As described herein, the location of attachment of the polyaminoacid may be at the N terminus or C terminus, or other places in between, and also may be connected by a chemical linker moiety to the selected molecule.

Polymers

Polymers, for example, water soluble polymers, are useful in the present invention as the CSF1R ECD to which the polymer is attached will not precipitate in an aqueous environment, such as typically found in a physiological environment. Polymers employed in the invention will be pharmaceutically acceptable for the preparation of a therapeutic product or composition.

Suitable, clinically acceptable, water soluble polymers include, but are not limited to, polyethylene glycol (PEG), polyethylene glycol propionaldehyde, copolymers of ethylene glycol/propylene glycol, monomethoxy-polyethylene glycol, carboxymethylcellulose, dextran, polyvinyl alcohol (PVA), polyvinyl pyrrolidone, poly-1,3-dioxolane, poly-1,3,6-trioxane, ethylene/maleic anhydride copolymer, poly (β-amino acids) (either homopolymers or random copolymers), poly(n-vinyl pyrrolidone) polyethylene glycol, polypropylene glycol homopolymers (PPG) and other polyakylene oxides, polypropylene oxide/ethylene oxide copolymers, polyoxyethylated polyols (POG) (e.g., glycerol) and other polyoxyethylated polyols, polyoxyethylated sorbitol, or polyoxyethylated glucose, colonic acids or other carbohydrate polymers, Ficoll, or dextran and mixtures thereof.

As used herein, polyethylene glycol (PEG) is meant to encompass any of the forms that have been used to derivatize other proteins, such as mono-(C1-C10) alkoxy- or aryloxy-polyethylene glycol. Polyethylene glycol propionaldehyde may have advantages in manufacturing due to its stability in water.

Polymers used herein, for example water soluble polymers, may be of any molecular weight and may be branched or unbranched. In certain embodiments, the polymers each typically have an average molecular weight of between about 2 kDa to about 100 kDa (the term "about" indicating that in preparations of a polymer, some molecules will weigh more, some less, than the stated molecular weight). The average molecular weight of each polymer may be between about 5 kDa and about 50 kDa, or between about 12 kDa and about 25 kDa. Generally, the higher the molecular weight or the more branches, the higher the polymer:protein ratio. Other sizes may also be used, depending on the desired therapeutic profile; for example, the duration of sustained release; the effects, if any, on biological activity; the ease in handling; the degree or lack of antigenicity; and other known effects of a polymer on a CSF1R ECD of the invention.

Polymers employed in the present invention are typically attached to a CSF1R ECD with consideration of effects on functional or antigenic domains of the polypeptide. In general, chemical derivatization may be performed under any suitable condition used to react a protein with an activated polymer molecule. Activating groups which can be used to link the polymer to the active moieties include sulfone, maleimide, sulfhydryl, thiol, triflate, tresylate, azidirine, oxirane, and 5-pyridyl.

Polymers of the invention are typically attached to a heterologous polypeptide at the alpha (α) or epsilon (ϵ) amino groups of amino acids or a reactive thiol group, but it is also contemplated that a polymer group could be attached to any reactive group of the protein that is sufficiently reactive to become attached to a polymer group under suitable reaction conditions. Thus, a polymer may be covalently bound to a CSF1R ECD via a reactive group, such as a free amino or carboxyl group. The amino acid residues having a free amino group may include lysine residues and the N-terminal amino acid residue. Those having a free carboxyl group may include aspartic acid residues, glutamic acid residues, and the C-terminal amino acid residue. Those having a reactive thiol group include cysteine residues.

Methods for preparing fusion molecules conjugated with polymers, such as water soluble polymers, will each generally involve (a) reacting a CSF1R ECD with a polymer under conditions whereby the polypeptide becomes attached to one or more polymers and (b) obtaining the reaction product. Reaction conditions for each conjugation may be selected from any of those known in the art or those subsequently developed, but should be selected to avoid or limit exposure to reaction conditions such as temperatures, solvents, and pH levels that would inactivate the protein to be modified. In general, the optimal reaction conditions for the reactions will be determined case-by-case based on known parameters and the desired result. For example, the larger the ratio of polymer:polypeptide conjugate, the greater the percentage of conjugated product. The optimum ratio (in terms of efficiency of reaction in that there is no excess unreacted polypeptide or polymer) may be determined by factors such as the desired degree of derivatization (e.g., mono-, di-, tri-, etc.), the molecular weight of the polymer selected, whether the polymer is branched or unbranched, and the reaction conditions used. The ratio of polymer (for example, PEG) to a polypeptide will generally range from 1:1 to 100:1. One or more purified conjugates may be prepared from each mixture by standard purification techniques, including among others, dialysis, salting-out, ultrafiltration, ion-exchange chromatography, gel filtration chromatography, and electrophoresis.

One may specifically desire an N-terminal chemically modified CSF1R ECD. One may select a polymer by molecular weight, branching, etc., the proportion of polymers to CSF1R ECD molecules in the reaction mix, the type of reaction to be performed, and the method of obtaining the selected N-terminal chemically modified CSF1R ECD. The method of obtaining the N-terminal chemically modified CSF1R ECD preparation (separating this moiety from other monoderivatized moieties if necessary) may be by purification of the N-terminal chemically modified CSF1R ECD material from a population of chemically modified protein molecules.

Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N terminus with a carbonyl group-containing polymer is achieved. For example, one may selectively attach a polymer to the N terminus of the protein by performing the reaction at a pH that allows one to take advantage of the pKa differences between the s-amino group of the lysine residues and that of the α-amino group of the N-terminal residue of the protein. By such selective derivatization, attachment of a polymer to a protein is controlled: the conjugation with the polymer takes place predominantly at the N terminus of the protein and no significant modification of other reactive groups, such as the lysine side chain amino groups, occurs. Using reductive alkylation, the polymer may be of the type described above and should have a single reactive aldehyde for coupling to the protein. Polyethylene glycol propionaldehyde, containing a single reactive aldehyde, may also be used.

In one embodiment, the present invention contemplates the chemically derivatized CSF1R ECD to include mono- or poly- (e.g., 2-4) PEG moieties. Pegylation may be carried out by any of the pegylation reactions available. Methods for preparing a pegylated protein product will generally include (a) reacting a polypeptide with polyethylene glycol (such as a reactive ester or aldehyde derivative of PEG) under conditions whereby the protein becomes attached to one or more PEG groups; and (b) obtaining the reaction product(s). In general, the optimal reaction conditions will be determined case by case based on known parameters and the desired result.

There are a number of PEG attachment methods available to those skilled in the art. See, for example, EP 0 401 384; Malik et al., *Exp. Hematol.*, 20:1028-1035 (1992); Francis, *Focus on Growth Factors*, 3(2):4-10 (1992); EP 0 154 316; EP 0 401 384; WO 92/16221; WO 95/34326; and the other publications cited herein that relate to pegylation.

The step of pegylation as described herein may be carried out via an acylation reaction or an alkylation reaction with a reactive polyethylene glycol molecule. Thus, protein products according to the present invention include pegylated proteins wherein the PEG group(s) is (are) attached via acyl or alkyl groups. Such products may be mono-pegylated or poly-pegylated (for example, those containing 2-6 or 2-5 PEG groups). The PEG groups are generally attached to the protein at the α- or ϵ-amino groups of amino acids, but it is also contemplated that the PEG groups could be attached to any amino group attached to the protein that is sufficiently reactive to become attached to a PEG group under suitable reaction conditions.

Pegylation by acylation generally involves reacting an active ester derivative of polyethylene glycol (PEG) with a CSF1R ECD of the invention. For acylation reactions, the polymer(s) selected typically have a single reactive ester group. Any known or subsequently discovered reactive PEG molecule may be used to carry out the pegylation reaction. An example of a suitable activated PEG ester is PEG esterified to N-hydroxysuccinimide (NHS). As used herein, acylation is contemplated to include, without limitation, the following types of linkages between the therapeutic protein and a polymer such as PEG: amide, carbamate, urethane, and the like, see for example, Chamow, *Bioconjugate Chem.*, 5:133-140 (1994). Reaction conditions may be selected from any of those currently known or those subsequently developed, but should avoid conditions such as temperature, solvent, and pH that would inactivate the polypeptide to be modified.

Pegylation by acylation will generally result in a poly-pegylated protein. The connecting linkage may be an amide. The resulting product may be substantially only (e.g., >95%) mono-, di-, or tri-pegylated. However, some species with higher degrees of pegylation may be formed in amounts depending on the specific reaction conditions used. If desired, more purified pegylated species may be separated from the mixture (particularly unreacted species) by standard purification techniques, including among others, dialysis, salting-out, ultrafiltration, ion-exchange chromatography, gel filtration chromatography, and electrophoresis.

Pegylation by alkylation generally involves reacting a terminal aldehyde derivative of PEG with a polypeptide in the presence of a reducing agent. For the reductive alkylation reaction, the polymer(s) selected should have a single reactive aldehyde group. An exemplary reactive PEG aldehyde is polyethylene glycol propionaldehyde, which is water stable, or mono C1-C10 alkoxy or aryloxy derivatives thereof, see for example, U.S. Pat. No. 5,252,714.

Markers

Moreover, CSF1R ECDs of the present invention may be fused to marker sequences, such as a peptide that facilitates purification of the fused polypeptide. The marker amino acid sequence may be a hexa-histidine peptide such as the tag provided in a pQE vector (Qiagen, Mississauga, Ontario, Canada), among others, many of which are commercially available. As described in Gentz et al., *Proc. Natl. Acad. Sci.* 86:821-824 (1989), for instance, hexa-histidine provides for convenient purification of the fusion protein. Another peptide tag useful for purification, the hemagglutinin (HA) tag, corresponds to an epitope derived from the influenza HA protein. (Wilson et al., *Cell* 37:767 (1984)). Any of these above fusions may be engineered using the CSF1R ECDs of the present invention.

Oligomerization Domain Fusion Partners

In various embodiments, oligomerization offers certain functional advantages to a fusion protein, including, but not limited to, multivalency, increased binding strength, and the combined function of different domains. Accordingly, in certain embodiments, a fusion partner comprises an oligomerization domain, for example, a dimerization domain. Exemplary oligomerization domains include, but are not limited to, coiled-coil domains, including alpha-helical coiled-coil domains; collagen domains; collagen-like domains; and certain immunoglobulin domains. Certain exemplary coiled-coil polypeptide fusion partners include the tetranectin coiled-coil domain; the coiled-coil domain of cartilage oligomeric matrix protein; angiopoietin coiled-coil domains; and leucine zipper domains. Certain exemplary collagen or collagen-like oligomerization domains include, but are not limited to, those found in collagens, mannose binding lectin, lung surfactant proteins A and D, adiponectin, ficolin, conglutinin, macrophage scavenger receptor, and emilin.

Antibody Fc Immunoglobulin Domain Fusion Partners

Many Fc domains that may be used as fusion partners are known in the art. In certain embodiments, a fusion partner is an Fc immunoglobulin domain. An Fc fusion partner may be a wild-type Fc found in a naturally occurring antibody, a variant thereof, or a fragment thereof. Non-limiting exemplary Fc fusion partners include Fcs comprising a hinge and the CH2 and CH3 constant domains of a human IgG, for example, human IgG1, IgG2, IgG3, or IgG4. Certain additional Fc fusion partners include, but are not limited to, human IgA and IgM. In certain embodiments, an Fc fusion partner comprises a C237S mutation. In certain embodiments, an Fc fusion partner comprises a hinge, CH2, and CH3 domains of human IgG2 with a P331S mutation, as described in U.S. Pat. No. 6,900,292. Certain exemplary Fc domain fusion partners are shown in SEQ ID NOs.:19 to 21.

Albumin Fusion Partners and Albumin-binding Molecule Fusion Partners

In certain embodiments, a fusion partner is an albumin. Certain exemplary albumins include, but are not limited to, human serum album (HSA) and fragments of HSA that are capable of increasing the serum half-life or bioavailability of the polypeptide to which they are fused. In certain embodiments, a fusion partner is an albumin-binding molecule, such as, for example, a peptide that binds albumin or a molecule that conjugates with a lipid or other molecule that binds albumin. In certain embodiments, a fusion molecule comprising HSA is prepared as described, e.g., in U.S. Pat. No. 6,686,179.

Exemplary Attachment of Fusion Partners

The fusion partner may be attached, either covalently or non-covalently, to the N terminus or the C terminus of the CSF1R ECD. The attachment may also occur at a location within the CSF1R ECD other than the N terminus or the C terminus, for example, through an amino acid side chain (such as, for example, the side chain of cysteine, lysine, serine, or threonine).

In either covalent or non-covalent attachment embodiments, a linker may be included between the fusion partner and the CSF1R ECD. Such linkers may be comprised of at least one amino acid or chemical moiety. Exemplary methods of covalently attaching a fusion partner to a CSF1R ECD include, but are not limited to, translation of the fusion partner and the CSF1R ECD as a single amino acid sequence and chemical attachment of the fusion partner to the CSF1R ECD. When the fusion partner and a CSF1R ECD are translated as single amino acid sequence, additional amino acids may be included between the fusion partner and the CSF1R ECD as a linker. In certain embodiments, the linker is glycine-serine ("GS"). In certain embodiments, the linker is selected based on the polynucleotide sequence that encodes it, to facilitate cloning the fusion partner and/or CSF1R ECD into a single expression construct (for example, a polynucleotide containing a particular restriction site may be placed between the polynucleotide encoding the fusion partner and the polynucleotide encoding the CSF1R ECD, wherein the polynucleotide containing the restriction site encodes a short amino acid linker sequence). When the fusion partner and the CSF1R ECD are covalently coupled by chemical means, linkers of various sizes may typically be included during the coupling reaction.

Exemplary methods of non-covalently attaching a fusion partner to a CSF1R ECD include, but are not limited to, attachment through a binding pair. Exemplary binding pairs include, but are not limited to, biotin and avidin or streptavidin, an antibody and its antigen, etc.

In embodiments wherein the FGFR1 ECD sequence comprises SEQ ID NO:2 (which terminates at residue 506 of the human full length FGFR1 ECD), the FGFR1 ECD fusion molecule amino acid sequence excludes the last six C-terminal residues of SEQ ID NO:1 (which correspond to residues 507-512 of the human FGFR1 ECD). This phrase means that any additional amino acid residues that immediately follow the C-terminal amino acid residue of SEQ ID NO:2, such as from a polypeptide fusion partner or peptide linker, do not begin with the amino acid sequence of 507-512 of the human FGFR1 ECD, which is THPPDE. Although, of course, the amino acid sequence THPPDE may appear elsewhere in the amino acid sequence of the inventive proteins.

Signal Peptide

In order for some secreted proteins to express and secrete in large quantities, a signal peptide from a heterologous protein may be desirable. Employing heterologous signal peptides may be advantageous in that a resulting mature polypeptide may remain unaltered as the signal peptide is removed in the ER during the secretion process. The addition of a heterologous signal peptide may be required to express and secrete some proteins.

Certain exemplary signal peptide sequences are described, e.g., in the online Signal Peptide Database maintained by the Department of Biochemistry, National University of Singapore. See Choo et al., *BMC Bioinformatics*, 6: 249 (2005); and PCT Publication No. WO 2006/081430.

Co-Translational and Post-Translational Modifications

The invention encompasses CSF1R ECDs and CSF1R ECD fusion molecules that are differentially modified during or after translation, for example by glycosylation, acetylation, phosphorylation, amidation, derivatization by known protecting/blocking groups, proteolytic cleavage, or linkage to an antibody molecule or other cellular ligand. Any of numerous chemical modifications may be carried out by known techniques, including, but not limited to, specific chemical cleavage by cyanogen bromide, trypsin, chymotrypsin, papain, V8 protease; $NABH_4$; acetylation; formylation; oxidation; reduction; and/or metabolic synthesis in the presence of tunicamycin.

Additional post-translational modifications encompassed by the invention include, for example, for example, N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression Nucleic Acid Molecules Encoding CSF1R ECDs and Nucleic Acid Molecules Encoding CSF1R ECD Fusion Molecules Nucleic acid molecules comprising polynucleotides that encode CSF1R ECDs or CSF1R ECD fusion molecules are provided. Nucleic acid molecules comprising polynucleotides that encode CSF1R ECD fusion molecules in which the CSF1R ECD and the fusion partner are translated as a single polypeptide are also provided. Such nucleic acid molecules may be constructed using recombinant DNA techniques conventional in the art.

In certain embodiments, a polynucleotide encoding a CSF1R ECD comprises a nucleotide sequence that encodes a signal peptide, which, when translated, will be fused to the N terminus of the CSF1R ECD. As discussed above, the signal peptide may be the native CSF1R signal peptide, or may be another heterologous signal peptide. In certain embodiments, the nucleic acid molecule comprising the polynucleotide encoding the gene of interest is an expression vector that is suitable for expression in a selected host cell.

CSF1R ECD and CSF1R ECD Fusion Molecule Expression and Production

Vectors

Vectors comprising polynucleotides that encode CSF1R ECDs are provided. Vectors comprising polynucleotides that encode CSF1R ECD fusion molecules are also provided.

Such vectors include, but are not limited to, DNA vectors, phage vectors, viral vectors, retroviral vectors, etc.

In certain embodiments, a vector is selected that is optimized for expression of polypeptides in CHO or CHO-derived cells. Exemplary such vectors are described, e.g., in Running Deer et al., *Biotechnol. Prog.* 20:880-889 (2004).

In certain embodiments, a vector is chosen for in vivo expression of CSF1R ECDs and/or CSF1R ECD fusion molecules in animals, including humans. In certain such embodiments, expression of the polypeptide is under the control of a promoter that functions in a tissue-specific manner. For example, liver-specific promoters are described, e.g., in PCT Publication No. WO 2006/076288.

Host Cells

In various embodiments, CSF1R ECDs or CSF1R ECD fusion molecules may be expressed in prokaryotic cells, such as bacterial cells; or in eukaryotic cells, such as fungal cells, plant cells, insect cells, and mammalian cells. Such expression may be carried out, for example, according to procedures known in the art. Certain exemplary eukaryotic cells that may be used to express polypeptides include, but are not limited to, COS cells, including COS 7 cells; 293 cells, including 293-6E cells; CHO cells, including CHO-S and DG44 cells; and NSO cells. In certain embodiments, a particular eukaryotic host cell is selected based on its ability to make certain desired post-translational modifications to the CSF1R ECDs or CSF1R ECD fusion molecules. For example, in certain embodiments, CHO cells produce CSF1R ECD fusion molecules that have a higher level of sialylation than the same polypeptide produced in 293 cells.

Introduction of a nucleic acid into a desired host cell may be accomplished by any method known in the art, including but not limited to, calcium phosphate transfection, DEAE-dextran mediated transfection, cationic lipid-mediated transfection, electroporation, transduction, infection, etc. Certain exemplary methods are described, e.g., in Sambrook et al., *Molecular Cloning, A Laboratory Manual*, 3$^{rd}$ ed. Cold Spring Harbor Laboratory Press (2001). Nucleic acids may be transiently or stably transfected in the desired host cells, according to methods known in the art.

In certain embodiments, a polypeptide may be produced in vivo in an animal that has been engineered or transfected with a nucleic acid molecule encoding the polypeptide, according to methods known in the art.

Purification of CSF1R ECD Polypeptides

CSF1R ECDs or CSF1R ECD fusion molecules may be purified by various methods known in the art. Such methods include, but are not limited to, the use of affinity matrices or hydrophobic interaction chromatography. Suitable affinity ligands include any ligands of the CSF1R ECD or of the fusion partner, or antibodies thereto. For example, a Protein A, Protein G, Protein A/G, or an antibody affinity column may be used to bind to an Fc fusion partner to purify a CSF1R ECD fusion molecule. Antibodies to CSF1R ECD may also be used to purify CSF1R ECD or CSF1R ECD fusion molecules. Hydrophobic interactive chromatography, for example, a butyl or phenyl column, may also suitable for purifying certain polypeptides. Many methods of purifying polypeptides are known in the art.

Therapeutic Compositions and Methods

Routes of Administration and Carriers

In various embodiments, CSF1R ECD fusion molecules may be administered in vivo by various routes, including, but not limited to, oral, intravenous, intra-arterial, subcutaneous, parenteral, intranasal, intramuscular, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. A nucleic acid molecule encoding a CSF1R ECD and/or a CSF1R ECD fusion molecule may be coated onto gold microparticles and delivered intradermally by a particle bombardment device, or "gene gun," as described in the literature (see, e.g., Tang et al., *Nature* 356:152-154 (1992)). The appropriate formulation and route of administration may be selected according to the intended application.

In various embodiments, compositions comprising CSF1R ECDs or CSF1R ECD fusion molecules are provided in formulations with a wide variety of pharmaceutically acceptable carriers (see, e.g., Gennaro, *Remington: The Science and Practice of Pharmacy with Facts and Comparisons: Drugfacts Plus,* 20th ed. (2003); Ansel et al., *Pharmaceutical Dosage Forms and Drug Delivery Systems*, 7$^{th}$ ed., Lippencott Williams and Wilkins (2004); Kibbe et al., *Handbook of Pharmaceutical Excipients*, 3$^{rd}$ ed., Pharmaceutical Press (2000)). Various pharmaceutically acceptable carriers, which include vehicles, adjuvants, and diluents, are available. Moreover, various pharmaceutically acceptable auxiliary substances, such as pH adjusting and buffering agents, tonicity adjusting agents, stabilizers, wetting agents and the like, are also available. Certain non-limiting exemplary carriers include saline, buffered saline, dextrose, water, glycerol, ethanol, and combinations thereof.

In various embodiments, compositions comprising CSF1R ECDs or CSF1R ECD fusion molecules may be formulated for injection by dissolving, suspending, or emulsifying them in an aqueous or nonaqueous solvent, such as vegetable or other oils, synthetic aliphatic acid glycerides, esters of higher aliphatic acids, or propylene glycol; and if desired, with conventional additives such as solubilizers, isotonic agents, suspending agents, emulsifying agents, stabilizers and preservatives. In various embodiments, the compositions may be formulated for inhalation, for example, using pressurized acceptable propellants such as dichlorodifluoromethane, propane, nitrogen, and the like. The compositions may also be formulated, in various embodiments, into sustained release microcapsules, such as with biodegradable or non-biodegradable polymers. A non-limiting exemplary biodegradable formulation includes poly lactic acid-glycolic acid polymer. A non-limiting exemplary non-biodegradable formulation includes a polyglycerin fatty acid ester. Certain methods of making such formulations are described, for example, in EP 1 125 584 A1.

Pharmaceutical packs and kits comprising one or more containers, each containing one or more doses of a CSF1R ECD and/or a CSF1R ECD fusion molecule are also provided. In certain embodiments, a unit dosage is provided wherein the unit dosage contains a predetermined amount of a composition comprising a CSF1R ECD and/or a CSF1R ECD fusion molecule, with or without one or more additional agents. In certain embodiments, such a unit dosage is supplied in single-use prefilled syringe for injection. In various embodiments, the composition contained in the unit dosage may comprise saline, sucrose, or the like; a buffer, such as phosphate, or the like; and/or be formulated within a stable and effective pH range. Alternatively, in certain embodiments, the composition may be provided as a lyophilized powder that may be reconstituted upon addition of an appropriate liquid, for example, sterile water. In certain embodiments, the composition comprises one or more substances that inhibit protein aggregation, including, but not limited to, sucrose and arginine. In certain embodiments, a composition of the invention comprises heparin and/or a proteoglycan.

Pharmaceutical compositions are administered in an amount effective for treatment or prophylaxis of the specific indication. The therapeutically effective amount is typically dependent on the weight of the subject being treated, his or her physical or health condition, the extensiveness of the condition to be treated, or the age of the subject being treated. In general, the CSF1R ECD fusion molecules of the invention may be administered in an amount in the range of about 10 ug/kg body weight to about 100 mg/kg body weight per dose. In certain embodiments, the CSF1R ECD fusion molecules of the invention may be administered in an amount in the range of about 50 ug/kg body weight to about 5 mg/kg body weight per dose. In certain other embodiments, the CSF1R ECD fusion molecules of the invention may be administered in an amount in the range of about 100 ug/kg body weight to about 10 mg/kg body weight per dose. Optionally, the CSF1R ECD fusion molecules of the invention may be administered in an amount in the range of about 100 ug/kg body weight to about 20 mg/kg body weight per dose. Further optionally, the CSF1R ECD fusion molecules of the invention may be administered in an amount in the range of about 0.5 mg/kg body weight to about 20 mg/kg body weight per dose.

The CSF1R ECDs or CSF1R ECD fusion molecule compositions may be administered as needed to subjects. Determination of the frequency of administration may be made by persons skilled in the art, such as an attending physician based on considerations of the condition being treated, age of the subject being treated, severity of the condition being treated, general state of health of the subject being treated and the like. In certain embodiments, an effective dose of the CSF1R ECD or CSF1R ECD fusion molecule is administered to a subject one or more times. In various embodiments, an effective dose of the CSF1R ECD or CSF1R ECD fusion molecule is administered to the subject once a month, or more than once a month, for example, every two months or every three months or every six months. In other embodiments, an effective dose of the CSF1R ECD or CSF1R ECD fusion molecule is administered less than once a month, such as, for example, every two weeks or every week. An effective dose of the CSF1R ECD or CSF1R ECD fusion molecule is administered to the subject at least once. In certain embodiments, the effective dose of the CSF1R ECD or CSF1R ECD fusion molecule may be administered multiple times, including for periods of at least a month, at least six months, or at least a year.

Combination Therapy

CSF1R ECD fusion molecules of the invention may be administered alone or with other modes of treatment. They may be provided before, substantially contemporaneous with, or after other modes of treatment, for example, surgery, chemotherapy, radiation therapy, or the administration of a biologic, such as a therapeutic antibody.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Construction of Certain CSF1R-ECD-Fc Fusion Molecules

The cloning, expression, and purification of the CSF1R ECD fusion proteins are described. Clones of the CSF1R ECD fusion proteins were generated using PCR and conventional subcloning techniques. The GenBank accession numbers for the human CSF1R and mouse CSF1R genes and their encoded proteins are as follows: human CSF1R (NM_005221 and NP_005202) and mouse CSF1R (NM_001037859 and NP_001032948). For use in transient transfection of 293-6E cells, the hCSF1R.506, hCSF1R.512, mCSF1R.506, and mCSF1R.511 cDNAs are cloned into the EcoRI and BamHI sites of the multiple cloning site of the pTT5-J vector. The pTT5-J vector is a modified version of the pTT5 vector (provided by Yves Durocher, Biotechnology Research Institute, Montreal, Canada) that contains a cDNA encoding the Fc region of a human IgG1 protein (amino acid residues 233-464 of GenBank accession number AAH19337) in which the cysteine residue at position 237 is replaced with a serine residue (Fc C237S; SEQ ID NO.:19) inserted into the BamHI site of the multiple cloning site. This initial cloning step introduces a glycine-serine (GS) linker between the CSF and the Fc due to the nucleic acids introduced by the BamHI restriction enzyme site. The nucleotides encoding the GS linker may be subsequently removed using standard molecular biology techniques. The sequences of the resulting clones were verified, and the constructs (fused to the Fc alone (Fc) or to the GS linker followed by the Fc (GS-Fc)) were used for subcloning into other vectors.

For use in stable transfection of CHO cells, the hCSF1R.506-Fc and mCSF1R.506-Fc cDNAs were subcloned into the pDEF38 vector (ICOS Corporation, Bothell, Wash.). The hCSF1R.506-Fc/pTT5-J and mCSF1R.506-Fc/pTT5-J clones were used for subcloning into the pDEF38 vector using standard molecular biology techniques. The hCSF1R.506-Fc and mCSF1R.506 cDNAs were inserted into the XhoI and XbaI sites of the pDEF38 vector, and the sequences of the resulting clones were verified.

For experiments using minicircle DNA, the mCSF1R.506-GS-Fc and mCSF1R.511-GS-Fc cDNAs are subcloned into the p2xC31MasterSfi vector, which is a modified version of the pØC31.hFIX vector (Chen et al., *Human Gene Therapy* 16:126-131 (2005)) in which an SfiI site was introduced after the intron for the purpose of cloning. The mCSF1R.506-GS-Fc/pTT5-J and mCSF1R.511-GS-Fc/pTT5-J clones are used for subcloning into the p2xC31MasterSfi vector using standard molecular biology techniques. The mCSF1R.506-GS-Fc and mCSF1R.511-GS-Fc cDNAs are inserted into the SfiI site of the p2xC31MasterSfi vector, and the sequences of the resulting clones were verified.

The primary sequence and domain structure of the full-length human CSF1R extracellular domain, which consists of 512 amino acid residues, are shown in FIG. 1. The five IgG domains are denoted from N terminus to C terminus as IgG-1, IgG-2, IgG-3, IgG-4, and IgG-5. Two human CSF1R ECD clones were constructed and are fused to either an Fc alone or to a GS linker followed by an Fc at their C terminus: the full-length CSF1R ECD (hCSF1R.512-Fc or hCSF1R.512-GS-Fc, respectively) and a CSF1R ECD that excludes the last six C-terminal amino acid residues of the full-length human CSF1R ECD (referred to herein as hCSF1R.506-Fc or hCSF1R.506-GS-Fc). Two mouse CSF1R ECD clones were constructed and are fused to either an Fc alone or to a GS linker followed by an Fc at their C terminus: the full-length CSF1R ECD (mCSF1R.511-Fc or mCSF1R.511-GS-Fc) and a CSF1R ECD that excludes the last five C-terminal amino acid residues of the full-length mouse CSF1R ECD (referred to herein as mCSF1R.506-Fc or mCSF1R.506-GS-Fc). Table 1 lists the various CSF1R-ECD-Fc fusion proteins used in these examples with full protein names, SEQ ID NOs., brief descriptions, and short names.

TABLE 1

CSF1R-ECD-Fc Fusion Proteins

| Protein Name | SEQ ID NO. | Brief Description | Short name |
| --- | --- | --- | --- |
| hCSF1R-ECD.512-Fc | 5 | Full-length human CSF1R ECD fused to an Fc | hCSF1R.512-Fc or h512 |
| hCSF1R-ECD.506-Fc | 6 | Human CSF1R ECD lacking the six C-terminal residues fused to an Fc | hCSF1R.506-Fc or h506 |
| mCSF1R-ECD.511-Fc | 7 | Full-length mouse CSF1R ECD fused to an Fc | mCSF1R.511-Fc or m511 |
| mCSF1R-ECD.506-Fc | 8 | Mouse CSF1R ECD lacking the five C-terminal residues fused to an Fc | mCSF1R.506-Fc or m506 |
| hCSF1R-ECD.512-GS-Fc | 31 | Full-length human CSF1R ECD fused to GS-Fc | hCSF1R.512-GS-Fc |
| hCSF1R-ECD.506-GS-Fc | 32 | Human CSF1R ECD lacking the six C-terminal residues fused to GS-Fc | hCSF1R.506-GS-Fc |
| mCSF1R-ECD.511-GS-Fc | 33 | Full-length mouse CSF1R ECD fused to GS-Fc | mCSF1R.511-GS-Fc |
| mCSF1R-ECD.506-GS-Fc | 34 | Mouse CSF1R ECD lacking the five C-terminal residues fused to GS-Fc | mCSF1R.506-GS-Fc |

Example 2

Expression and Purification of CSF1R-ECD-Fc Fusion Proteins from 293-6E and CHO Host Cells In certain Examples herein, the fusion proteins were expressed in 293-6E or CHO cells. The hCSF1R.506-Fc/pTT5-J, hCSF1R.506-GS-Fc/pTT5-J, hCSF1R.512-Fc/pTT5-J, and hCSF1R.512-GS-Fc/pTT5-J plasmid constructs described in Example 1 were designed to provide transient expression in 293-6E host cells. The hCSF1R.506-Fc/pDEF38 and mCSF1R.506-Fc/pDEF38 plasmid constructs described in Example 1 were designed to provide stable expression in CHO cells (or its derivatives, such as DG44 cells (Invitrogen, Carlsbad, Calif.)).

Small scale production of CSF1R-ECD-Fc fusion proteins was achieved by transient transfection of 293-6E cells grown in polycarbonate Erlenmeyer flasks fitted with a vented screw cap, rotated on a table top shaker at 130 RPM, and grown in Freestyle medium (Invitrogen) at 37° C. in 5% $CO_2$ at cell densities ranging from $0.5 \times 10^6$ to $3 \times 10^6$ cells/ml. Typically, 50 ml of cell culture was grown in a 250 ml flask. One day before the transfection, the cells were diluted to $0.6 \times 10^6$ cells/ml in fresh Freestyle medium. On the day of transfection, the cells were in log phase ($0.8 \times 10^6$ to $1.5 \times 10^6$ cells/ml), and the cell density was adjusted to $1 \times 10^6$ cells/ml. The transfection mix was prepared by adding 2.5 ml sterile PBS to two 15 ml tubes; 50 ug of DNA was added to one tube, and 100 ul of PEI solution (sterile stock solution of 1 mg/ml polyethylenimine, linear, 25 kDa, pH 7.0 (Polysciences, Warrington, Wis.)) was added to the second tube; the contents of the two tubes were combined and allowed to incubate for 15 minutes at room temperature in order to form the transfection complex. The transfection complex was transferred to the 293-6E cell suspension culture, which was allowed to grow for 6-7 days at 37° C. in 5% $CO_2$. At 24 hours post-transfection, the supplement tryptone N1 (Catalog #19 553, OrganoTechnie S.A., (La Courneuve, France)) was added to 0.5% (v/v) to the cells to feed the cells and stimulate protein production. The tryptone N1 was made up as a 20% (w/v) stock solution in water, filter sterilized using a 0.2 um filter, and stored at 4° C. until use.

The 293-6E cultures expressing the CSF1R-ECD-Fc fusion proteins were harvested on either day 6 or 7 post-transfection when the cell viability was above 60%. The culture supernatant was clarified by centrifugation at 5,000×g at 4° C., and then loaded onto a 5 ml HiTrap Protein A HP column (GE Catalog #17-0403-01) that was equilibrated in Buffer A (0.5 M NaCl, 1×PBS). The column was washed using 10 column volumes of Buffer A, and the protein was eluted using a mix linear-step gradient over 15 column volumes of Buffer B (0.5 M NaCl, 0.1 M glycine, pH 2.7). The flow rate was 3 ml/min, and 1 ml fractions were collected into 100 ul of 1 M Tris buffer, pH 7.5, in a 96-well deep well block to neutralize the glycine. After purification, the fractions were pooled based on their purity (>95%) as determined by Coomassie staining of an SDS-PAGE gel, and their endotoxin level was determined (1-2 EU/mg). The CSF1R-ECD-Fc fusion protein was then dialyzed overnight in 1×PBS and filter sterilized.

Large scale production of CSF1R-ECD-Fc fusion proteins was achieved by stable transfection of CHO-derived DG44 cells, which are negative for dihydrofolate reductase (DHFR) expression. The expression vectors comprising hCSF1R.506-Fc/pDEF38 and mCSF1R.506-Fc/pDEF38 described in Example 1 were used for transfection of the DG44 cells for stable production of the hCSF1R.506-Fc and mCSF1R.506-Fc fusion proteins, respectively. In this process, untransfected DHFR-negative DG44 cells were cultured in CHO-CD serum-free medium (Irvine Scientific, Irvine, Calif.) supplemented with 8 mM L-Glutamine, 1× Hypoxanthine/Thymidine (HT; Invitrogen, Carlsbad, Calif.), and 18 ml/L of Pluronic-68 (Invitrogen, Carlsbad, Calif.). About 50 ug of plasmid DNA comprising hCSF1R.506-Fc/pDEF38 or mCSF1R.506-Fc/pDEF38 was first linearized by digestion with the PvuI restriction enzyme, ethanol precipitated, briefly air-dried, and subsequently resuspended in 400 ul of sterile, distilled water. Cultured DG44 host cells were seeded into a shaker flask at about $5 \times 10^5$ cells/ml the day before transfection, which reached about $1 \times 10^6$ cells/ml on the day of transfection. The cells were harvested, and about $1 \times 10^7$ cells per transfection were pelleted by centrifugation.

For transfection, each cell pellet was resuspended in 0.1 ml of Nucleofector V solution and transferred to an Amaxa Nucleofector cuvette (Amaxa, Cologne, Germany). About 5 ug of the resuspended linearized plasmid DNA was added and mixed with the suspended DG44 cells in the cuvette. The cells were then electroporated using an Amaxa Nucleofector Device II using program U-024. Electroporated cells were cultured in CHO-CD medium for two days and were then transferred into selective medium (CHO-CD serum free medium supplemented with 8 mM L-Glutamine, and 18 ml/L Pluronic-68). The selective medium was changed once every week. After about 12 days, 1 ug/ml R3 Long IGF-1 growth factor (Sigma, St. Louis, Mo.) was added to the medium and the culture was continued for another week until confluent. The supernatants from pools of stably transfected cell lines were assayed using a sandwich ELISA assay with an anti-Fc antibody to determine the protein titer. This transfection method generated an expression level of about 30 ug/ml of the hCSF1R.506-Fc and mCSF1R.506-Fc fusion proteins from the pools of stably transfected cells.

For stable cell line development, a total of one hundred 96-well plates and twenty-two 96-well plates, each seeded with a calculated density of three cells per well, were screened for hCSF1R.506-Fc and mCSF1R.506-Fc overexpression, respectively, using an anti-Fc antibody in an ELISA-based assay. Microscopic inspection of the top 500 hCSF1R.506-Fc-expressing wells showed that 250 of the wells had single colonies, which were expanded from 96-well plates to 6-well plates. Similarly, the top 24 mCSF1R.506-Fc-expressing wells were expanded from 96-well plates to 6-well plates. Titers were re-analyzed in a 6-well production model, and the top 48 hCSF1R.506-Fc clones and the top 12 mCSF1R.506-Fc clones were further expanded into T75 flasks in serum-free medium. Six of the hCSF1R.506-Fc clones were discarded due to a failure to grow during this process. Based on titer re-analysis, the top 25 hCSF1R.506-Fc clones and one mCSF1R.506-Fc clone were transferred into shaker flasks to begin the process of adapting the clones to suspension culture in CHO-CD medium. Titers were re-analyzed for the suspension cultures by seeding the cells at $0.5 \times 10^6$ cells/ml in 50 ml of culture medium in a 250 ml shaker flask. The cultures were fed on day 3 with 10% feeding medium (Irvine Scientific, Irvine, Calif.), and the culture temperature was shifted to 32° C. on the same day. On day 12, the spent medium was harvested, and the hCSF1R.506-Fc and mCSF1R.506-Fc protein levels were determined by ELISA. One of the hCSF1R.506-Fc clones and the mCSF1R.506-Fc clone were selected for process development based on high production levels and sialic acid content, and a research cell bank was prepared for each clone. The hCSF1R.506-Fc clone had a titer of 250 mg/l, and the mCSF1R.506-Fc clone had a titer of 100 mg/l when grown in shaker flasks.

Following expression and secretion of CSF1R-ECD-Fc fusion proteins from DG44 cells, Protein A affinity chromatography and SP cation exchange chromatography were used to purify the fusion proteins. The Protein A step served as an enrichment step, and the cation exchange step was both a secondary purification step and an endotoxin removal step. The cell supernatant was substantially purified by initial capture using mAbSelect Protein A Sepharose (GE Healthcare #17-5199), which is an affinity matrix used to bind to the Fc. Prior to loading, the column was equilibrated with five column volumes of sterile buffer A (10 mM potassium phosphate, pH 7.0, 500 mM NaCl). The cell supernatant was applied at a linear velocity of 152.9 cm/h on an XK50 column with a bed dimension of 5 cm×5 cm. Bound CSF1R-ECD-Fc was then washed with five column volumes of sterile buffer A. Elution was then carried out by applying a step gradient of sterile buffer B (100 mM glycine, pH 2.7, 20 mM NaCl) at a linear velocity of 305.7 cm/h for five column volumes. Two 250 ml fractions were collected into tubes containing 25 ml of 1 M Tris, pH 8.0 (Cellgro #46-031-CM) to neutralize the eluate. All bound CSF1R-ECD-Fc was completely eluted by 2.5 column volumes as judged by the A280 chromatographic trace and by SDS-PAGE.

The Protein A column eluate comprising the CSF1R-ECD-Fc was then diluted 10-fold with buffer C (50 mM MES, pH 5.5) and subjected to further purification by SP Sepharose High Performance (GE Healthcare #17-1087) cation exchange chromatography that was packed into an XK50 column with 200 ml of resin with a bed dimension of 5 cm×10 cm. The Protein A material was applied at a linear velocity of 79.1 cm/h. The bound protein was washed with 10 column volumes of buffer D (20 mM MES, pH 5.5, 20 mM NaCl). A 20 column volume linear gradient was applied from 0% to 100% buffer F (20 mM MES, pH 5.5, 300 mM NaCl), followed by five column volumes of buffer F. Elution fractions were analyzed by SDS-PAGE, and the CSF1R-ECD-Fc-containing fractions were pooled.

Following the purification, endotoxin levels were determined by the limulus amoebocyte lysate (LAL) using the Endosafe PTS assay system (Charles River Laboratories). Endotoxin levels were typically below 0.1 EU/mg at this step. The highly purified material from the cation exchange column was then concentrated to the desired concentration and dialyzed against a 10-fold volume of 1×PBS with one change of buffer of 10-fold volume after more than 3 hours at 4° C. The dialyzed material was collected after an additional 20 hours of dialysis. The purified samples were aliquotted and flash frozen by liquid nitrogen for long-term storage at −80° C.

Example 3

Figure 2:
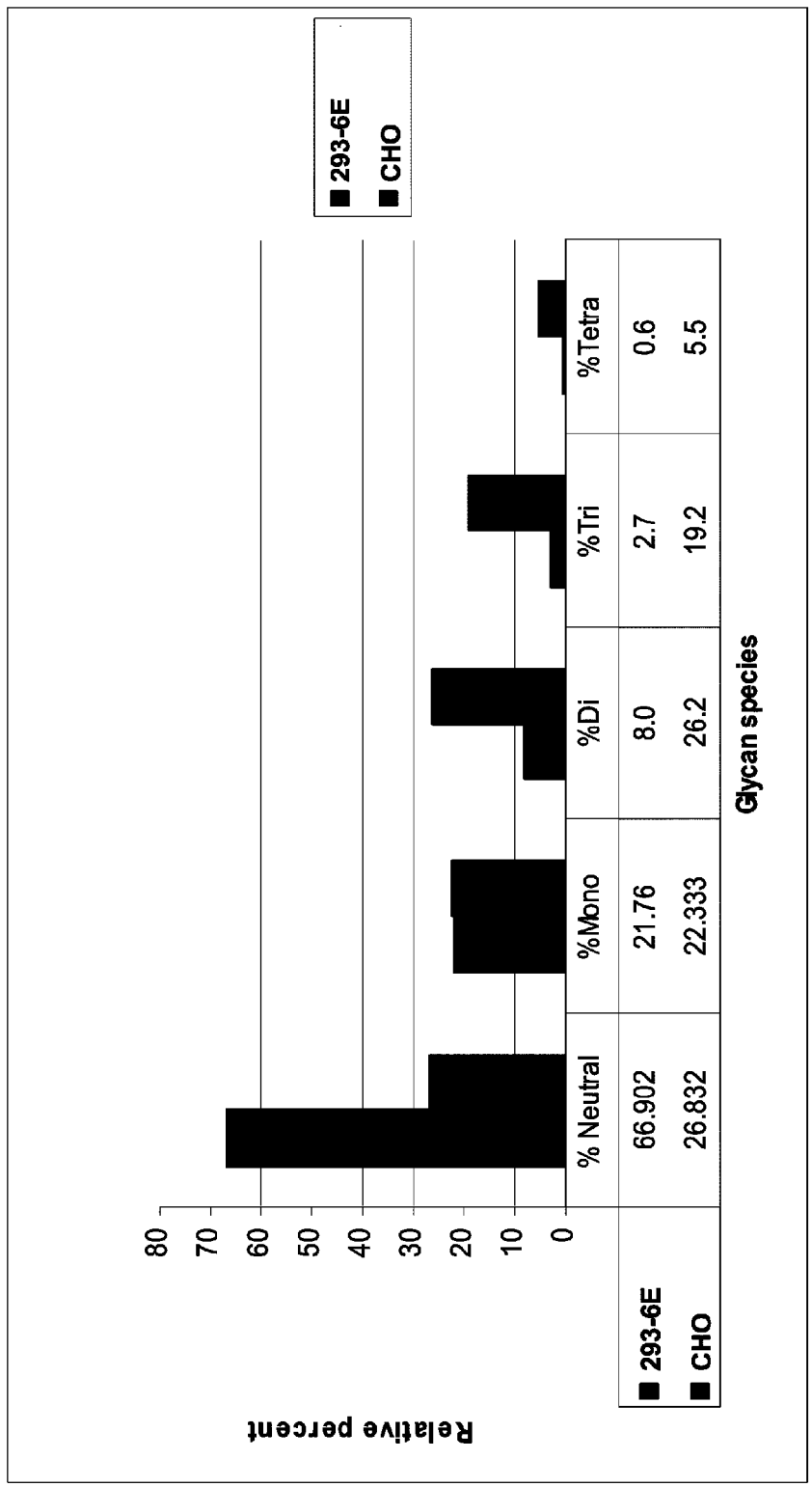
FIG. 2 shows the level of sialylation of the hCSF1R.506-Fc fusion protein produced in CHO host cells versus 293-6E host cells. Shown are the relative percentages of neutral, mono-, di-, tri-, and tetra-sialylation in CHO- and 293-6E-produced hCSF1R.506-Fc (corresponding values are shown in the table below the bar graph data).

Sialylation of the hCSF1R.506-Fc Fusion Protein in 293-63 Cells Versus CHO Cells Experiments were carried out to examine glycosylation and sialylation of the hCSF1R.506-Fc fusion protein expressed in 293-6E cells and in the CHO-derived DG44 cells. These experiments showed that the CHO- and 293-6E-produced CSF1R-ECD-Fc fusion proteins exhibited a similar overall level of glycosylation. However, the level of sialylation was higher in the CHO expression system relative to the 293-6E expression system. CHO-produced CSF1R-ECD-Fc fusion proteins exhibited a 10-fold higher level of tetra-sialylated glycans, a six-fold higher level of tri-sialylated glycans, a two-fold higher level of di-sialylated glycans, and a 2-fold reduction in the level of neutral glycans, which are involved in liver clearance. FIG. 2 shows the percentages of neutral, mono-, di-, tri-, and tetra-sialylation in CHO- and 293-6E-produced hCSF1R.506-Fc (corresponding values are shown below the graph).

Long-term storage of the purified CHO-produced fusion proteins at 4° C. (up to 5 weeks) showed little evidence of the laddering pattern observed with the 293-6E-produced fusion proteins. The CHO-produced CSF1R-ECD-Fc fusion protein has been concentrated to 90 mg/ml without any evidence of aggregation. Therefore, the increased level of sialylation associated with CHO-produced CSF1R-ECD-Fc fusion proteins leads to enhanced in vitro stability of the protein and also offers new routes of administration.

Example 4

CSF1R-ECD-Fc Fusion Proteins Bind to CSF1 and IL34

In order to determine whether the human CSF1R-ECD-Fc fusion proteins bind to the CSF1 and IL34 ligands, the hCSF1R.506-GS-Fc (SEQ ID NO.:32) and hCSF1R.512-GS-Fc (SEQ ID NO.:31) fusion proteins were expressed and purified from the culture media of 293-6E cells transiently transfected with the hCSF1R.506-GS-Fc/pTT5-J plasmid vector or the hCSF1R.512-GS-Fc/pTT5-J plasmid vector, respectively, as described in Example 2.

The CSF1 and IL34 ligand binding affinity and kinetics of the hCSF1R.506-GS-Fc and hCSF1R.512-GS-Fc fusion proteins were determined using Biacore® X surface plasmon resonance (SPR) technology (Uppsala, Sweden). CSF1 and IL34 are the only two ligands known to interact with the CSF1R ECD. The CSF1 and IL34 binding experiments were carried out using methodology similar to that described in Lin et al., Science 320:807-811, (2008).

The results of that experiment are shown in Tables 2 and 3.

TABLE 2

| IL34 Ligand Binding | | | |
|---|---|---|---|
| Protein Name | $k_a$ (l/Ms) | $k_d$ (l/s) | $K_D$ (M) |
| hCSF1R.512-GS-Fc | 1.19E+07 | 1.69E−05 | 1.42E−12 |
| hCSF1R.506-GS-Fc | 2.79E+07 | 1.90E−05 | 6.79E−13 |

TABLE 3

| CSF1 Ligand Binding | | | |
|---|---|---|---|
| Protein Name | $k_a$ (l/Ms) | $k_d$ (l/s) | $K_D$ (M) |
| hCSF1R.512-GS-Fc | 2.70E+07 | 1.30E−03 | 4.79E−11 |
| hCSF1R.506-GS-Fc | 4.62E+07 | 4.69E−04 | 1.02E−11 |

As shown in Tables 2 and 3, both the hCSF1R.512-GS-Fc and hCSF1R.506-GS-Fc fusion proteins bound to CSF1 and IL34, respectively, with high affinity. However, the hCSF1R.506-GS-Fc fusion protein had a 4-fold higher affinity for CSF1 and a 2-fold higher affinity for IL34 than the hCSF1R.512-GS-Fc fusion protein, as measured by the equilibrium dissociation constant ($K_D$). The results of these experiments are also summarized in FIG. 1.

These experiments demonstrated that the CSF1R ECD fusion proteins tested retained the ability to bind to both CSF1 and IL34. Surprisingly, the hCSF1R.506-GS-Fc fusion protein exhibited stronger binding than the hCSF1R.512-GS-Fc fusion protein to both CSF1 and IL34.

Example 5

CSF1R-ECD-Fc Fusion Proteins Inhibit Monocyte Viability

In order to determine whether the CSF1R-ECD-Fc fusion proteins are biologically active, their ability to inhibit human monocyte viability was examined. For these experiments, the hCSF1R.506-GS-Fc (SEQ ID NO.:32) and hCSF1R.512-GS-Fc (SEQ ID NO.:31) fusion proteins were expressed and purified from the culture media of 293-6E cells transiently transfected with the hCSF1R.506-GS-Fc/pTT5-J plasmid vector or the hCSF1R.512-GS-Fc/pTT5-J plasmid vector as described in Example 2.

Primary monocytes were isolated from human peripheral blood mononuclear cells (PBMC) through size sedimentation over Percoll columns as described (de Almeida et al., Mem Inst Oswaldo Cruz 95(2):221-223, (2000)). In this experiment, 1×10$^4$ freshly isolated human primary monocytes per well of a 96-well plate were incubated with the hCSF1R.506-GS-Fc or hCSF1R.512-GS-Fc fusion protein (0.01-120 nM) and the cells were incubated at 37° C. with 5% $CO_2$. After four days, ATP levels in the cells were determined using the CellTiter-Glo Luminescent Cell Viability Assay Kit (Promega, Cat. No. G7571), according to the manufacturer's instructions, as a measurement of cell viability.

Figure 3:
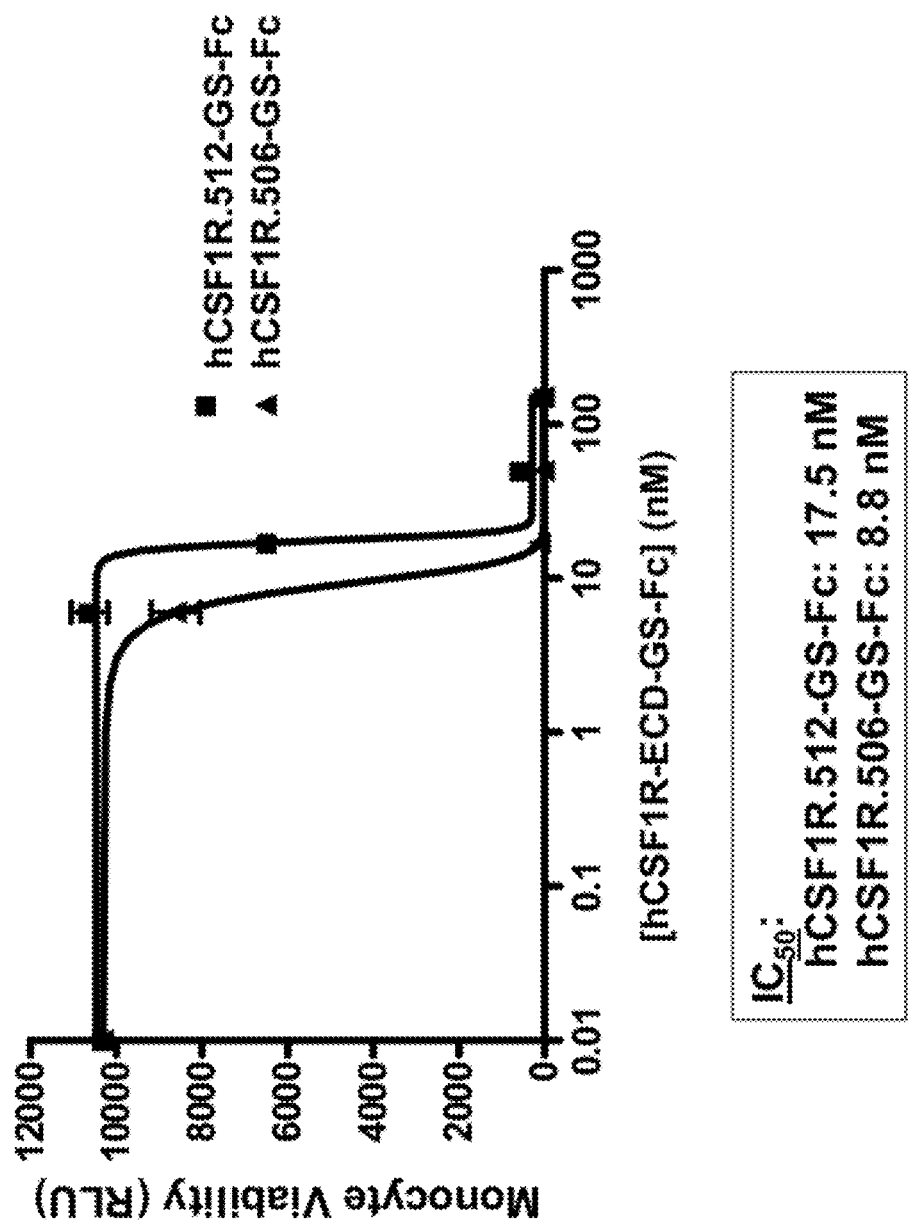
FIG. 3 shows the ability of the hCSF1R.512-GS-Fc and hCSF1R.506-GS-Fc fusion proteins to inhibit human monocyte viability and the corresponding $IC_{50}$ values.

As shown in FIG. 3, both the hCSF1R.512-GS-Fc and hCSF1R.506-GS-Fc fusion proteins inhibited human monocyte viability. The $IC_{50}$ value for hCSF1R.512-GS-Fc fusion protein was 17.5 nM, and the $IC_{50}$ value for the hCSF1R.506-GS-Fc fusion protein was 8.8 nM. These data demonstrated that the hCSF1R.506-GS-Fc fusion protein had a 2-fold higher inhibitory activity than the hCSF1R.512-GS-Fc fusion protein. The results of these experiments are also summarized in FIG. 1.

These experiments demonstrated that the CSF1R ECD fusion proteins retained the ability to inhibit human monocyte viability. Notably, the hCSF1R.506-GS-Fc fusion protein exhibited a stronger inhibitory activity than the hCSF1R.512-GS-Fc fusion protein.

Example 6

CSF1R-ECD-Fc Fusion Protein Inhibits CSF1- and IL34-Stimulated Monocyte Proliferation The hCSF1R.506 ECD fusion protein was further examined for its ability to inhibit CSF1- and IL34-stimulated human monocyte proliferation. For these experiments, the hCSF1R.506-Fc fusion protein (SEQ ID NO.:6) was expressed and purified from the culture media of CHO cells stably transfected with the hCSF1R.506-Fc/pDEF38 plasmid vector as described in Example 2.

Primary monocytes were isolated from human peripheral blood mononuclear cells (PBMC) through size sedimentation over Percoll columns as described in Example 5. The experiment to examine inhibition of CSF1- and IL34-stimulated monocyte proliferation was carried out using methodology similar to that described in Lin et al., Science 320:807-811, (2008).

Figure 4:
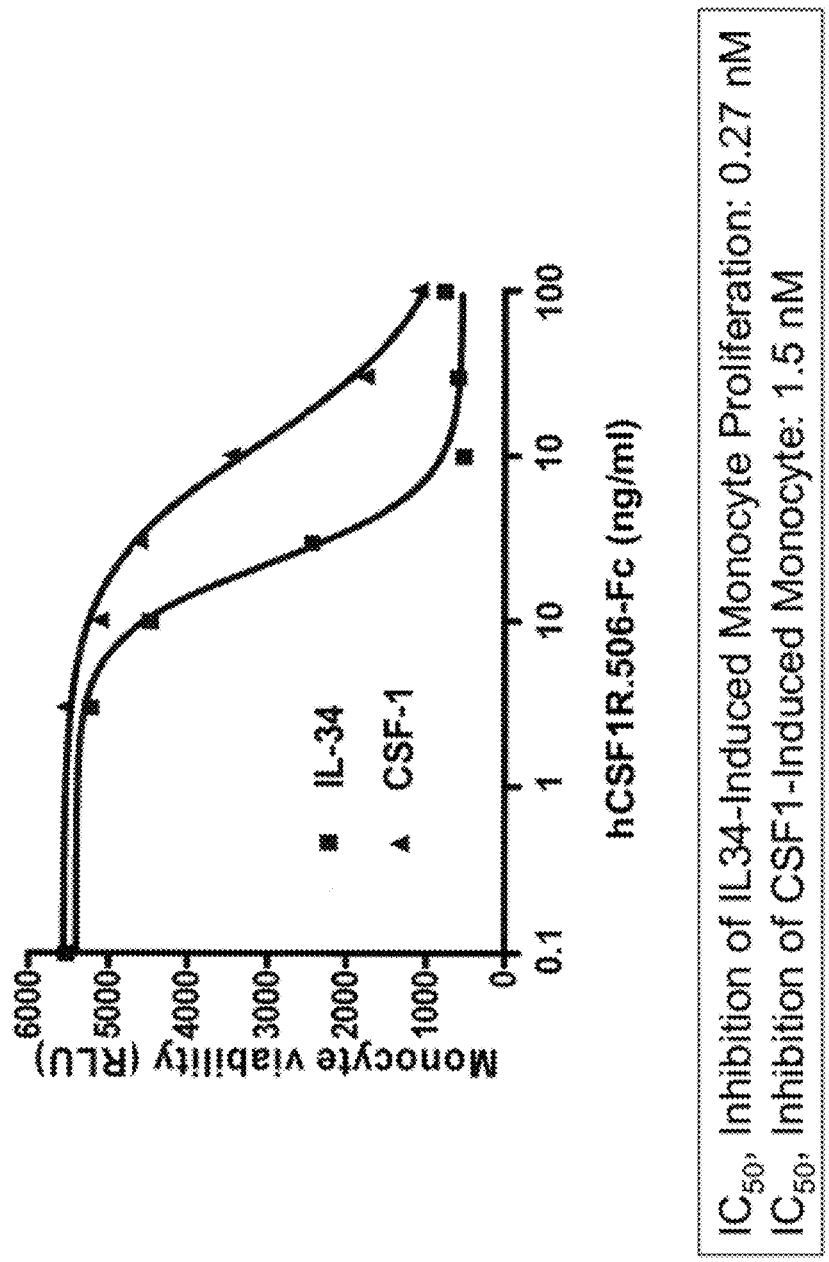
FIG. 4 shows the ability of the hCSF1R.506-Fc fusion protein to inhibit CSF1- and IL34-stimulated human monocyte proliferation.

The results of that experiment are shown in FIG. 4. As shown in FIG. 4, the hCSF1R.506-Fc fusion protein inhibited both CSF1- and IL34-stimulated proliferation of human monocytes. The $IC_{50}$ value for inhibition of IL34-induced monocyte proliferation was 0.27 nM, and the $IC_{50}$ value for inhibition of CSF1-induced monocyte proliferation was 1.5 nM. These experiments demonstrated that the hCSF1R.506-Fc fusion protein exhibited inhibitory activity against both CSF1- and IL34-stimulated human monocyte proliferation.

Example 7

CSF1R-ECD-Fc Fusion Protein Depletes Mouse Monocytes from Peripheral Blood

The mCSF1R.506-GS-Fc fusion protein (SEQ ID NO.:34) was expressed in vivo to determine whether it could deplete mouse monocytes from peripheral blood as a measure of in vivo biological activity. For these experiments, the minicircle DNA vector (mCSF1R.506-GS-Fc/p2xC31MasterSfi) containing the polynucleotides encoding mCSF1R.506-GS-Fc described in Example 1 was employed. For these experiments, 30 ug of CSF1R.506-GS-Fc-encoding minicircle DNA was injected into a C57BL/6 mouse tail vein by hydrodynamic tail vein transfection (TVT) as described (Ozaki et al., *J Immunol*, 173(9):5361-5371 (2004)). Saline was injected as a negative control. Approximately three weeks after the tail vein injection, peripheral blood cells were isolated and monocyte levels were determined using FACS analysis with anti-CD11b and anti-F4/80 antibodies according to the manufacturer's instruction (BD Biosciences) to detect monocyte marker-positive cells (F4/80$^+$, CD11b$^+$).

Figure 5:
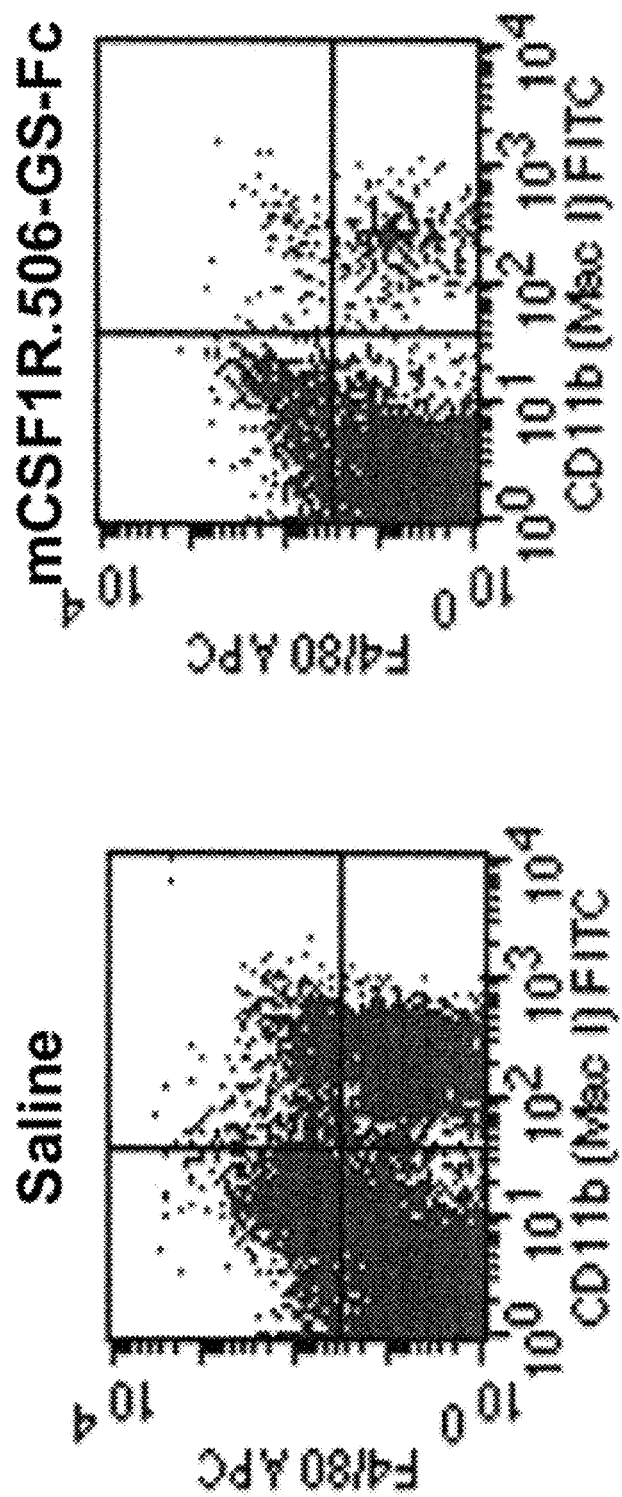
FIG. 5 shows the ability of the mCSF1R.506-GS-Fc fusion protein to deplete mouse monocytes from peripheral blood in vivo.

As shown in FIG. 5, in vivo expression of mCSF1R.506-GS-Fc led to a depletion of mouse monocytes from peripheral blood, as shown by a decrease in the number of monocyte marker-positive cells (F4/80$^+$, CD11b$^+$) in mice transfected with the mCSF1R.506-GS-Fc-encoding minicircle DNA. The results of this experiment demonstrated that the mCSF1R.506-GS-Fc fusion protein is biologically active in vivo.

Example 8

CSF1R-ECD-Fc Fusion Protein Inhibits Vitamin D3-Induced Hypercalcemia Caused by Osteolytic Bone Loss One of the CSF1R ECD fusion proteins was examined for its ability to inhibit osteoclast function and to protect against osteolytic bone loss in an established mouse hypercalcemia model. For these experiments, the mCSF1R.506-Fc fusion protein (SEQ ID NO.:8) was expressed and purified from the culture media of CHO cells stably transfected with the mCSF1R.506-Fc/pDEF38 plasmid vector as described in Example 2.

For the hypercalcemia experiments, 10-12 week old female C57BL/6 mice (Charles River) were used. On day −14, the mice were weighed, ear tagged, and randomly distributed into cages of five mice per group. The mice were assigned to one of four treatment groups:

Group 1: Albumin alone, 20 mg/kg, i.p., 3×/week starting on day −14, followed by daily dosing starting at day 0;

Group 2: mCSF1R.506-Fc alone (m506 alone), 20 mg/kg, i.p., 3×/week starting on day −14, followed by daily dosing starting at day 0;

Group 3: Albumin+Vitamin D3 (Albumin+Vit D3), Albumin 20 mg/kg, i.p., 3×/week starting on day −14, followed by daily dosing starting at day 0, and Vitamin D3, 100 ul (0.2 ug), s.c., qd×4 days starting at day 0;

Group 4: mCSF1.506-Fc+Vitamin D3 (m506+Vit D3), mCSF1R.506-Fc, 20 mg/kg, i.p., 3×/week starting on day −14, followed by daily dosing starting at day 0, Vitamin D3, 100 ul (0.2 ug), s.c., qd×4 days starting at day 0.

Starting on day −3, the mice were fed a low calcium diet (0.02% calcium; PMI Feeds) to limit calcium intake. Starting on day 0, the vitamin D3 dosing (Groups 2 and 4) or albumin vehicle dosing (Groups 1 and 3) began for all four groups. For Groups 3 and 4, the mice were injected with vitamin D3 two hours after the albumin or mCSF1.506-Fc injection, respectively. On day three, the mice were anesthetized and blood was collected by cardiac puncture at three hours after the final vitamin D3, mCSF1R.506-Fc, or vehicle dosing. Serum samples were assayed to determine: 1) serum ionized calcium concentrations using the QuantiChrom Calcium Assay Kit (BioAssay Systems, Cat. No. DICA-500) according to the manufacturer's instructions, and 2) serum pyridinoline (PYD) levels, which is a degradation product of bone collagen and a biomarker for bone resorption. Serum PYD levels were assayed using the MicroVue Serum PYD ELISA kit (# 8019, Quidel Corporation, San Diego, Calif.) according to the manufacturer's instructions.

Figure 6:
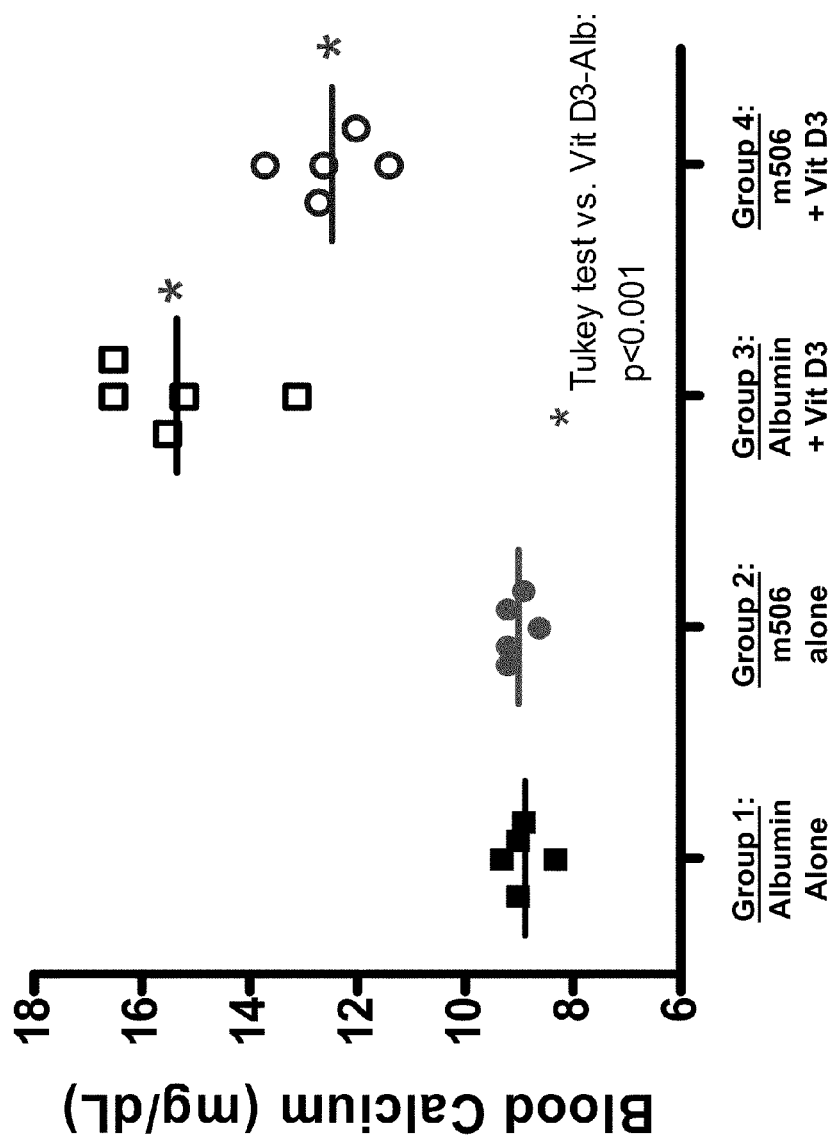
FIG. 6 shows the ability of the mCSF1R.506-Fc fusion protein (shown as m506) to inhibit vitamin D3-induced hypercalcemia in an in vivo mouse model.
Figure 7:
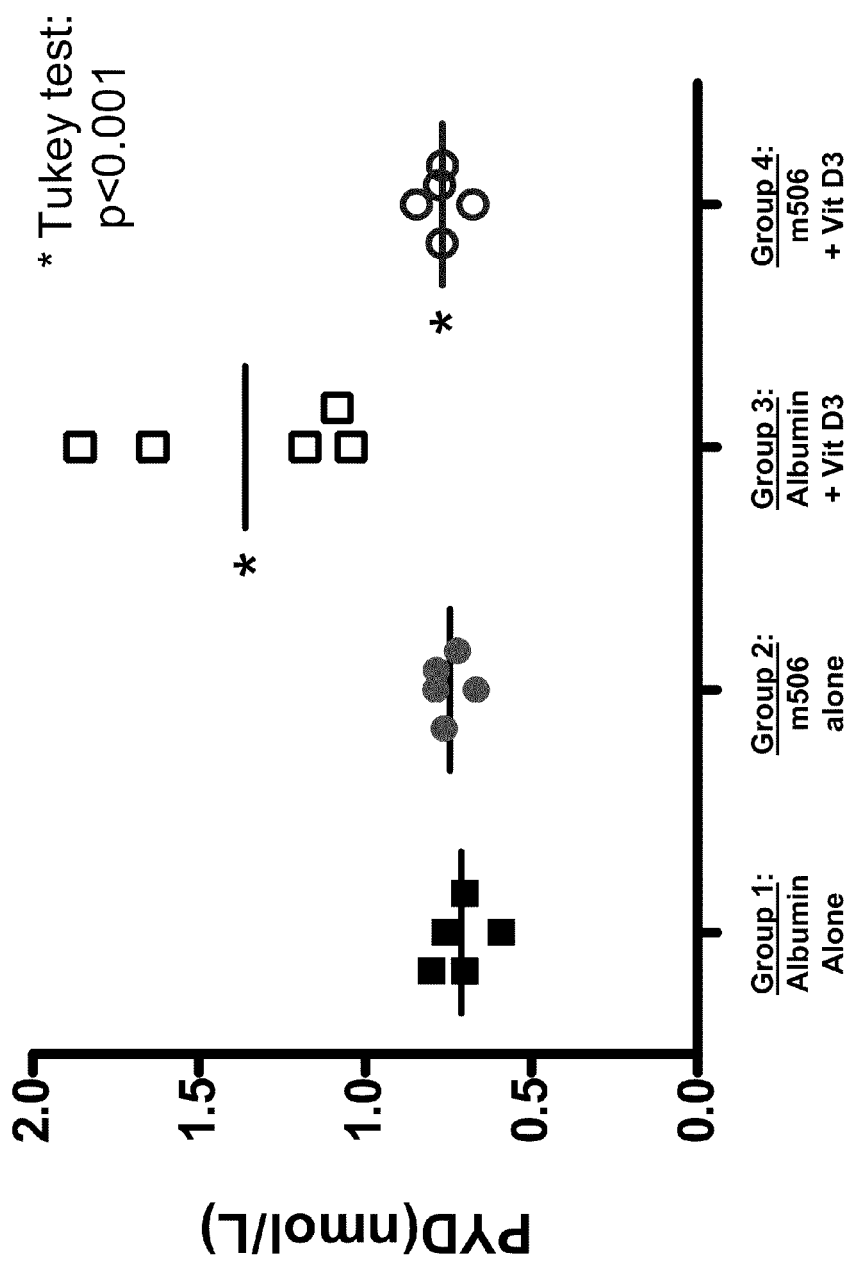
FIG. 7 shows the ability of the mCSF1R.506-Fc fusion protein (shown as m506) to inhibit vitamin D3-induced pyridinoline (PYD), an osteolytic bone loss marker, in an in vivo mouse model.

The results of these experiments are shown in FIGS. 6 and 7. As shown in FIG. 6, administration of vitamin D3 increased the serum level of ionized calcium, a marker for bone resorption. Treatment with mCSF1R.506-Fc intraperitoneally (i.p.) at 20 mg/kg once a day for two weeks significantly reduced the levels of ionized calcium in peripheral blood. A comparison between Group 3 (Albumin+Vitamin D3) and Group 4 (mCSF1R.506-Fc+Vitamin D3) showed that mCSF1R.506-Fc treatment resulted in a 44% reduction in ionized calcium levels in peripheral blood (Turkey test, Group 3 vs. Group 4: p<0.001). As shown in FIG. 7, administration of vitamin D3 significantly increased the level of PYD, a biomarker of bone degradation. Treatment with mCSF1R.506-Fc at 20 mg/kg once a day for two weeks also resulted in a reduction in PYD levels in peripheral blood. A comparison between Group 3 (Albumin+Vitamin D3) and Group 4 (mCSF1R.506-Fc+Vitamin D3) showed that mCSF1R.506-Fc treatment resulted in a 91% reduction in PYD levels in peripheral blood (Turkey test, Group 3 vs. Group 4: p<0.001).

Taken together, these experiments demonstrated that the mCSF1R.506-Fc ECD fusion protein effectively protected against vitamin D3-induced hypercalcemia and osteolytic bone loss.

Example 9

CSF1R-ECD-Fc Fusion Proteins Inhibit Tumor Growth and Metastasis

The CSF1R ECD fusion proteins were tested in an established mouse mammary carcinoma 4T1 model for their ability to inhibit tumor growth and/or metastasis. The 4T1 model is an aggressive mammary carcinoma cell line that spontaneously metastasizes to remote organs, including lung, spleen, and lymph node following subcutaneous implantation. The mouse CSF1R ECD fusion proteins were tested to determine whether they could inhibit the growth of the primary tumor and/or the spontaneous lung metastasis. For these experiments, the minicircle DNA vectors (mCSF1R.506-GS-Fc/p2xC31MasterSfi and mCSF1R.511-GS-Fc/p2xC31MasterSfi) containing the polynucleotides encoding the mCSF1R.506-GS-Fc (SEQ ID NO.:34) and mCSF1R.511-GS-Fc (SEQ ID NO.:33) fusion proteins, described in Example 1, were employed. The mCSF1R.506-Fc fusion protein (SEQ ID NO.:8) was expressed and purified from the culture media of CHO cells stably transfected with the mCSF1R.506-Fc/pDEF38 plasmid vector as described in Example 2. For these experiments, six week old female severe combined immunodeficient (SCID) mice (Charles River Laboratories) were used.

In the experiment to study anti-tumor and anti-metastasis activity following treatment by hydrodynamic transfection with minicircle DNA, the mice were weighed, ear tagged, and divided randomly into one of three treatment groups:

Group 1: Saline control;

Group 2: mCSF1R.506-GS-Fc-encoding minicircle DNA (m506 DNA), 40 ug/mouse;

Group 3: mCSF1R.511-GS-Fc-encoding minicircle DNA (m511 DNA), 40 ug/mouse.

Each treatment group consisted of 12 mice, which underwent three days of acclimation upon arrival. Hydrodynamic delivery of the minicircle DNA involved the use of 40 ug minicircle DNA resuspended in Ringer's solution in a volume corresponding to 8% body weight (for example, 20 grams× 8%≅1.6 ml). The resuspended minicircle DNA was administered as a bolus intravenous injection through the tail vein. Animals were observed for any adverse clinical signs for at least 20 minutes post dose. If the animals were not clinically normal as evidenced by regaining spontaneous ambulation and grooming behavior by one hour post dose, they were euthanized.

The 4T1 cells were cultured for two passages in RPMI 1640 medium supplemented with 10% fetal bovine serum and 1% L-glutamine at 37° C. in a humidified atmosphere containing 5% $CO_2$. One day after hydrodynamic transfection with the minicircle DNA, the 4T1 cells were harvested and implanted subcutaneously over the right flank of the mice at $1.25 \times 10^5$ cells/100 ul/mouse. Primary tumor volume and body weight were measured two times per week. When the primary tumor volume in the saline control group was equal to 2,500 mm$^3$, the mice were euthanized, and the lungs were collected and fixed in Bouin's solution. Metastatic lung nodules were counted manually.

In the experiment to study anti-tumor and anti-metastasis activity following treatment with purified mCSF1R.506-Fc fusion protein (m506 protein), the mice were weighed, ear tagged, and divided randomly into one of three treatment groups:

Group 1: Albumin control, 20 mg/kg, i.p., 3 times a week for up to four weeks;
Group 2: mCSF1R.506-Fc, 10 mg/kg, i.p., 3 times a week for up to four weeks;
Group 3: mCSF1R.506-Fc, 20 mg/kg, i.p., 3 times a week for up to four weeks. This experiment used 30 mice, which underwent five days of acclimation upon arrival. The 4T1 cells were cultured and implanted over the right flank as described above. The mice were randomized based on body weight into Groups 1-3, and each group consisted of 10 mice. The treatment (albumin control or purified mCSF1R.506-Fc fusion protein) was administered i.p. three times per week for up to four weeks. Tumor volume and body weight were measured three times per week. All of the mice were euthanized 25 days post-tumor implantation, and the lungs were collected for metastatic nodule counting as described above.

Figure 8:
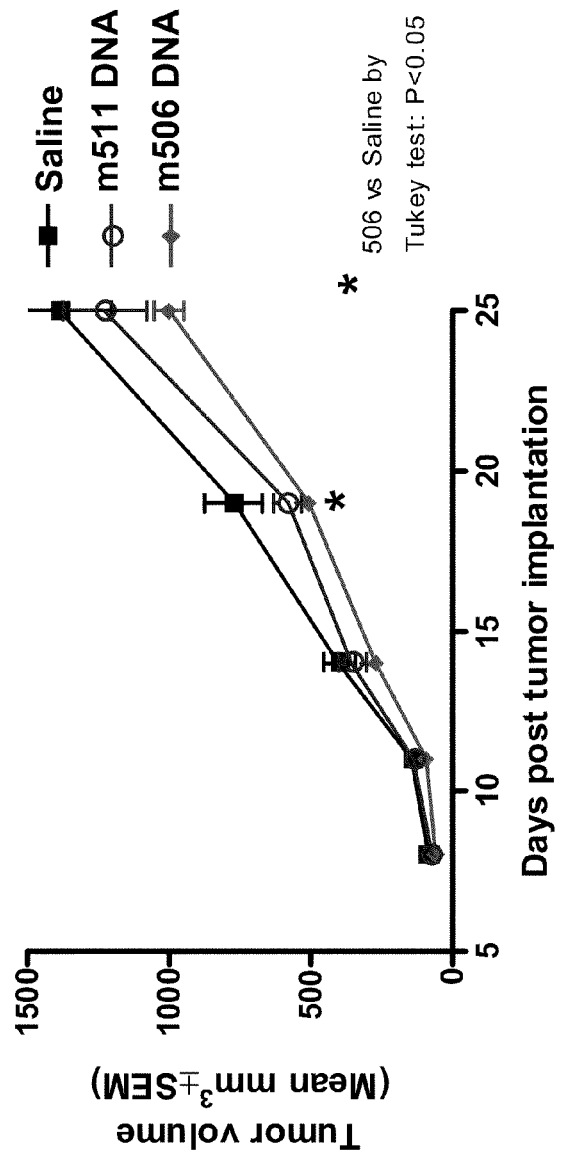
FIG. 8 shows the ability of the mCSF1R.511-GS-Fc-encoding minicircle DNA (shown as m511 DNA) and the mCSF1R.506-GS-Fc-encoding minicircle DNA (shown as m506 DNA) to inhibit primary tumor growth in an in vivo mouse model. Shown are tumor volumes in mice treated with the mCSF1R.511-Fc-encoding minicircle DNA or the mCSF1R.506-Fc-encoding minicircle DNA
Figure 9:
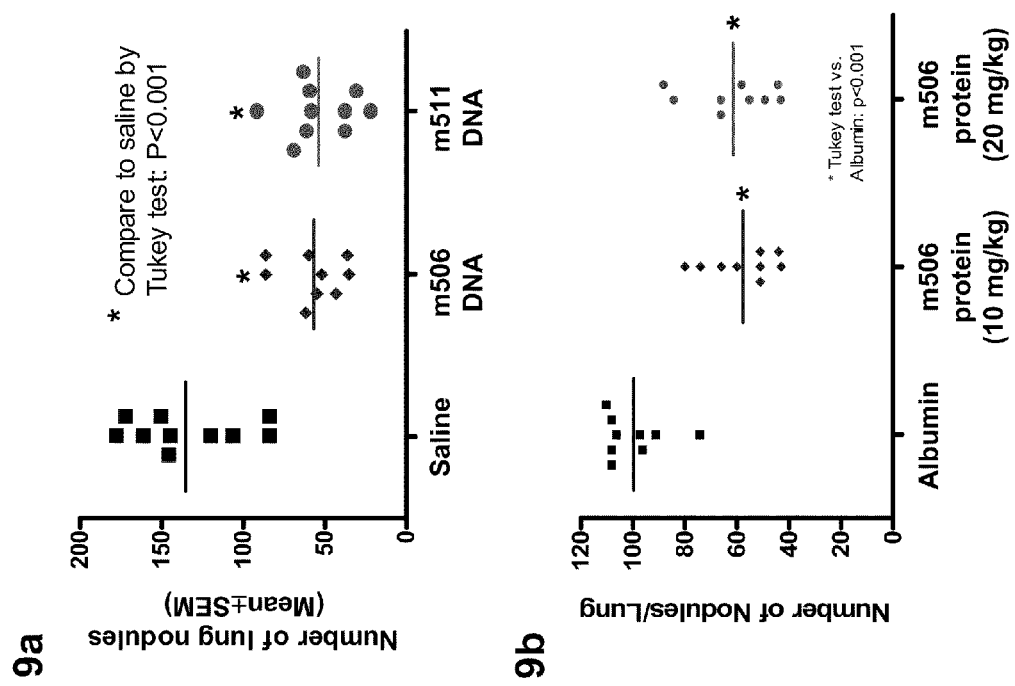
FIG. 9 shows the ability of the mCSF1R.511-GS-Fc-encoding minicircle DNA (shown as m511 DNA in FIG. 9a), the mCSF1R.506-GS-Fc-encoding minicircle DNA (shown as m506 DNA in FIG. 9a), and the mCSF1R.506-Fc fusion protein (shown as m506 protein in FIG. 9b) to inhibit tumor metastasis in an in vivo mouse model.

The results of these experiments to examine anti-tumor and anti-metastasis activities associated with CSF1R ECD fusion proteins are shown in FIGS. 8 and 9, respectively. As shown in FIG. 8, hydrodynamic transfection of mCSF1R.506-GS-Fc-encoding minicircle DNA resulted in 34% primary tumor growth inhibition on day 19 (Tukey test, p<0.05). Hydrodynamic transfection of mCSF1R.511-GS-Fc-encoding minicircle DNA showed a trend of tumor growth inhibition (24%, Tukey test, p>0.05) on day 19. Administration of the purified mCSF1R.506-Fc fusion protein did not inhibit tumor growth using the dose and schedule employed. As shown in FIG. 9, hydrodynamic transfection of mCSF1R.506-GS-Fc-encoding minicircle DNA or mCSF1R.511-GS-Fc-encoding minicircle DNA, and administration of purified mCSF1R.506-Fc protein all showed a reduction of spontaneous lung metastasis. Hydrodynamic transfection with mCSF1R.506-GS-Fc-encoding minicircle DNA or mCSF1R.511-GS-Fc-encoding minicircle DNA reduced the number of metastatic lung nodules by 61% and 60%, respectively (Tukey test, p<0.001). See FIG. 9a. Administration of purified mCSF1R.506-Fc fusion protein at a dose of 10 mg/kg or 20 mg/kg reduced the number of metastatic lung nodules by 42% or 38%, respectively (Tukey test, p<0.001). See FIG. 9b.

For the experiments involving hydrodynamic transfection of mCSF1R.511-GS-Fc-encoding minicircle DNA and mCSF1R.506-GS-Fc-encoding minicircle DNA, corresponding serum protein levels of mCSF1R.511-GS-Fc and mCSF1R.506-GS-Fc were determined in control mice that were hydrodynamically transfected but were not enrolled in the study. In this drug exposure monitoring study, 200 ul of whole blood were collected by retroorbital bleeding on days 3, 7, 14, and 25. The whole blood was transferred into EDTA-coated tubes (Becton Dickinson, Franklin Lakes, N.J.) and was spun down at 5000 rpm using a benchtop centrifuge (Eppendorf North America, Westbury, N.Y.). The plasma was collected and transferred into 1 ml eppendorf sample tubes. The levels of mCSF1R.506-GS-Fc and mCSF1R.511-GS-Fc proteins were analyzed using an Fc sandwich ELISA assay. In this assay, a Nunc Maxisorp 96-well plate (# 439-454, Thermo Fisher Scientific, Rochester, N.Y.) was coated with goat anti-human Fc polyclonal antibody (#A80-104A, Bethyl Labs, Montgomery, Tex.) at a concentration of 2 ug/ml overnight at 4° C. The wells were then blocked with 1% BSA (fraction V; Sigma #A3059) in PBS at room temperature for 2 hours. Purified mCSF1R-506-Fc was used as a standard and was added into plasma from naïve SCID mice at a starting concentration of 10 ug/ml. The purified mCSF1R-506-Fc standard was then serially diluted seven times at a ratio of 1:2 in PBS containing 1% BSA and 0.05% Tween 20 (the dilution buffer), and was added to the wells in duplicates. The plasma samples from the study were diluted 20-fold in the dilution buffer and were added to the wells in duplicates. The plate was incubated at room temperature for 90 minutes with agitation. After washing, the HRP-conjugated polyclonal goat anti-human IgG-Fc antibody was added at a 1:60000 dilution for 1 hour to detect the captured mCSF1R.506-GS-Fc or mCSF1R.511-GS-Fc fusion proteins. The TMB substrate (#TMBW-0100-01 BioFX Laboratories, Owings Mills, Md.) was added at a concentration of 10 ug/ml and was incubated at room temperature for 10 minutes. The optical density of the tested samples was read at 450 nm using a Microplate reader (Molecular Devices, Sunnyvale, Calif.).

The average serum protein levels of mCSF1R.511-GS-Fc in mice hydrodynamically transfected with the mCSF1R.511-GS-Fc-encoding minicircle DNA were 1706, 1037, 714, and 536 ug/ml on days 3, 7, 14, and 25, respectively. The average serum protein levels of mCSF1R.506-GS-Fc in mice hydrodynamically transfected with the mCSF1R.506-GS-Fc-encoding minicircle DNA were 1197, 775, 525, and 311 ug/ml on days 3, 7, 14, and 25, respectively. The serum protein levels of mCSF1R.506-GS-Fc and mCSF1R.511-GS-Fc in hydrodynamically transfected animals were much higher than in the animals dosed 3 times a week with purified mCSF1R-506-Fc protein at 10 mg/kg or 20 mg/kg, in which the trough levels were 144 or 256 ug/ml, respectively. This may explain why the inhibition of tumor growth was not observed in animals dosed with purified mCSF1R-506-Fc protein.

These experiments suggested that CSF1R ECD fusion proteins inhibit tumor growth and are capable of inhibiting spontaneous tumor metastasis in an aggressive tumor model.

Example 10

CSF1R-ECD-Fc Fusion Proteins Inhibit Cancer Metastasis-Induced Osteolytic Bone Loss The CSF1R ECD fusion proteins were also tested for their ability to inhibit cancer metastasis-induced osteolytic bone loss. These experiments were performed by vivoPharm Pty Ltd (Level 9, 195 North Terrace, Adelaide, SA 5000, Australia) in the established human breast cancer MDA-MB-468 intratibial bone metastasis model. This study examined the efficacy of mCSF1R.506-Fc (m506) and hCSF1R.506-Fc (h506) fusion proteins as monotherapies and in combination against the development and bone lytic activity of MDA-MB-468 tumors. The mCSF1R.506-Fc (SEQ ID NO.:8) and hCSF1R.506-Fc (SEQ ID NO.:6) fusion proteins were expressed and purified from the culture media of CHO cells stably transfected with the mCSF1R.506-Fc/pDEF38 plasmid vector or the hCSF1R.506-Fc/pDEF38 plasmid vector as described in Example 2.

For the MDA-MB-468 experiments, 60 female C.B-17-Igh-1$^b$-Prkdc SCID mice were inoculated intra-tibially with MDA-MB-468 human breast tumor cells. One day later (Day 0), the mice were implanted with a uniquely identified microchip and were then randomly divided into one of five groups:

Group 1: Albumin control, 10 mg/kg, i.p, 3×/week for 6 weeks;
Group 2: mCSF1R.506-Fc, 10 mg/kg, i.p, 3×/week for 6 weeks;
Group 3: hCSF1R.506-Fc 10 mg/kg, i.p, 3×/week for 6 weeks;
Group 4: mCSF1R.506-Fc+hCSF1R.506-Fc, 5 mg/kg each, i.p., 3×/week for 6 weeks;
Group 5: ZOMETA®, 0.1 mg/kg, s.c., qd for 6 weeks, no treatment on weekends.

Each group consisted of 12 mice. The effectiveness of each treatment was compared to the negative control group (Group 1).

Figure 10A:
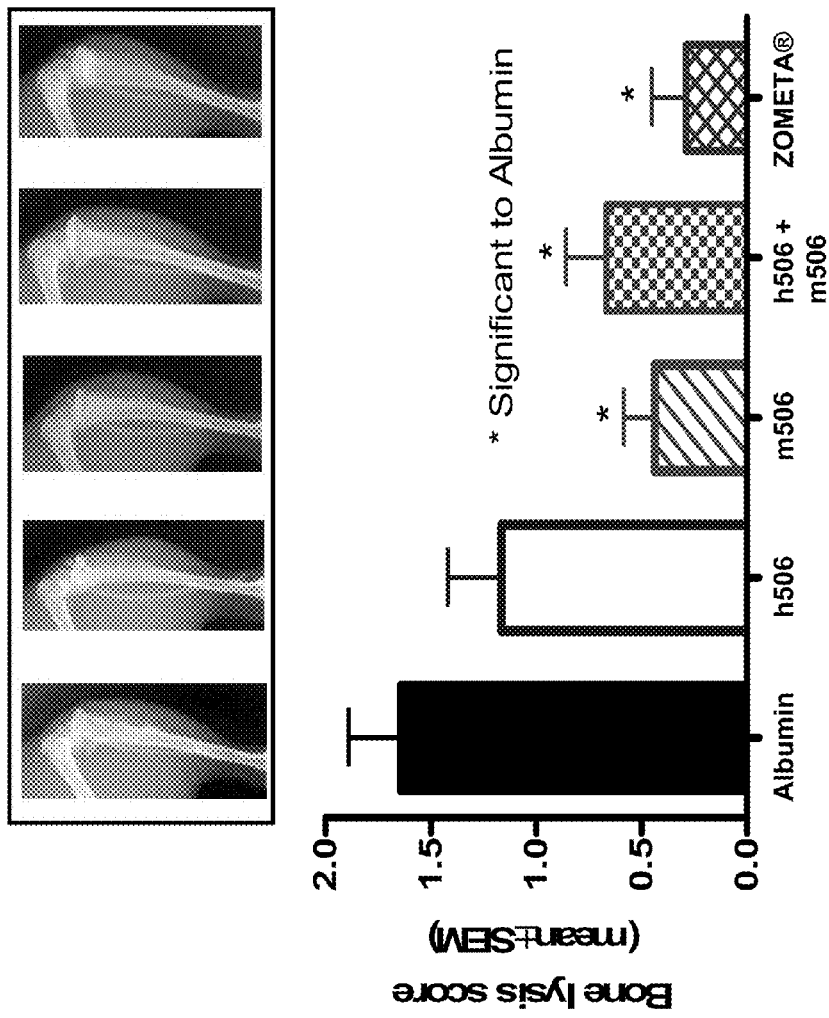
FIG. 10a shows bone lysis scores.

Treatment for each group was initiated 24 hours post-inoculation with the MDA-MB-468 tumor cells. Body weight was monitored twice a week. On the last day of the experiment (Day 41), the animals were anesthetized and X-ray images of the right and left tibiae was recorded. The X-ray images were analyzed for osteolytic bone damage using a ranking system in which the bone lysis scores ranged from 0 to 4, with a score of 4 indicating a high degree of bone lysis. Four individuals evaluated the bone lysis score in a blinded manner. The averages of the four individual bone lysis scores were determined and are shown in FIG. 10a. Whole blood was collected after X-ray imaging from all mice under anesthesia via cardiac puncture, and plasma samples were prepared for biomarker analysis. All excised tibiae were preserved and sent to SCANCO Medical AG (Switzerland) for assessment of bone density of the tumor implated tibiae using MicroCT scanning.

Figure 10B:
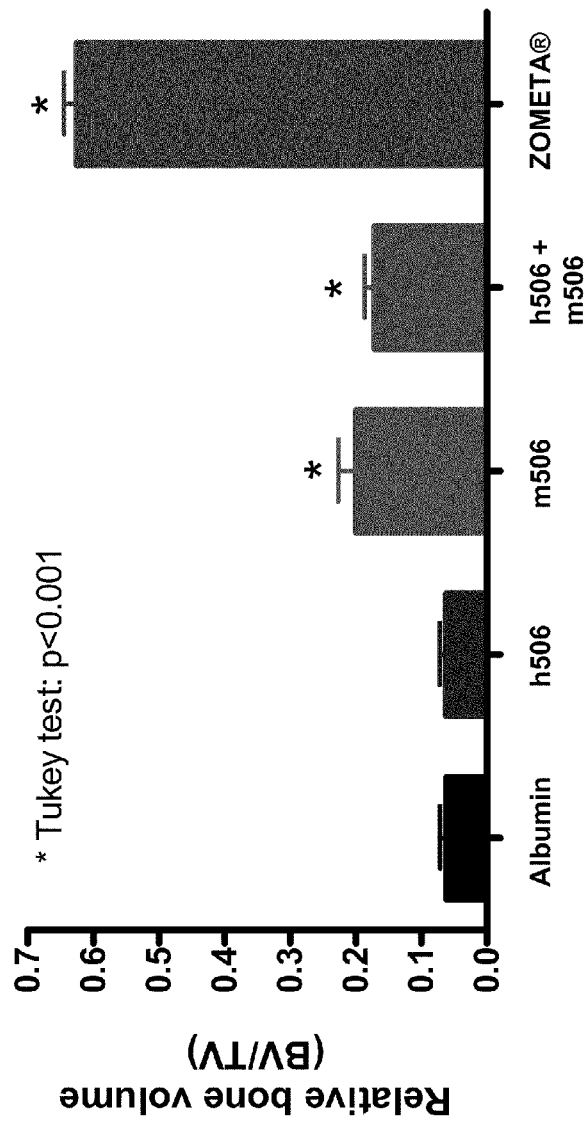
FIG. 10b shows relative bone volumes.

The results are shown in FIG. 10. As shown in FIG. 10a, relative to the albumin negative control, mCSF1R.506-Fc treatment reduced the bone lysis score by 73% (Tukey test: p <0.01), hCSF1R.506-Fc treatment reduced the bone lysis score by 29% (Turkey test: p>0.05), and the combination of mCSF1R.506-Fc plus hCSF1R.506-Fc reduced the bone lysis score by 59% (Tukey test: p<0.05); the positive control ZOMETA® reduced the bone lysis score by 82% (Tukey test: P<0.001). FIG. 10b shows the bone density of the tumor-implanted tibiae by microCT scanning, which demonstrated that the hCSF1R.506-Fc treatment group had lower mean bone volumes (BV) and relative bone volumes (BV/TV), which were similar to the albumin-treated group. The mCSF1R.506-Fc, mCSF1R.506-Fc plus hCSF1R.506-Fc, and ZOMETA® treatment groups preserved the relative bone volume by 2.2-, 1.7-, and 9.1-fold, respectively.

These experiments demonstrated that the mCSF1R.506-Fc treatment and the mCSF1R.506-Fc plus hCSF1R.506-Fc combination treatment inhibited cancer metastasis-induced osteolytic bone loss.

Table of Sequences

Table 4 provides certain sequences discussed herein. All CSF1R sequences are shown without the signal peptide, unless otherwise indicated.

TABLE 4

Sequences and Descriptions

| SEQ. ID. NO. | Description | Sequence |
|---|---|---|
| 1 | hCSF1R-ECD.512 | IPVIEPSVPE LVVKPGATVT LRCVGNGSVE WDGPPSPHWT LYSDGSSSIL STNNATFQNT GTYRCTEPGD PLGGSAAIHL YVKDPARPWN VLAQEVVVFE DQDALLPCLL TDPVLEAGVS LVRVRGRPLM RHTNYSFSPW HGFTIHRAKF IQSQDYQCSA LMGGRKVMSI SIRLKVQKVI PGPPALTLVP AELVRIRGEA AQIVCSASSV DVNFDVFLQH NNTKLAIPQQ SDFHNNRYQK VLTLNLDQVD FQHAGNYSCV ASNVQGKHST SMFFRVVESA YLNLSSEQNL IQEVTVGEGL NLKVMVEAYP GLQGFNWTYL GPFSDHQPEP KLANATTKDT YRHTFTLSLP RLKPSEAGRY SFLARNPGGW PALTFELTLR YPPEVSVIWT FINGSGTLLC AASGYPQPNV TWLQCSGHTD RCDEAQVLQV WDDPYPEVLS QEPFHKVTVQ SLLTVETLEH NQTYECRAHN SVGSGSWAFI PISAGAHTHP PDE |
| 2 | hCSF1R-ECD.506 | IPVIEPSVPE LVVKPGATVT LRCVGNGSVE WDGPPSPHWT LYSDGSSSIL STNNATFQNT GTYRCTEPGD PLGGSAAIHL YVKDPARPWN VLAQEVVVFE DQDALLPCLL TDPVLEAGVS LVRVRGRPLM RHTNYSFSPW HGFTIHRAKF IQSQDYQCSA LMGGRKVMSI SIRLKVQKVI PGPPALTLVP AELVRIRGEA AQIVCSASSV DVNFDVFLQH NNTKLAIPQQ SDFHNNRYQK VLTLNLDQVD FQHAGNYSCV ASNVQGKHST SMFFRVVESA YLNLSSEQNL IQEVTVGEGL NLKVMVEAYP GLQGFNWTYL GPFSDHQPEP KLANATTKDT YRHTFTLSLP RLKPSEAGRY SFLARNPGGW RALTFELTLR YPPEVSVIWT FINGSGTLLC AASGYPQPNV TWLQCSGHTD RCDEAQVLQV WDDPYPEVLS QEPFHKVTVQ SLLTVETLEH NQTYECRAHN SVGSGSWAFI PISAGAH |
| 3 | mCSF1R-ECD.511 | APVIEPSGPE LVVEPGETVT LRCVSNGSVE WDGPISPYWT LDPESPGSTL TTRNATFKNT GTYRCTELED PMAGSTTIHL YVKDPAHSWN LLAQEVTVVE GQEAVLPCLI TDPALKDSVS LMREGGRQVL RKTVYFFSPW RGFIIRKAKV LDSNTYVCKT MVNGRESTST GIWLKVNRVH PEPPQIKLEP SKLVRIRGEA AQIVCSATNA EVGFNVILKR GDTKLEIPLN SDFQDNYYKK VRALSLNAVD FQDAGIYSCV ASNDVGTRTA TMNFQVVESA YLNLTSEQSL LQEVSVGDSL ILTVHADAYP SIQHYNWTYL GPFFEDQRKL EFITQRAIYR YTFKLFLNRV KASEAGQYFL MAQNKAGWNN LTFELTLRYP PEVSVTWMPV NGSDVLFCDV SGYPQPSVTW MECRGHTDRC DEAQALQVWN DTHPEVLSQK PFDKVIIQSQ LPIGTLKHNM TYFCKTHNSV GNSSQYFRAV SLGQSKQLPD ES |
| 4 | mCSF1R-ECD.506 | APVIEPSGPE LVVEPGETVT LRCVSNGSVE WDGPISPYWT LDPESPGSTL TTRNATFKNT GTYRCTELED PMAGSTTIHL YVKDPAHSWN LLAQEVTVVE GQEAVLPCLI TDPALKDSVS LMREGGRQVL RKTVYFFSPW RGFIIRKAKV LDSNTYVCKT MVNGRESTST GIWLKVNRVH |

TABLE 4-continued

Sequences and Descriptions

| SEQ. ID. NO. | Description | Sequence |
|---|---|---|
| | | PEPPQIKLEP SKLVRIRGEA AQIVCSATNA EVGFNVILKR GDTKLEIPLN SDFQDNYYKK VRALSLNAVD FQDAGIYSCV ASNDVGTRTA TMNFQVVESA YLNLTSEQSL LQEVSVGDSL ILTVHADAYP SIQHYNWTYL GPFFEDQRKL EFITQRAIYR YTFKLFLNRV KASEAGQYFL MAQNKAGWNN LTFELTLRYP PEVSVTWMPV NGSDVLFCDV SGYPQPSVTW MECRGHTDRC DEAQALQVWN DTHPEVLSQK PFDKVIIQSQ LPIGTLKHNM TYFCKTHNSV GNSSQYFRAV SLGQSKQ |
| 5 | hCSF1R-ECD.512-Fc | IPVIEPSVPE LVVKPGATVT LRCVGNGSVE WDGPPSPHWT LYSDGSSSIL STNNATFQNT GTYRCTEPGD PLGGSAAIHL YVKDPARPWN VLAQEVVVFE DQDALLPCLL TDPVLEAGVS LVRVRGRPLM RHTNYSFSPW HGFTIHRAKF IQSQDYQCSA LMGGRKVMSI SIRLKVQKVI PGPPALTLVP AELVRIRGEA AQIVCSASSV DVNFDVFLQH NNTKLAIPQQ SDFHNNRYQK VLTLNLDQVD FQHAGNYSCV ASNVQGKHST SMFFRVVESA YLNLSSEQNL IQEVTVGEGL NLKVMVEAYP GLQGFNWTYL GPFSDHQPEP KLANATTKDT YRHTFTLSLP RLKPSEAGRY SFLARNPGGW RALTFELTLR YPPEVSVIWT FINGSGTLLC AASGYPQPNV TWLQCSGHTD RCDEAQVLQV WDDPYPEVLS QEPPHKVTVQ SLLTVETLEH NQTYECRAHN SVGSGSWAFI PISAGAHTHP PDEEPKSSDK THTCPPCPAP ELLGGPSVFL FPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PSRDELTKNQ VSLTCLVKGF YPSDIAVEWE SNGQPENNYK TTPPVLDSDG SFFLYSKLTV DKSRWQQGNV FSCSVMHEAL HNHYTQKSLS LSPGK |
| 6 | hCSF1R-ECD.506-Fc | IPVIEPSVPE LVVKPGATVT LRCVGNGSVE WDGPPSPHWT LYSDGSSSIL STNNATFQNT GTYRCTEPGD PLGGSAAIHL YVKDPARPWN VLAQEVVVFE DQDALLPCLL TDPVLEAGVS LVRVRGRPLM RHTNYSFSPW HGFTIHRAKF IQSQDYQCSA LMGGRKVMSI SIRLKVQKVI PGPPALTLVP AELVRIRGEA AQIVCSASSV DVNFDVFLQH NNTKLAIPQQ SDFHNNRYQK VLTLNLDQVD FQHAGNYSCV ASNVQGKHST SMFFRVVESA YLNLSSEQNL IQEVTVGEGL NLKVMVEAYP GLQGFNWTYL GPFSDHQPEP KLANATTKDT YRHTFTLSLP RLKPSEAGRY SFLARNPGGW RALTFELTLR YPPEVSVIWT FINGSGTLLC AASGYPQPNV TWLQCSGHTD RCDEAQVLQV WDDPYPEVLS QEPPHKVTVQ SLLTVETLEH NQTYECRAHN SVGSGSWAFI PISAGAHEPK SSDKTHTCPP CPAPELLGGP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV YTLPPSRDEL TKNQVSLTCL VKGFYPSDIA VEWESNGQPE NNYKTTPPVL DSDGSFFLYS KLTVDKSRWQ QGNVFSCSVM HEALHNHYTQ KSLSLSPGK |
| 7 | mCSF1R-ECD.511-Fc | APVIEPSGPE LVVEPGETVT LRCVSNGSVE WDGPISPYWT LDPESPGSTL TTRNATFKNT GTYRCTELED PMAGSTTIHL YVKDPAHSWN LLAQEVTVVE GQEAVLPCLI TDPALKDSVS LMREGGRQVL RKTVYFFSPW RGFIIRKAKV LDSNTYVCKT MVNGRESTST GIWLKVNRVH PEPPQIKLEP SKLVRIRGEA AQIVCSATNA EVGFNVILKR GDTKLEIPLN SDFQDNYYKK VRALSLNAVD FQDAGIYSCV ASNDVGTRTA TMNFQVVESA YLNLTSEQSL LQEVSVGDSL ILTVHADAYP SIQHYNWTYL GPFFEDQRKL |
| | | EFITQRAIYR YTFKLFLNRV KASEAGQYFL MAQNKAGWNN LTFELTLRYP PEVSVTWMPV NGSDVLFCDV SGYPQPSVTW MECRGHTDRC DEAQALQVWN DTHPEVLSQK PFDKVIIQSQ LPIGTLKHNM TYFCKTHNSV GNSSQYFRAV SLGQSKQLPD ESEPKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SRDELTKNQV SLTCLVKGFY PSDIAVEWES NGQPENNYKT TPPVLDSDGS FFLYSKLTVD KSRWQQGNVF SCSVMHEALH NHYTQKSLSL SPGK |
| 8 | mCSF1R-ECD.506-Fc | APVIEPSGPE LVVEPGETVT LRCVSNGSVE WDGPISPYWT LDPESPGSTL TTRNATFKNT GTYRCTELED PMAGSTTIHL YVKDPAHSWN LLAQEVTVVE GQEAVLPCLI TDPALKDSVS LMREGGRQVL RKTVYFFSPW RGFIIRKAKV LDSNTYVCKT MVNGRESTST GIWLKVNRVH PEPPQIKLEP SKLVRIRGEA AQIVCSATNA EVGFNVILKR GDTKLEIPLN SDFQDNYYKK VRALSLNAVD FQDAGIYSCV ASNDVGTRTA TMNFQVVESA YLNLTSEQSL LQEVSVGDSL ILTVHADAYP SIQHYNWTYL GPFFEDQRKL EFITQRAIYR YTFKLFLNRV KASEAGQYFL MAQNKAGWNN LTFELTLRYP PEVSVTWMPV NGSDVLFCDV SGYPQPSVTW MECRGHTDRC DEAQALQVWN DTHPEVLSQK PFDKVIIQSQ LPIGTLKHNM TYFCKTHNSV GNSSQYFRAV SLGQSKQEPK SSDKTHTCPP CPAPELLGGP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV YTLPPSRDEL TKNQVSLTCL VKGFYPSDIA VEWESNGQPE NNYKTTPPVL DSDGSFFLYS KLTVDKSRWQ QGNVFSCSVM HEALHNHYTQ KSLSLSPGK |
| 9 | hCSF1R signal peptide | MGPGVLLLLL VATAWHGQG |
| 10 | mCSF1R signal peptide | MELGPPLVLL LATVWHGQG |
| 11 | hCSF1R-ECD.512 with signal peptide | MGPGVLLLLL VATAWHGQGI PVIEPSVPEL VVKPGATVTL RCVGNGSVEW DGPPSPHWTL YSDGSSSILS TNNATFQNTG TYRCTEPGDP LGGSAAIHLY VKDPARPWNV LAQEVVVFED QDALLPCLLT DPVLEAGVSL VRVRGRPLMR HTNYSFSPWH GFTIHRAKFI QSQDYQCSAL MGGRKVMSIS IRLKVQKVIP GPPALTLVPA ELVRIRGEAA QIVCSASSVD VNFDVFLQHN NTKLAIPQQS DFHNNRYQKV LTLNLDQVDF QHAGNYSCVA SNVQGKHSTS MFFRVVESAY LNLSSEQNLI QEVTVGEGLN LKVMVEAYPG LQGFNWTYLG PFSDHQPEPK LANATTKDTY RHTFTLSLPR LKPSEAGRYS FLARNPGGWR ALTFELTLRY PPEVSVIWTF INGSGTLLCA ASGYPQPNVT WLQCSGHTDR CDEAQVLQVW DDPYPEVLSQ EPFHKVTVQS LLTVETLEHN QTYECRAHNS VGSGSWAFIP ISAGAHTHPP DE |
| 12 | hCSF1R-ECD.506 with signal peptide | MGPGVLLLLL VATAWHGQGI PVIEPSVPEL VVKPGATVTL RCVGNGSVEW DGPPSPHWTL YSDGSSSILS TNNATFQNTG TYRCTEPGDP LGGSAAIHLY VKDPARPWNV LAQEVVVFED QDALLPCLLT DPVLEAGVSL VRVRGRPLMR HTNYSFSPWH GFTIHRAKFI QSQDYQCSAL MGGRKVMSIS IRLKVQKVIP GPPALTLVPA ELVRIRGEAA QIVCSASSVD VNFDVFLQHN NTKLAIPQQS DFHNNRYQKV LTLNLDQVDF |

TABLE 4-continued

Sequences and Descriptions

| SEQ. ID. NO. | Description | Sequence |
|---|---|---|
| | | QHAGNYSCVA SNVQGKHSTS MFFRVVESAY LNLSSEQNLI QEVTVGEGLN LKVMVEAYPG LQGFNWTYLG PFSDHQPEPK LANATTKDTY RHTFTLSLPR LKPSEAGRYS FLARNPGGWR ALTFELTLRY PPEVSVIWTF INGSGTLLCA ASGYPQPNVT WLQCSGHTDR CDEAQVLQVW DDPYPEVLSQ EPFHKVTVQS LLTVETLEHN QTYECRAHNS VGSGSWAFIP ISAGAH |
| 13 | mCSF1R-ECD.511 with signal peptide | MELGPPLVLL LATVWHGQGA PVIEPSGPEL VVEPGETVTL RCVSNGSVEW DGPISPYWTL DPESPGSTLT TRNATFKNTG TYRCTELEDP MAGSTTIHLY VKDPAHSWNL LAQEVTVVEG QEAVLPCLIT DPALKDSVSL MREGGRQVLR KTVYFFSPWR GFIIRKAKVL DSNTYVCKTM VNGRESTSTG IWLKVNRVHP EPPQIKLEPS KLVRIRGEAA QIVCSATNAE VGFNVILKRG DTKLEIPLNS DFQDNYYKKV RALSLNAVDF QDAGIYSCVA SNDVGTRTAT MNFQVVESAY LNLTSEQSLL QEVSVGDSLI LTVHADAYPS IQHYNWTYLG PFFEDQRKLE FITQRAIYRY TFKLFLNRVK ASEAGQYFLM AQNKAGWNNL TFELTLRYPP EVSVTWMPVN GSDVLFCDVS GYPQPSVTWM ECRGHTDRCD EAQALQVWND THPEVLSQKP FDKVIIQSQL PIGTKLHNMT YFCKTHNSVG NSSQYFRAVS LGQSKQLPDE S |
| 14 | mCSF1R-ECD.506 with signal peptide | MELGPPLVLL LATVWHGQGA PVIEPSGPEL VVEPGETVTL RCVSNGSVEW DGPISPYWTL DPESPGSTLT TRNATFKNTG TYRCTELEDP MAGSTTIHLY VKDPAHSWNL LAQEVTVVEG QEAVLPCLIT DPALKDSVSL MREGGRQVLR KTVYFFSPWR GFIIRKAKVL DSNTYVCKTM VNGRESTSTG IWLKVNRVHP EPPQIKLEPS KLVRIRGEAA QIVCSATNAE VGFNVILKRG DTKLEIPLNS DFQDNYYKKV RALSLNAVDF QDAGIYSCVA SNDVGTRTAT MNFQVVESAY LNLTSEQSLL QEVSVGDSLI LTVHADAYPS IQHYNWTYLG PFFEDQRKLE FITQRAIYRY TFKLFLNRVK ASEAGQYFLM AQNKAGWNNL TFELTLRYPP EVSVTWMPVN GSDVLFCDVS GYPQPSVTWM ECRGHTDRCD EAQALQVWND THPEVLSQKP FDKVIIQSQL PIGTKLHNMT YFCKTHNSVG NSSQYFRAVS LGQSKQ |
| 15 | hCSF1R-ECD.512-Fc with signal peptide | MGPGVLLLLL VATAWHGQGI PVIEPSVPEL VVKPGATVTL RCVGNGSVEW DGPPSPHWTL YSDGSSSILS TNNATFQNTG TYRCTEPGDP LGGSAAIHLY VKDPARPWNV LAQEVVVFED QDALLPCLLT DPVLEAGVSL VRVRGRPLMR HTNYSFSPWH GFTIHRAKFI QSQDYQCSAL MGGRKVMSIS IRLKVQKVIP GPPALTLVPA ELVRIRGEAA QIVCSASSVD VNFDVFLQHN NTKLAIPQQS DFHNNRYQKV LTLNLDQVDF QHAGNYSCVA SNVQGKHSTS MFFRVVESAY LNLSSEQNLI QEVTVGEGLN LKVMVEAYPG LQGFNWTYLG PFSDHQPEPK LANATTKDTY RHTFTLSLPR LKPSEAGRYS FLARNPGGWR ALTFELTLRY PPEVSVIWTF INGSGTLLCA ASGYPQPNVT WLQCSGHTDR CDEAQVLQVW DDPYPEVLSQ EPFHKVTVQS LLTVETLEHN QTYECRAHNS VGSGSWAFIP ISAGAHTHPP DEEPKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SRDELTKNQV SLTCLVKGFY PSDIAVEWES NGQPENNYKT TPPVLDSDGS FFLYSKLTVD KSRWQQGNVF SCSVMHEALH NHYTQKSLSL SPGK |
| 16 | hCSF1R-ECD.506-Fc with signal peptide | MGPGVLLLLL VATAWHGQGI PVIEPSVPEL VVKPGATVTL RCVGNGSVEW DGPPSPHWTL YSDGSSSILS TNNATFQNTG TYRCTEPGDP LGGSAAIHLY VKDPARPWNV LAQEVVVFED QDALLPCLLT DPVLEAGVSL VRVRGRPLMR HTNYSFSPWH GFTIHRAKFI QSQDYQCSAL MGGRKVMSIS IRLKVQKVIP GPPALTLVPA ELVRIRGEAA QIVCSASSVD VNFDVFLQHN NTKLAIPQQS DFHNNRYQKV LTLNLDQVDF QHAGNYSCVA SNVQGKHSTS MFFRVVESAY LNLSSEQNLI QEVTVGEGLN LKVMVEAYPG LQGFNWTYLG PFSDHQPEPK LANATTKDTY RHTFTLSLPR LKPSEAGRYS FLARNPGGWR ALTFELTLRY PPEVSVIWTF INGSGTLLCA ASGYPQPNVT WLQCSGHTDR CDEAQVLQVW DDPYPEVLSQ EPFHKVTVQS LLTVETLEHN QTYECRAHNS VGSGSWAFIP ISAGAHEPKS SDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVMH EALHNHYTQK SLSLSPGK |
| 17 | mCSF1R-ECD.511-Fc with signal peptide | MELGPPLVLL LATVWHGQGA PVIEPSGPEL VVEPGETVTL RCVSNGSVEW DGPISPYWTL DPESPGSTLT TRNATFKNTG TYRCTELEDP MAGSTTIHLY VKDPAHSWNL LAQEVTVVEG QEAVLPCLIT DPALKDSVSL MREGGRQVLR KTVYFFSPWR GFIIRKAKVL DSNTYVCKTM VNGRESTSTG IWLKVNRVHP EPPQIKLEPS KLVRIRGEAA QIVCSATNAE VGFNVILKRG DTKLEIPLNS DFQDNYYKKV RALSLNAVDF QDAGIYSCVA SNDVGTRTAT MNFQVVESAY LNLTSEQSLL QEVSVGDSLI LTVHADAYPS IQHYNWTYLG PFFEDQRKLE FITQRAIYRY TFKLFLNRVK ASEAGQYFLM AQNKAGWNNL TFELTLRYPP EVSVTWMPVN GSDVLFCDVS GYPQPSVTWM ECRGHTDRCD EAQALQVWND THPEVLSQKP FDKVIIQSQL PIGTKLHNMT YFCKTHNSVG NSSQYFRAVS LGQSKQLPDE SEPKSSDKTH TCPPCPAPEL LGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS RDELTKNQVS LTCLVKGFYP SDIAVEWESN GQPENNYKTT PPVLDSDGSF FLYSKLTVDK SRWQQGNVFS CSVMHEALHN HYTQKSLSLS PGK |
| 18 | mCSF1R-ECD.506-Fc with signal peptide | MELGPPLVLL LATVWHGQGA PVIEPSGPEL VVEPGETVTL RCVSNGSVEW DGPISPYWTL DPESPGSTLT TRNATFKNTG TYRCTELEDP MAGSTTIHLY VKDPAHSWNL LAQEVTVVEG QEAVLPCLIT DPALKDSVSL MREGGRQVLR KTVYFFSPWR GFIIRKAKVL DSNTYVCKTM VNGRESTSTG IWLKVNRVHP EPPQIKLEPS KLVRIRGEAA QIVCSATNAE VGFNVILKRG DTKLEIPLNS DFQDNYYKKV RALSLNAVDF QDAGIYSCVA SNDVGTRTAT MNFQVVESAY LNLTSEQSLL QEVSVGDSLI LTVHADAYPS IQHYNWTYLG PFFEDQRKLE FITQRAIYRY TFKLFLNRVK ASEAGQYFLM AQNKAGWNNL TFELTLRYPP EVSVTWMPVN GSDVLFCDVS GYPQPSVTWM ECRGHTDRCD EAQALQVWND THPEVLSQKP FDKVIIQSQL PIGTKLHNMT YFCKTHNSVG NSSQYFRAVS LGQSKQEPKS SDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV |

TABLE 4-continued

Sequences and Descriptions

| SEQ. ID. NO. | Description | Sequence |
|---|---|---|
| | | KGFYPSDIAV EWESNGQPEN NYKTTPPVLD |
| | | SDGSFFLYSK LTVDKSRWQQ GNVFSCSVMH |
| | | EALHNHYTQK SLSLSPGK |
| 19 | Fc C237S | EPKSSDKTHT CPPCPAPELL GGPSVFLFPP |
| | | KPKDTLMISR TPEVTCVVVD VSHEDPEVKF |
| | | NWYVDGVEVH NAKTKPREEQ YNSTYRVVSV |
| | | LTVLHQDWLN GKEYKCKVSN KALPAPIEKT |
| | | ISKAKGQPRE PQVYTLPPSR DELTKNQVSL |
| | | TCLVKGFYPS DIAVEWESNG QPENNYKTTP |
| | | PVLDSDGSFF LYSKLTVDKS RWQQGNVFSC |
| | | SVMHEALHNH YTQKSLSLSP GK |
| 20 | Exemplary Fc #1 | ERKCCVECPP CPAPPVAGPS VFLFPPKPKD |
| | | TLMISRTPEV TCVVVDVSHE DPEVQFNWYV |
| | | DGVEVHNAKT KPREEQFNST FRVVSVLTVV |
| | | HQDWLNGKEY KCKVSNKGLP APIEKTISKT |
| | | KGQPREPQVY TLPPSREEMT KNQVSLTCLV |
| | | KGFYPSDIAV EWESNGQPEN NYKTTPPMLD |
| | | SDGSFFLYSK LTVDKSRWQQ GNVFSCSVMH |
| | | EALHNHYTQK SLSLSPGK |
| 21 | Exemplary Fc #2 | ESKYGPPCPS CPAPEFLGGP SVFLFPPKPK |
| | | DTLMISRTPE VTCVVVDVSQ EDPEVQFNWY |
| | | VDGVEVHNAK TKPREEQFNS TYRVVSVLTV |
| | | LHQDWLNGKE YKCKVSNKGL PSSIEKTISK |
| | | AKGQPREPQV YTLPPSQEEM TKNQVSLTCL |
| | | VKGFYPSDIA VEWESNGQPE NNYKTTPPVL |
| | | DSDGSFFLYS RLTVDKSRWQ EGNVFSCSVM |
| | | HEALHNHYTQ KSLSLSLGK |
| 22 | hCSF1R (full-length, no signal peptide) | IPVIEPSVPE LVVKPGATVT LRCVGNGSVE |
| | | WDGPPSPHWT LYSDGSSSIL STNNATFQNT |
| | | GTYRCTEPGD PLGGSAAIHL YVKDPARPWN |
| | | VLAQEVVVFE DQDALLPCLL TDPVLEAGVS |
| | | LVRVRGRPLM RHTNYSFSPW HGFTIHRAKF |
| | | IQSQDYQCSA LMGGRKVMSI SIRLKVQKVI |
| | | PGPPALTLVP AELVRIRGEA AQIVCSASSV |
| | | DVNFDVFLQH NNTKLAIPQQ SDFHNNRYQK |
| | | VLTLNLDQVD FQHAGNYSCV ASNVQGKHST |
| | | SMFFRVVESA YLNLSSEQNL IQEVTVGEGL |
| | | NLKVMVEAYP GLQGFNWTYL GPPFSDHQPEP |
| | | KLANATTKDT YRHTFTLSLP RLKPSEAGRY |
| | | SFLARNPGGW RALTFELTLR YPPEVSVIWT |
| | | FINGSGTLLC AASGYPQPNV TWLQCSGHTD |
| | | RCDEAQVLQV WDDPYPEVLS QEPFHKVTVQ |
| | | SLLTVETLEH NQTYECRAHN SVGSGSWAFI |
| | | PISAGAHTHP PDEFLFTPVV VACMSIMALL |
| | | LLLLLLLLYK YKQKPKYQVR WKIIESYEGN |
| | | SYTFIDPTQL PYNEKWEFPR NNLQFGKTLG |
| | | AGAFGKVVEA TAFGLGKEDA VLKVAVKMLK |
| | | STAHADEKEA LMSELKIMSH LGQHENIVNL |
| | | LGACTHGGPV LVITEYCCYG DLLNFLRRKA |
| | | EAMLGPSLSP GQDPEGGVDY KNIHLEKKYV |
| | | RRDSGFSSQG VDTYVEMRPV STSSNDSFSE |
| | | QDLDKEDGRP LELRDLLHFS SQVAQGMAFL |
| | | ASKNCIHRDV AARNVLLTNG HVAKIGDFGL |
| | | ARDIMNDSNY IVKGNARLPV KWMAPESIFD |
| | | CVYTVQSDVW SYGILLWEIF SLGLNPYPGI |
| | | LVNSKFYKLV KDGYQMAQPA FAPKNIYSIM |
| | | QACWALEPTH RPTFQQICSF LQEQAQEDRR |
| | | ERDYTNLPSS SRSGGSGSSS SELEEESSSE |
| | | HLTCCEQGDI AQPLLQPNNY QFC |
| 23 | hCSF1R (full-length, + signal peptide) | MGPGVLLLLL VATAWHGQGI PVIEPSVPEL |
| | | VVKPGATVTL RCVGNGSVEW DGPPSPHWTL |
| | | YSDGSSSILS TNNATFQNTG TYRCTEPGDP |
| | | LGGSAAIHLY VKDPARPWNV LAQEVVVFED |
| | | QDALLPCLLT DPVLEAGSVL VRVRGRPLMR |
| | | HTNYSFSPWH GFTIHRAKFI QSQDYQCSAL |
| | | MGGRKVMSIS IRLKVQKVIP GPPALTLVPA |
| | | ELVRIRGEAA QIVCSASSVD VNFDVFLQHN |
| | | NTKLAIPQQS DFHNNRYQKV LTLNLDQVDF |
| | | QHAGNYSCVA SNVQGKHSTS MFFRVVESAY |
| | | LNLSSEQNLI QEVTVGEGLN LKVMVEAYPG |
| | | LQGFNWTYLG PFSDHQPEPK LANATTKDTY |
| | | RHTFTLSLPR LKPSEAGRYS FLARNPGGWR |
| | | ALTFELTLRY PPEVSVIWTF INGSGTLLCA |
| | | ASGYPQPNVT WLQCSGHTDR CDEAQVLQVW |
| | | DDPYPEVLSQ EPFHKVTVQS LLTVETLEHN |
| | | QTYECRAHNS VGSGSWAFIP ISAGAHTHPP |
| | | DEFLFTPVVV ACMSIMALLL LLLLLLYKY |
| | | KQKPKYQVRW KIIESYEGNS YTFIDPTQLP |
| | | YNEKWEFPRN NLQFGKTLGA GAFGKVVEAT |
| | | AFGLGKEDAV LKVAVKMLKS TAHADEKEAL |
| | | MSELKIMSHL GQHENIVNLL GACTHGGPVL |
| | | VITEYCCYGD LLNFLRRKAE AMLGPSLSPG |
| | | QDPEGGVDYK NIHLEKKYVR RDSGFSSQGV |
| | | DTYVEMRPVS TSSNDSFSEQ DLDKEDGRPL |
| | | ELRDLLHFSS QVAQGMAFLA SKNCIHRDVA |
| | | ARNVLLTNGH VAKIGDFGLA RDIMNDSNYI |
| | | VKGNARLPVK WMAPESIFDC VYTVQSDVWS |
| | | YGILLWEIFS LGLNPYPGIL VNSKFYKLVK |
| | | DGYQMAQPAF APKNIYSIMQ ACWALEPTHR |
| | | PTFQQICSFL QEQAQEDRRE RDYTNLPSSS |
| | | RSGGSGSSSS ELEEESSSEH LTCCEQGDIA |
| | | QPLLQPNNYQ FC |
| 24 | mCSF1R (full-length, no signal peptide) | APVIEPSGPE LVVEPGETVT LRCVSNGSVE |
| | | WDGPISPYWT LDPESPGSTL TTRNATFKNT |
| | | GTYRCTELED PMAGSTTIHL YVKDPAHSWN |
| | | LLAQEVVVE GQEAVLPCLI TDPALKDSVS |
| | | LMREGGRQVL RKTVYFFSPW RGFIIRKAKV |
| | | LDSNTYVCKT MVNGRESTST GIWLKVNRVH |
| | | PEPPQIKLEP SKLVRIRGEA AQIVCSATNA |
| | | EVGFNVILKR GDTKLEIPLN SDFQDNYYKK |
| | | VRALSLNAVD FQDAGIYSCV ASNDVGTRTA |
| | | TMNFQVVESA YLNLTSEQSL LQEVSVGDSL |
| | | ILTVHADAYP SIQHYNWTYL GPFFEDQRKL |
| | | EFITQRAIYR YTFKLFLNRV KASEAGQYFL |
| | | MAQNKAGWNN LTFELTLRYP PEVSVTWMPV |
| | | NGSDVLFCDV SGYPQPSVTW MECRGHTDRC |
| | | DEAQALQVWN DTHPEVLSQK PFDKVIIQSQ |
| | | LPIGTLKHNM TYFCKTHNSV GNSSQYFRAV |
| | | SLGQSKQLPD ESLFTPVVVA CMSVMSLLVL |
| | | LLLLLLLYKY QKPKYQVRWK IIERYEGNSY |
| | | TFIDPTQLPY NEKWEFPRNN LQFGKTLGAG |
| | | AFGKVVEATA FGLGKEDAVL KVAVKMLKST |
| | | AHADEKEALM SELKIMSHLG QHENIVNLLG |
| | | ACTHGGPVLV ITEYCCYGDL LNFLRRKAEA |
| | | MLGPSLSPGQ DSEGDSSYKN IHLEKKYVRR |
| | | DSGFSSQGVD TYVEMRPVST SSSDSFFKQD |
| | | LDKEASRPLE LWDDLLHFSS VAQGMAFLAS |
| | | KNCIHRDVAA RNVLLTSGHV AKIGDFGLAR |
| | | DIMNDSNYVV KGNARLPVKW MAPESIFDCV |
| | | YTVQSDVWSY GILLWEIFSL GLNPYPGILV |
| | | NNKFYKLVKD GYQMAQPVFA PKNIYSIMQS |
| | | CWDLEPTRRP TFQQICFLLQ EQARLERRDQ |
| | | DYANLPSSGG SSGSDSGGGS SGGSSSEPEE |
| | | ESSSEHLACC EPGDIAQPLL QPNNYQFC |
| 25 | mCSF1R (full-length + signal peptide) | MELGPPLVLL LATVWHGQGA PVIEPSGPEL |
| | | VVEPGETVTL RCVSNGSVEW DGPISPYWTL |
| | | DPESPGSTLT TRNATFKNTG TYRCTELEDP |
| | | MAGSTTIHLY VKDPAHSWNL LAQEVTVVEG |
| | | QEAVLPCLIT DPALKDSVSL MREGGRQVLR |
| | | KTVYFFSPWR GFIIRKAKVL DSNTYVCKTM |
| | | VNGRESTSTG IWLKVNRVHP EPPQIKLEPS |
| | | KLVRIRGEAA QIVCSATNAE VGFNVILKRG |
| | | DTKLEIPLNS DFQDNYYKKV RALSLNAVDF |
| | | QDAGIYSCVA SNDVGTRTAT MNFQVVESAY |
| | | LNLTSEQSLL QEVSVGDSLI LTVHADAYPS |
| | | IQHYNWTYLG PFFEDQRKLE FITQRAIYRY |
| | | TFKLFLNRVK ASEAGQYFLM AQNKAGWNNL |
| | | TFELTLRYPP EVSVTWMPVN GSDVLFCDVS |
| | | GYPQPSVTWM ECRGHTDRCD EAQALQVWND |
| | | THPEVLSQKP FDKVIIQSQL PIGTLKHNMT |
| | | YFCKTHNSVG NSSQYFRAVS LGQSKQLPDE |

TABLE 4-continued

Sequences and Descriptions

| SEQ. ID. NO. | Description | Sequence |
|---|---|---|
| | | SLFTPVVVAC MSVMSLLVLL LLLLLYKYKQ KPKYQVRWKI IERYEGNSYT FIDPTQLPYN EKWEFPRNNL QFGKTLGAGA FGKVVEATAF GLGKEDAVLK VAVKMLKSTA HADEKEALMS ELKIMSHLGQ HENIVNLLGA CTHGGPVLVI TEYCCYGDLL NFLRRKAEAM LGPSLSPGQD SEGDSSYKNI HLEKKYVRRD SGFSSQGVDT YVEMRPVSTS SSDSFFKQDL DKEASRPLEL WDLLHFSSQV AQGMAFLASK NCIHRDVAAR NVLLTSGHVA KIGDFGLARD IMNDSNYVVK GNARLPVKWM APESIFDCVY TVQSDVWSYG ILLWEIFSLG LNPYPGILVN NKFYKLVKDG YQMAQPVFAP KNIYSIMQSC WDLEPTRRPT FQQICFLLQE QARLERRDQD YANLPSSGGS SGSDSGGGSS GGSSSEPEEE SSSEHLACCE PGDIAQPLLQ PNNYQFC |
| 26 | hCSF1R-ECD.511 | IPVIEPSVPE LVVKPGATVT LRCVGNGSVE WDGPPSPHWT LYSDGSSSIL STNNATFQNT GTYRCTEPGD PLGGSAAIHL YVKDPARPWN VLAQEVVVFE DQDALLPCLL TDPVLEAGVS LVRVRGRPLM RHTNYSFSPW HGFTIHRAKF IQSQDYQCSA LMGGRKVMSI SIRLKVQKVI PGPPALTLVP AELVRIRGEA AQIVCSASSV DVNFDVFLQH NNTKLAIPQQ SDFHNNRYQK VLTLNLDQVD FQHAGNYSCV ASNVQGKHST SMFFRVVESA YLNLSSEQNL IQEVTVGEGL NLKVMVEAYP GLQGFNWTYL GPFSDHQPEP KLANATTKDT YRHTFTLSLP RLKPSEAGRY SFLARNPGGW RALTFELTLR YPPEVSVIWT FINGSGTLLC AASGYPQPNV TWLQCSGHTD RCDEAQVLQV WDDPYPEVLS QEPFHKVTVQ SLLTVETLEH NQTYECRAHN SVGSGSWAFI PISAGAHTHP PD |
| 27 | hCSF1R-ECD.511 with signal peptide | MGPGVLLLLL VATAWHGQGI PVIEPSVPEL VVKPGATVTL RCVGNGSVEW DGPPSPHWTL YSDGSSSILS TNNATFQNTG TYRCTEPGDP LGGSAAIHLY VKDPARPWNV LAQEVVVFED QDALLPCLLT DPVLEAGVSL VRVRGRPLMR HTNYSFSPWH GFTIHRAKFI QSQDYQCSAL MGGRKVMSIS IRLKVQKVIP GPPALTLVPA ELVRIRGEAA QIVCSASSVD VNFDVFLQHN NTKLAIPQQS DFHNNRYQKV LTLNLDQVDF QHAGNYSCVA SNVQGKHSTS MFFRVVESAY LNLSSEQNLI QEVTVGEGLK LKVMVEAYPG LQGFNWTYLG PFSDHQPEPK LANATTKDTY RHTFTLSLPR LKPSEAGRYS FLARNPGGWR ALTFELTLRY PPEVSVIWTF INGSGTLLCA ASGYPQPNVT WLQCSGHTDR CDEAQVLQVW DDPYPEVLSQ EPFHKVTVQS LLTVETLEHN QTYECRAHNS VGSGSWAFIP ISAGAHTHPP D |
| 28 | hCSF1R-ECD.511-Fc | IPVIEPSVPE LVVKPGATVT LRCVGNGSVE WDGPPSPHWT LYSDGSSSIL STNNATFQNT GTYRCTEPGD PLGGSAAIHL YVKDPARPWN VLAQEVVVFE DQDALLPCLL TDPVLEAGVS LVRVRGRPLM RHTNYSFSPW HGFTIHRAKF IQSQDYQCSA LMGGRKVMSI SIRLKVQKVI PGPPALTLVP AELVRIRGEA AQIVCSASSV DVNFDVFLQH NNTKLAIPQQ SDFHNNRYQK VLTLNLDQVD FQHAGNYSCV ASNVQGKHST SMFFRVVESA YLNLSSEQNL IQEVTVGEGL NLKVMVEAYP GLQGFNWTYL GPFSDHQPEP KLANATTKDT YRHTFTLSLP RLKPSEAGRY SFLARNPGGW RALTFELTLR YPPEVSVIWT FINGSGTLLC AASGYPQPNV TWLQCSGHTD RCDEAQVLQV WDDPYPEVLS QEPFHKVTVQ SLLTVETLEH NQTYECRAHN SVGSGSWAFI PISAGAHTHP PDEPKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SRDELTKNQV SLTCLVKGFY PSDIAVEWES NGQPENNYKT TPPVLDSDGS FFLYSKLTVD KSRWQQGNVF SCSVMHEALH NHYTQKSLSL SPGK |
| 29 | hCSF1R-ECD.511-Fc with signal peptide | MGPGVLLLLL VATAWHGQGI PVIEPSVPEL VVKPGATVTL RCVGNGSVEW DGPPSPHWTL YSDGSSSILS TNNATFQNTG TYRCTEPGDP LGGSAAIHLY VKDPARPWNV LAQEVVVFED QDALLPCLLT DPVLEAGVSL VRVRGRPLMR HTNYSFSPWH GFTIHPAKFI QSQDYQCSAL MGGRKVMSIS IRLKVQKVIP GPPALTLVPA ELVRIRGEAA QIVCSASSVD VNFDVFLQHN NTKLAIPQQS DFHNNRYQKV LTLNLDQVDF QHAGNYSCVA SNVQGKHSTS MFFRVVESAY LNLSSEQNLI QEVTVGEGLK LKVMVEAYPG LQGFNWTYLG PFSDHQPEPK LANATTKDTY RHTFTLSLPR LKPSEAGRYS FLARNPGGWR ALTFELTLRY PPEVSVIWTF INGSGTLLCA ASGYPQPNVT WLQCSGHTDR CDEAQVLQVW DDPYPEVLSQ EPFHKVTVQS LLTVETLEHN QTYECRAHNS VGSGSWAFIP ISAGAHTHPP DEPKSSDKTH TCPPCPAPEL LGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS RDELTKNQVS LTCLVKGFYP SDIAVEWESN GQPENNYKTT PPVLDSDGSF FLYSKLTVDK SRWQQGNVFS CSVMHEALHN HYTQKSLSLS PGK |
| 30 | Fc C237S with N-terminal GS linker | GSEPKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SRDELTKNQV LTCLVKGFYP SDIAVEWESN GQPENNYKTT PPVLDSDGSF FLYSKLTVDK SRWQQGNVFS CSVMHEALHN HYTQKSLSLS PGK |
| 31 | hCSF1R-ECD.512Fc with GS linker | IPVIEPSVPE LVVKPGATVT LRCVGNGSVE WDGPPSPHWT LYSDGSSSIL STNNATFQNT GTYRCTEPGD PLGGSAAIHL YVKDPARPWN VLAQEVVVFE DQDALLPCLL TDPVLEAGVS LVRVRGRPLM RHTNYSFSPW HGFTIHRAKF IQSQDYQCSA LMGGRKVMSI SIRLKVQKVI PGPPALTLVP AELVRIRGEA AQIVCSASSV DVNFDVFLQH NNTKLAIPQQ SDFHNNRYQK VLTLNLDQVD FQHAGNYSCV ASNVQGKHST SMFFRVVESA YLNLSSEQNL IQEVTVGEGL NLKVMVEAYP GLQGFNWTYL GPFSDHQPEP KLANATTKDT YRHTFTLSLP RLKPSEAGRY SFLARNPGGW RALTFELTLR YPPEVSVIWT FINGSGTLLC AASGYPQPNV TWLQCSGHTD RCDEAQVLQV WDDPYPEVLS QEPFHKVTVQ SLLTVETLEH NQTYECRAHN SVGSGSWAFI PISAGAHTHP PDEGFEPKSS DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 32 | hCSF1R-ECD.506-Fc with GS linker | IPVIEPSVPE LVVKPGATVT LRCVGNGSVE WDGPPSPHWT LYSDGSSSIL STNNATFQNT GTYRCTEPGD PLGGSAAIHL YVKDPARPWN VLAQEVVVFE DQDALLPCLL TDPVLEAGVS LVRVRGRPLM RHTNYSFSPW HGFTIHRAKF IQSQDYQCSA LMGGRKVMSI SIRLKVQKVI PGPPALTLVP AELVRIRGEA AQIVCSASSV |

TABLE 4-continued

Sequences and Descriptions

| SEQ. ID. NO. | Description | Sequence |
|---|---|---|
| | | DVNFDVFLQH NNTKLAIPQQ SDFHNNRYQK VLTLNLDQVD FQHAGNYSCV ASNVQGKHST SMFFRVVESA YLNLSSEQNL IQEVTVGEGL NLKVMVEAYP GLQGFNWTYL GPFSDHQPEP KLANATTKDT YRHTFTLSLP RLKPSEAGRY SFLARNPGGW RALTFELTLR YPPEVSVIWT FINGSGTLLC AASGYPQPNV TWLQCSGHTD RCDEAQVLQV WDDPYPEVLS QEPFHKVTVQ SLLTVETLEH NQTYECRAHN SVGSGSWAFI PISAGAHGFE PKSSDKTHTC PPCPAPELLG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRD ELTKNQVSLT CLVKGFYPSD IAVEWESNGQ PENNYKTTPP VLDSDGSFFL YSKLTVDKSR WQQGNVFSCS VMHEALHNHY TQKSLSLSPG K |
| 33 | mCSF1R-ECD.511-Fc with GS linker | APVIEPSGPE LVVEPGETVT LRCVSNGSVE WDGPISPYWT LDPESPGSTL TTRNATFKNT GTYRCTELED PMAGSTTIHL YVKDPAHSWN LLAQEVTVVE GQEAVLPCLI TDPALKDSVS LMREGGRQVL RKTVYFFSPW RGFIIRKAKV LDSNTYVCKT MVNGRESTST GIWLKVNRVH PEPPQIKLEP SKLVRIRGEA AQIVCSATNA EVGFNVILKR GDTKLEIPLN SDFQDNYYKK VRALSLNAVD FQDAGIYSCV ASNDVGTRTA TMNFQVVESA YLNLTSEQSL LQEVSVGDSL ILTVHADAYP SIQHYNWTYL GPFFEDQRKL EFITQRAIYR YTFKLFLNRV KASEAGQYFL MAQNKAGWNN LTFELTLRYP PEVSVTWMPV NGSDVLFCDV SGYPQPSVTW MECRGHTDRC DEAQALQVWN DTHPEVLSQK PFDKVIIQSQ LPIGTLKHNN TYFCKTHNSV GNSSQYFRAV SLGQSKQLPD ESGFEPKSSD KTHTCPPCPA PELLGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSRDELTKN QVSLTCLVKG FYPSDIAVEW ESNGQPENNY KTTPPVLDSD GSFFLYSKLT VDKSRWQQGN VFSCSVMHEA LHNHYTQKSL SLSPGK |
| 34 | mCSF1R-ECD.506-Fc with GS linker | APVIEPSGPE LVVEPGETVT LRCVSNGSVE WDGPISPYWT LDPESPGSTL TTRNATFKNT GTYRCTELED PMAGSTTIHL YVKDPAHSWN LLAQEVTVVE GQEAVLPCLI TDPALKDSVS LMREGGRQVL RKTVYFFSPW RGFIIRKAKV LDSNTYVCKT MVNGRESTST GIWLKVNRVH PEPPQIKLEP SKLVRIRGEA AQIVCSATNA EVGFNVILKR GDTKLEIPLN SDFQDNYYKK VRALSLNAVD FQDAGIYSCV ASNDVGTRTA TMNFQVVESA YLNLTSEQSL LQEVSVGDSL ILTVHADAYP SIQHYNWTYL GPFFEDQRKL EFITQRAIYR YTFKLFLNRV KASEAGQYFL MAQNKAGWNN LTFELTLRYP PEVSVTWMPV NGSDVLFCDV SGYPQPSVTW MECRGHTDRC DEAQALQVWN DTHPEVLSQK PFDKVIIQSQ LPIGTLKHNM TYFCKTHNSV GNSSQYFRAV SLGQSKQGFE PKSSDKTHTC PPCPAPELLG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRD ELTKNQVSLT CLVKGFYPSD IAVEWESNGQ PENNYKTTPP VLDSDGSFFL YSKLTVDKSR WQQGNVFSCS VMHEALHNHY TQKSLSLSPG K |
| 35 | hCSF1R-ECD.512-Fc with signal peptide and GS linker | MGPGVLLLLL VATAWHGQGI PVIEPSVPEL VVKPGATVTL RCVGNGSVEW DGPPSPHWTL YSDGSSSILS TNNATFQNTG TYRCTEPGDP LGGSSAAIHLY VKDPARPWNV LAQEVVVFED QDALLPCLLT DPVLEAGVSL VRVRGRPLMR HTNYSFSPWH GFTIHRAKFI QSQDYQCSAL MGGRKVMSIS IRLKVQKVIP GPPALTLVPA ELVRIRGEAA QIVCSASSVD VNFDVFLQHN NTKLAIPQQS DFHNNRYQKV LTLNLDQVDF QHAGNYSCVA SNVQGKHSTS MFFRVVESAY LNLSSEQNLI QEVTVGEGLN LKVMVEAYPG LQGFNWTYLG PFSDHQPEPK LANATTKDTY RHTFTLSLPR LKPSEAGRYS FLARNPGGWR ALTFELTLRY PPEVSIWTF INGSGTLLCA ASGYPQPNVT WLQCSGHTDR CDEAQVLQVW DDPYPEVLSQ EPFHKVTVQS LLTVETLEHN QTYECRAHNS VGSGSWAFIP ISAGAHTHPP DEGFEPKSSD KTHTCPPCPA PELLGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSRDELTKN QVSLTCLVKG FYPSDIAVEW ESNGQPENNY KTTPPVLDSD GSFFLYSKLT VDKSRWQQGN VFSCSVMHEA LHNHYTQKSL SLSPGK |
| 36 | hCSF1R-ECD.506-Fc with signal peptide and GS linker | MGPGVLLLLL VATAWHGQGI PVIEPSVPEL VVKPGATVTL RCVGNGSVEW DGPPSPHWTL YSDGSSSILS TNNATFQNTG TYRCTEPGDP LGGSSAAIHLY VKDPARPWNV LAQEVVVFED QDALLPCLLT DPVLEAGVSL VRVRGRPLMR HTNYSFSPWH GFTIHRAKFI QSQDYQCSAL MGGRKVMSIS IRLKVQKVIP GPPALTLVPA ELVRIRGEAA QIVCSASSVD VNFDVFLQHN NTKLAIPQQS DFHNNRYQKV LTLNLDQVDF QHAGNYSCVA SNVQGKHSTS MFFRVVESAY LNLSSEQNLI QEVTVGEGLN LKVMVEAYPG LQGFNWTYLG PFSDHQPEPK LANATTKDTY RHTFTLSLPR LKPSEAGRYS FLARNPGGWR ALTFELTLRY PPEVSVIWTF INGSGTLLCA ASGYPQPNVT WLQCSGHTDR CDEAQVLQVW DDPYPEVLSQ EPFHKVTVQS LLTVETLEHN QTYECRAHNS VGSGSWAFIP ISAGAHGFEP KSSDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 37 | mCSF1R-ECD.511-Fc with signal peptide | MELGPPLVLL LATVWHGQGA PVIEPSGPEL VVEPGETVTL RCVSNGSVEW DGPISPYWTL DPESPGSTLT TRNATFKNTG TYRCTELEDP MAGSTTIHLY VKDPAHSWNL LAQEVTVVEG QEAVLPCLIT DPALKDSVSL MREGGRQVLR KTVYFFSPWR GFIIRKAKVL DSNTYVCKTM VNGRESTSTG IWLKVNRVHP EPPQIKLEPS KLVRIRGEAA QIVCSATNAE VGFNVILKRG DTKLEIPLNS DFQDNYYKKV RALSLNAVDF QDAGIYSCVA SNDVGTRTAT MNFQVVESAY LNLTSEQSLL QEVSVGDSLI LTVHADAYPS IQHYNWTYLG PFFEDQRKLE FITQRAIYRY TFKLFLNRVK ASEAGQYFLM AQNKAGWNNL TFELTLRYPP EVSVTWMPVN GSDVLFCDVS GYPQPSVTWM ECRGHTDRCD EAQALQVWND THPEVLSQKP FDKVIIQSQL PIGTLKHNMT YFCKTHNSVG NSSQYFRAVS LGQSKQLPDE SGFEPKSSDK THTCPPCPAP ELLGGPSVFL FPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PSRDELTKNQ |

TABLE 4-continued

Sequences and Descriptions

| SEQ. ID. NO. | Description | Sequence |
|---|---|---|
| | | VSLTCLVKGF YPSDIAVEWE SNGQPENNYK TTPPVLDSDG SFFLYSKLTV DKSRWQQGNV FSCSVMHEAL HNHYTQKSLS LSPGK |
| 38 | mCSF1R-ECD.506-Fc with signal peptide and GS linker | MELGPPLVLL LATVWHGQGA PVIEPSGPEL VVEPGETVTL RCVSNGSVEW DGPISPYWTL DPESPGSTLT TRNATFKNTG TYRCTELEDP MAGSTTIHLY VKDPAHSWNL LAQEVTVVEG QEAVLPCLIT DPALKDSVSL MREGGRQVLR KTVYFFSPWR GFIIRKAKVL DSNTYVCKTM VNGRESTSTG IWLKVNRVHP EPPQIKLEPS KLVRIRGEAA QIVCSATNAE VGFNVILKRG DTKLEIPLNS DFQDNYYKKV RALSLNAVDF QDAGIYSCVA SNDVGTRTAT MNFQVVESAY LNLTSEQSLL QEVSVGDSLI LTVHADAYPS IQHYNWTYLG PFFEDQRKLE FITQRAIYRY TFKLFLNRVK ASEAGQYFLM AQNKAGWNNL TFELTLRYPP EVSVTWMPVN GSDVLFCDVS GYPQPSVTWM ECRGHTDRCD EAQALQVWND THPEVLSQKP FDKVIIQSQL PIGTLKHNMT YFCKTHNSVG NSSQYFRAVS LGQSKQGFEP KSSDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPGK |

---

We claim:

1. A method of treating osteolytic bone loss in a patient comprising administering to the patient a therapeutically effective amount of a Colony Stimulating Factor 1 Receptor Extracellular Domain (CSF1R ECD) fusion molecule, wherein the amino acid sequence of the CSF1R ECD fusion molecule comprises SEQ ID NO:2 and excludes the last six C-terminal amino acid residues of SEQ ID NO:1.

2. The method of claim 1, wherein the amino acid sequence of the CSF1R ECD consists of SEQ ID NO:2.

3. The method of claim 1, wherein the CSF1R ECD fusion molecule comprises one or more fusion partners selected from an Fc, albumin, and polyethylene glycol.

4. The method of claim 3, wherein the one or more fusion partners is an Fc.

5. The method of claim 3, wherein the one or more fusion partners is polyethylene glycol.

6. The method of claim 3, wherein the one or more fusion partners is an Fc and polyethylene glycol.

7. The method of claim 1, wherein the amino acid sequence of the CSF1R ECD fusion molecule is produced from a Chinese hamster ovary (CHO) cell.

8. The method of claim 1, wherein the CSF1R ECD comprises a signal peptide.

9. The method of claim 1, wherein the fusion molecule comprises a linker between the CSF1R ECD and one or more fusion partners.

10. The method of claim 1, wherein the CSF1R ECD fusion molecule comprises SEQ ID NO:6.

11. The method of claim 10, wherein the CSF1R ECD fusion molecule consists of SEQ ID NO:6.

12. The method of claim 10, wherein the fusion molecule is produced from a CHO cell.

* * * * *